(12) United States Patent
Grimmer et al.

(10) Patent No.: US 10,724,077 B2
(45) Date of Patent: Jul. 28, 2020

(54) SELF-CONTAINED SYSTEM FOR CONSTRUCTING A NUCLEIC ACID PROFILE AND METHOD OF USING

(71) Applicant: Laboratory Corporation of America Holdings, Burlington, NC (US)

(72) Inventors: Nani M. Grimmer, Lorton, VA (US); Michael Neal Parsons, Lorton, VA (US); Abigail Bathrick, Lorton, VA (US); Donia Palomo Slack, Lorton, VA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 96 days.

(21) Appl. No.: 15/016,457

(22) Filed: Feb. 5, 2016

(65) Prior Publication Data
US 2017/0226569 A1    Aug. 10, 2017

(51) Int. Cl.
*G16B 30/00* (2019.01)
*C12Q 1/68* (2018.01)
*C12Q 1/6827* (2018.01)
*C12Q 1/6806* (2018.01)
*C12Q 1/6888* (2018.01)
*C12Q 1/6858* (2018.01)

(52) U.S. Cl.
CPC ......... *C12Q 1/6827* (2013.01); *C12Q 1/6806* (2013.01); *C12Q 1/6858* (2013.01); *C12Q 1/6888* (2013.01); *G16B 30/00* (2019.02)

(58) Field of Classification Search
None
See application file for complete search history.

(56) References Cited

U.S. PATENT DOCUMENTS

2013/0171045 A1* 7/2013 Ririe .................. B01L 3/502
                                                            422/559
2014/0038272 A1   2/2014 Ririe

OTHER PUBLICATIONS

Kim, et al., "Development of SNP-based human identification system", Int J Legal Med. 124 (2) (2010):125-31.
Pakstis, et al., "SNPs for a universal individual identification panel". Human Genetics 127:315-24. (2010).
Spichenok, et al., "Prediction of eye and skin color in diverse populations using seven SNPs", Forensic Sci. Int. Genet. (2010), doi: 10.1016/j.fsigen.2010.10.005.
Kayser et al., "DNA-based prediction of human externally visible characteristics in forensics: motivations, scientific challenges, and ethical considerations", Forensic Sci. Int. Genet 3 (2009): 154-161.
Nievergelt, et al., "Inference of human continental origin and admixture proportions using a highly discriminative ancestry informative 41-SNP panel". Investigative Genetics (Epub) 4:13. (2013).
Gettings, et al., "A 50-SNP assay for biogeographic ancestry and phenotype prediction in the U.S.population". Forensic Science International;Genetics 8:101-108. (2014).
Gibbs, et al, "Evolutionary and biomedical insights from the rhesus macaque genome," Science, vol. 316, pp. 222-234, 2007.
Ueda and Watanabe, "Characterization of human-specific DNA sequences obtained by genome substraction," Human Evolution, vol. 10, No. 1, pp. 63-68, 1995.
Kim, et al., "Use of autosomal loci for clustering individuals and populations of East Asian origin," Human Genetics, vol. 117, pp. 511-519, 2005.
Ueda, et al., "Human-specific sequences: isolation of species-specific DNA regions by genome subtraction," Genomics, vol. 8, pp. 7-12, 1990.
McCurley and Callard, "Characterization of housekeeping genes in zebrafish: male-female differences and effects of tissue type, development stage and chemical treatment," BMC Molecular Biology, vol. 9, No. 102, 2008.
Tang, et al., "Validation of zebrafish (*Danrio rerio*) reference genes for quantitative real-time RT-PCR normalization," Acta, vol. 39, No. 5, pp. 384-390, Biochimica et Biophysica Sinica.
Altschul, et al., "Basic local alignment search tool," Journal of Molecular Biology, vol. 215, pp. 403-410, 1990.
Pakstis, et al., "Candidate SNPs for a universal individual identification panel," Human Genetics, vol. 121, pp. 305-317, 2007.
K. K. Kidd, et al., "Developing a SNP panel for forensic identification of individuals," Forensic Science International, vol. 164, pp. 20-32, 2006.

* cited by examiner

*Primary Examiner* — James Martinell
(74) *Attorney, Agent, or Firm* — Robin L. Teskin; Baker, Donelson, Bearman, Caldwell & Berkowitz, PC

(57) ABSTRACT

The present invention relates to self-contained integrated systems and methods for constructing nucleic acid profiles of human individuals and for identification of the human individuals.

14 Claims, No Drawings
Specification includes a Sequence Listing.

SELF-CONTAINED SYSTEM FOR CONSTRUCTING A NUCLEIC ACID PROFILE AND METHOD OF USING

FIELD OF THE INVENTION

The present invention generally relates to self-contained integrated systems for constructing nucleic acid profiles of human individuals and for identification of the human individuals. Methods of using the systems for identifying human individuals are also presented.

BACKGROUND OF THE INVENTION

There is a capability gap in being able to rapidly identify human DNA in austere field forward environments. There are no current field portable devices for rapid human DNA identification, nor are there are any DNA based technologies that can rapidly predict human physical traits. Current DNA analysis is limited to being performed in forensic laboratories and often takes more than eight hours to construct a DNA profile. The capability for rapid field-forward identification of an individual can for example be useful in police stations to determine, prior to suspect release, or whether an individual may be associated with crime scene evidence; in immigration offices to support or reject claims of familial relatedness used to justify permission to immigrate, while at borders and ports; to determine whether individuals detained while entering the country illegally have profiles in terrorist DNA databases; in many applications in military settings, such as to distinguish friend from foe in combat, to permit access through military checkpoints, and to determine attribution of enemy munitions and weapons. The time between sample collection in the field and obtaining a result in the laboratory is currently too long to allow real-time decisions and dispositions in police, immigration, border, and military applications.

Currently, the most common method of human DNA identification is utilizing Short Tandem Repeats (STRs). STRs have a high power of discrimination between unrelated individuals (1 in $1.83 \times 10^{17}$ in Caucasian-Americans), but have a high mutation rate and limited use in degraded samples due to large amplification products. Additionally, rapid, integrated human DNA analysis devices are commercially available, however they are large, requiring laboratory foot space and are not portable and ready for field use.

Therefore, there is a need for integrated, self-contained systems for portable, on-site, field-forward, rapid human DNA genotyping with the capability of querying the genetic information for its correlation to identification or physical characteristics of an individual.

SUMMARY OF THE INVENTION

In one aspect, the present disclosure provides a self-contained system for constructing a nucleic acid profile of a human individual in a field forward position. The self-contained system is capable of constructing a nucleic acid profile capable of identification of the individual with a power of discrimination of more than 98%. The system comprises a reagent kit and an instrument for nucleic acid amplification and detection. The instrument corresponds to the reagent kit of the system.

The kit comprises means for isolating a nucleic acid sample from a biological material obtained from the individual and means for amplifying at least five nucleic acid amplification products from the nucleic acid sample. Each of the at least five nucleic acid amplification product comprises a single nucleotide polymorphism (SNP) suitable for constructing the nucleic acid profile of a human individual. The kit further comprises means for determining the genotypes of the SNP in the at least five amplification products. Determining the genotypes of the SNP in the at least five amplification products constructs the nucleic acid profile of the human individual.

The self-contained system may further comprise means for collecting the biological material. The means for collecting the biological material may be a foam swab with a point of breakage.

The means for isolating the nucleic acid sample from the biological material may comprise a combination of mechanical lysis and chemical cell lysis, followed by neutralization of the chemical lysis agent using a neutralizing agent and dilution of the nucleic acid sample. In some embodiments, the means for isolating the nucleic acid sample from the provided biological material may comprise a 5 ml vial comprising 600 µl NaOH at pH 12.5 and 1150 mg zirconium beads, and a double barreled syringe comprising 1780 µl water in a first barrel, and 120 µl neutralization buffer in a second barrel.

The means for amplifying and the means for determining the genotypes may be a single reagent-containing disposable comprising reagents for amplifying a nucleic acid amplification product comprising a single SNP and for determining the genotype of the SNP using Real Time PCR, and a means for introducing the sample to the reagent-containing disposable. The reagents in the single reagent-containing disposable may be lyophilized. In some embodiments, the single reagent-containing disposable may be a PCR vessel having at least one slot comprising one or more reagents for amplification of a human-specific control; at least one slot containing one or more reagents for an inhibition control; and at least five slots, each slot comprising reagents for amplifying a nucleic acid amplification product comprising a single SNP and for determining the genotype of the SNP using real time PCR. In other embodiments, the single reagent-containing disposable may be a PCR vessel comprising more than one slot, and wherein a first slot comprises reagents for amplification of a human-specific control; a second slot comprises reagents for an inhibition control; and at least ten slots, wherein each two slots of the at least ten slots comprise reagents for amplification of a single nucleic acid amplification product comprising a single SNP, and wherein a first of each two slots comprises one or more reagents for determining a first allele of the SNP, and a second of each two slots comprises reagents for determining a second allele of the SNP.

A SNP suitable for constructing the nucleic acid profile may have a heterozygosity of more than 0.4, and an $F_{st}$ of less than 0.06. In some embodiments, the at least five nucleic acid amplification products may comprise about five to about 20 SNPs selected from rs9866013, rs1019029, rs2291395, rs12480506, rs315791, rs12997453, rs7041158, rs2272998, rs13134862, rs3780962, rs433342, rs9546538, rs16891982, rs310644, rs1426654, rs3827760, rs4891825, rs4918664, rs10497191, rs12913832, rs1876482, and combinations thereof. In other embodiments, the at least five nucleic acid amplification products may comprise the SNPs rs9866013, rs1019029, rs2291395, rs12480506, and rs315791.

In some embodiments, the system comprises a 5 ml vial comprising 600 µl NaOH at pH of 12.5 and 1150 mg zirconium beads, and a double barreled syringe comprising 1780 µl water in a first barrel, and 120 µl neutralization buffer in a second barrel; a reagent pouch for use with a RAZOR® EX instrument, wherein the reagent pouch comprises freeze-dried reagents for amplifying nucleic acid amplification products comprising the rs9866013, rs1019029, rs2291395, rs12480506, and rs315791 SNPs and determining the genotypes of the SNPs, and reagents for amplification of the HS5 human-specific control, and a beta actin inhibition control; a 3 ml syringe; and a RAZOR® EX instrument.

In some embodiments, the system may comprise a 5 ml vial comprising 600 µl NaOH at pH of 12.5 and 1150 mg zirconium beads, and a double barreled syringe comprising 1780 µl water in a first barrel, and 120 µl neutralization buffer in a second barrel; a reagent pouch for use with a RAZOR® EX instrument; a 3 ml syringe; and a RAZOR® EX instrument. The reagent pouch comprises a first slot comprising freeze-dried reagents for amplifying and determining the presence of an HS5 human-specific control; a second slot comprising freeze-dried reagents for amplifying and determining the presence of a βactin1 inhibition control; and at least ten slots, wherein each two slots of the at least ten slots comprise freeze-dried reagents for amplification of a single nucleic acid amplification product selected from the rs9866013, rs1019029, rs2291395, rs12480506, and rs315791 SNPs, and wherein a first of each two slots comprises one or more reagents for determining a first allele of each SNP, and a second of each two slots comprises reagents for determining a second allele of each SNP. In an alternative of the embodiments, the reagent pouch may comprise a first slot comprising freeze-dried reagents for amplifying and determining the presence of an HS5 human-specific control, the freeze-dried reagents comprising a forward primer of SEQ ID NO: 24, a reverse primer of SEQ ID NO: 25, and a TaqMan probe of SEQ ID NO: 26; a second slot comprising freeze-dried reagents for amplifying and determining the presence of a βactin1 inhibition control, the freeze-dried reagents comprising a forward primer of SEQ ID NO: 27, a reverse primer of SEQ ID NO: 28, a TaqMan probe of SEQ ID NO: 29, and a template of SEQ ID NO: 30; a third slot comprising freeze-dried reagents for amplifying and determining a C allele of the rs9866013 SNP, the freeze-dried reagents comprising a forward primer of SEQ ID NO: 31, a reverse primer of SEQ ID NO: 32, and a TaqMan probe of SEQ ID NO: 33; a fourth slot comprising freeze-dried reagents for amplifying and determining a T allele of the rs9866013 SNP, the freeze-dried reagents comprising a forward primer of SEQ ID NO: 31, a reverse primer of SEQ ID NO: 32, and a TaqMan probe of SEQ ID NO: 34; a fifth slot comprising freeze-dried reagents for amplifying and determining a C allele of the rs1019029 SNP, the freeze-dried reagents comprising a forward primer of SEQ ID NO: 35, a reverse primer of SEQ ID NO: 36, and a TaqMan probe of SEQ ID NO: 37; a sixth slot comprising freeze-dried reagents for amplifying and determining a T allele of the rs1019029 SNP, the freeze-dried reagents comprising a forward primer of SEQ ID NO: 35, a reverse primer of SEQ ID NO: 36, and a TaqMan probe of SEQ ID NO: 38; a seventh slot comprising freeze-dried reagents for amplifying and determining an A allele of the rs2291395 SNP, the freeze-dried reagents comprising a forward primer of SEQ ID NO: 39, a reverse primer of SEQ ID NO: 40, and a TaqMan probe of SEQ ID NO: 41; an eighth slot comprising freeze-dried reagents for amplifying and determining a G allele of the rs2291395 SNP, the freeze-dried reagents comprising a forward primer of SEQ ID NO: 39, a reverse primer of SEQ ID NO: 40, and a TaqMan probe of SEQ ID NO: 42; a ninth slot comprising freeze-dried reagents for amplifying and determining an A allele of the rs12480506 SNP, the freeze-dried reagents comprising a forward primer of SEQ ID NO: 43, a reverse primer of SEQ ID NO: 44, and a TaqMan probe of SEQ ID NO: 45; a tenth slot comprising freeze-dried reagents for amplifying and determining a G allele of the rs12480506 SNP, the freeze-dried reagents comprising a forward primer of SEQ ID NO: 43, a reverse primer of SEQ ID NO: 44, and a TaqMan probe of SEQ ID NO: 46; an eleventh slot comprising freeze-dried reagents for amplifying and determining an A allele of the rs315791 SNP, the freeze-dried reagents comprising a forward primer of SEQ ID NO: 47, a reverse primer of SEQ ID NO: 48, and a TaqMan probe of SEQ ID NO: 49; and a twelfth slot comprising freeze-dried reagents for amplifying and determining a C allele of the rs315791 SNP, the freeze-dried reagents comprising a forward primer of SEQ ID NO: 47, a reverse primer of SEQ ID NO: 48, and a TaqMan probe of SEQ ID NO: 50.

In another aspect, the present disclosure provides a method of constructing a nucleic acid profile of a human individual in a field forward position. The method comprises providing biological material from the human individual; providing a self-contained system for constructing a nucleic acid profile of a human individual in a field forward position as described above; using the self-contained system to isolate a nucleic acid sample from the biological material; using the self-contained system to amplify at least five nucleic acid amplification products from the nucleic acid sample, wherein each amplification product comprises a single nucleotide polymorphism (SNP); and using the self-contained system to determine the genotypes of the SNPs in the one or more amplification products, thereby constructing the nucleic acid profile of the human individual.

In some embodiments, the nucleic acid profile of the human individual may be further converted to a simplified pattern using a code selected from a symbolic code, a colorimetric code, and a numerical code. In an alternative of the embodiments, the nucleic acid profile of the human individual is further converted to a simplified pattern using a symbolic code.

In yet another aspect, the present disclosure provides a method of identifying an unidentified human individual. The method comprises providing biological material from the unidentified human individual; providing a self-contained system as described above; constructing a first nucleic acid profile of the unidentified human individual using a method of constructing a nucleic acid profile of a human individual in a field forward position as described above; and comparing the first nucleic acid profile to a second nucleic acid profile obtained from a biological sample derived from an identified human individual. If the first nucleic acid profile matches the second nucleic acid profile, the unidentified individual is identified. The first nucleic acid profile of the human individual may be further converted to a first simplified pattern using a code before comparing the first simplified pattern to a second simplified pattern generated from a second nucleic acid profile obtained from a biological sample derived from a referenced human individual, thereby identifying the unidentified human individual.

DETAILED DESCRIPTION

A system for constructing a nucleic acid profile of a human individual has been developed. A system of the present disclosure provides means for nucleic acid isolation from a provided sample, means for amplification of nucleic acid amplification products comprising single nucleotide polymorphisms (SNP) from the nucleic acid sample, and means for determining the genotypes of the SNP in the amplification products, whereby determining the genotypes of the SNP in the amplification products constructs the nucleic acid profile of the human individual. Methods of using a system of the present disclosure are also provided. A system of the present disclosure is self-contained. As such, a system provides everything that may be required for sample preparation from a provided biological sample, nucleic acid amplification, and genotyping, in a simple, convenient, easy-to-operate format. A system may further provide means for providing a biological specimen for analysis.

Advantageously, a self-contained system of the present disclosure is capable of rapidly constructing a nucleic acid profile of a human individual in austere field-forward environments. In fact, self-contained systems are capable of providing actionable results in less than about 45 minutes, or even less than about 30 minutes. A self-contained system provides for ease of use for nontechnical operators with scripted minimal manual processing steps, reagent loading, assembly, or maintenance; ease of use for nontechnical operators outside of the laboratory thereby reducing time to obtain and act on the result; match-or-no-match reporting of critical information to the operator in a straightforward fashion to allow prompt decision-making; rapid time to results to have a practical impact on individual processing in field-forward settings; has minimal space, laboratory equipment, and controlled laboratory environmental requirements; is rugged, capable of withstanding transport without recalibration; provides accurate results; and provides for minimal sample contamination and user exposure. The self-contained nature of systems minimizes operating procedures and operator requirements. As such, self-contained systems dramatically simplify the process of constructing a nucleic acid profile of a human individual in a field forward position. Another advantage of the self-contained system of the invention is that this format reduces both the possibility of sample contamination as well as operator exposure to sample, reagents, and process waste.

I. Self-Contained System

In one aspect, a self-contained system for constructing a nucleic acid profile of a human individual in a field forward position is provided. Self-contained systems comprise a reagent kit, the reagent kit comprising means for nucleic acid isolation from a biological material, amplification of nucleic acid amplification products comprising single nucleotide polymorphisms (SNPs), and genotyping of SNPs. A self-contained system further comprises an instrument for nucleic acid amplification and genotyping. In some embodiments, a system may further comprise means for collecting a biological material for analysis using the self-contained system of the disclosure. The reagent kit and the instrument work in tandem to construct a nucleic acid profile of a human individual. All the components of the integrated system may be packaged together and clearly labeled to follow simple instructions.

Self-contained systems according to the present disclosure preferably further include instructions for genetic profiling of a human individual in a field forward position. Instructions included in systems of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

a. Reagent Kit

A self-contained system of the present disclosure comprises a reagent kit. A reagent kit comprises means for isolating a nucleic acid sample from a biological material, means for amplifying nucleic acid amplification products from the nucleic acid sample wherein each amplification product comprises a SNP suitable for constructing the nucleic acid profile of a human individual, and means for determining the genotypes of the SNPs in the amplification products. Means for isolating, amplifying, and genotyping of a reagent kit comprise reagents and disposables comprising the reagents for performing each step in a method for isolating, amplifying, and genotyping.

A reagent kit may comprise a single reagent-containing disposable capable of isolating a nucleic acid sample from a biological material, amplifying nucleic acid amplification products comprising SNPs, and determining the genotypes of the SNPs in the amplification products. Alternatively, a kit may comprise more than a single reagent-containing disposable to perform the three means of the kit or combinations thereof. For instance, a kit may comprise a reagent-containing disposable for isolating a nucleic acid sample, a reagent-containing disposable for amplifying nucleic acid amplification products, and a reagent-containing disposable for determining the genotypes of the SNPs in the amplification products. Alternatively, a kit may comprise a single reagent-containing disposable for isolating a nucleic acid sample and amplifying nucleic acid amplification products, and a reagent-containing disposable determining the genotypes of the SNPs in the amplification products. Additionally, a kit may comprise a reagent-containing disposable for isolating a nucleic acid sample, and a single reagent-containing disposable for amplifying nucleic acid amplification products and determining the genotypes of the SNPs in the amplification products.

Preferably, a kit of the present disclosure comprises a reagent-containing disposable for isolating a nucleic acid sample, and a single reagent-containing disposable for amplifying nucleic acid amplification products and determining the genotypes of the SNPs in the amplification products.

The term "biological material" is used herein in a broad sense and is intended to include a wide range of biological materials as well as compositions derived or extracted from such biological materials. In general, a "biological material" according to the invention is any specimen from which nucleic acids can be obtained. Biological materials obtained from forensic settings are also within the intended meaning of the term sample.

Exemplary biological materials include whole blood; red blood cells; white blood cells; buffy coat; hair; nails and cuticle material; swabs, including but not limited to buccal swabs, throat swabs, vaginal swabs, urethral swabs, cervical swabs, throat swabs, rectal swabs, lesion swabs, abscess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, biopsy material, and the like, and biological materials remaining on a personal effect, such as a toothbrush, bedding, a razor, a glass used for drinking, a cigarette butt, or a hairbrush. For instance, an unknown biological specimen may be derived from living tissue (e.g., a biopsy) or from deceased tissue (e.g., a remain), bone fragments, hair, or fingernail scrapings. A biological material may be from an identified individual, an unidentified individual, or is suspected to be from an identified or unidentified individual. An individual may be deceased. Alternatively, an individual may be living. The skilled artisan will appreciate that lysates, extracts, or material obtained from any of the above exemplary biological materials. Tissue culture cells, including explanted material, primary cells, secondary cell lines, and the like, as well as lysates, extracts, or materials obtained from any cells, are also within the meaning of the term biological material as used herein. Microorganisms and viruses that may be present on or in a sample are also within the scope of the invention.

In some embodiments, a kit may further comprise means for collecting a biological material. In general, fibrous swabs are normally used to collect a biological material. As such, a kit may further comprise a swab for collecting a biological material. Swabs may be made of fibers of cotton, cellulose, rayon, polyester, and other types of fibers. Such swabs not only absorb liquids and solids entrained in liquids but also trap dry substances such as particulate materials. Swabs are normally kept in closed bags or containers prior to use to maintain sterility and are replaced in such containers after use to avoid contamination of the sample gathered. Conventional swabs are formed of a "stick" such as a shaft of wood, tubular plastic, or tubular or rolled paper with a pad of cotton or other fiber, sponge material, or other absorbent material attached to the end of the shaft, either mechanically or by an inert adhesive. Swabs may further comprise a point of breakage along the shaft to separate a swab from the shaft t and to allow the swab to be deposited within a separate container. Preferably, a reagent kit of the present disclosure further comprises a swab comprising a point of breakage for collecting a biological material.

SNPs suitable for constructing the nucleic acid profile of a human individual, a reagent-containing disposable for isolating a nucleic acid sample, and a reagent-containing disposable for amplifying nucleic acid amplification products and determining the genotypes of the SNPs in the amplification products are described below.

A. SNPs Suitable for Constructing a Nucleic Acid Profile

An integrated system of the present disclosure is capable of constructing a nucleic acid profile of a human individual by determining the genotype of one or more SNPs in a nucleic acid sample obtained from the individual. SNPs are single base sequence variations between individuals at particular points in the genome of the individual.

Some advantages of using SNPs for constructing a nucleic acid profile of a human individual are as follows: (1) SNPs have essentially zero rate of recurrent mutation. Therefore, the likelihood of a mutation confounding typing is negligible and far less than other potential artifacts in typing. (2) SNPs have the potential for accurate automated typing and allele calling. The allelic nature of SNPs means that allele calling is a qualitative issue not a quantitative issue. (3) Small amplicon size is achievable with SNPs. With reliable procedures, many SNPs can potentially be genotyped using very short recognition sequences—in the range of 45-55 bp. As it will be recognized by individuals skilled in the art, such short amplicons (merely the length of the two flanking PCR primers) is extremely valuable when DNA samples are severely degraded. (4) Finally, SNP typing can be multiplexed and done very quickly.

A "nucleic acid profile" of a human individual according to the present disclosure comprises the genotype of the one or more SNPs in the nucleic acid sequence of the individual. Constructing such a nucleic acid panel can provide for identification of the individual as described further below. Any number of SNPs may be used in an integrated system of the present disclosure to construct a nucleic acid profile of a human individual, provided the number of SNPs can provide a nucleic acid profile capable of identification of an individual with a power of discrimination of more than 85%. For instance, a nucleic acid profile may be capable of identification of an individual with a power of discrimination of more than 85%, 90%, 95% or may even be capable of identification of an individual with a perfect power of discrimination of 100%. Preferably, a nucleic acid profile of the present disclosure is capable of identification of an individual with a power of discrimination of more than 95%, preferably more than 96, 97, or 98%. In exemplary embodiments, a nucleic acid profile of the present disclosure is capable of identification of an individual with a power of discrimination of more than 98%.

The number of SNPs used to construct a nucleic acid profile of a human individual may be about 1, 2, 3, 4, 5, 6, 7, 8, 9, 10, 11, 12, 13, 14, 15, 16, 17, 18, 19, 20, 21, or more. Preferably, the number of SNPs used to construct a nucleic acid profile of a human individual is about 1, 2, 3, 4, 5, 6, 7, 8, 9, or about 10, more preferably about 3, 4, 5, 6, 7, or about 8. In exemplary embodiments, the number of SNPs used to construct a nucleic acid profile of a human individual is 5.

A SNP of the present disclosure must be suitable for constructing a nucleic acid profile that is useful for identifying a human individual. In essence, a suitable SNP of the present disclosure has high heterozygosity and essentially identical allele frequencies in all populations across the world. When a SNP has high heterozygosity and essentially identical allele frequencies in all populations, the match probability would be nearly constant irrespective of the population. High heterozygosity maximizes the information at each SNP and low genetic variance among populations ($F_{ST}$) minimizes the chance effects between populations. Thus, the combination of high heterozygosity and low $F_{ST}$ increases the efficiency of a forensic panel—that is, it will take fewer SNPs to produce lower match probabilities than if random SNPs are used.

Preferably, SNPs suitable for use in a self-contained system of the present disclosure have a heterozygosity of >0.3, 0.35, 0.4, or 0.45, and a $F_{ST}$ of <0.08, 0.07, 0.06, 0.05, or 0.04. More preferably, SNPs suitable for use in a self-contained system of the present disclosure have a heterozygosity of >0.4, and a $F_{ST}$ of <0.06.

SNPs suitable for suitable for constructing a nucleic acid profile of a human individual have been identified. See for example (Kidd et al., 2006 "Developing a SNP panel for forensic identification of individuals" Forensic Science International, 164:20-32; Pakstis et al., 2007 "Candidate SNPs for a universal individual identification panel," Human Genetics, 121:305-17; Pakstis et al., 2010 "SNPs for a universal individual identification panel," Human Genetics, 127:315-24; Nievergelt et al., 2013 "Inference of human continental origin and admixture proportions using a highly discriminative ancestry informative 41-SNP panel," Investigative Genetics, 4:23; Gettings et al., 2014 "A 5-SNP assay for biogeographic ancestry and phenotype prediction in the U.S. population" Forensic Science International: Genetics, 8:101-108). Preferred SNPs suitable for individual identification using a self-contained system of the present disclosure are shown in Table A.

TABLE A

| SEQ. ID. NO. | SNP Reference No. | Allele |
|---|---|---|
| 1 | rs9866013 | C or T |
| 2 | rs1019029 | C or T |
| 3 | rs2291395 | A or G |
| 4 | rs12480506 | A or G |
| 5 | rs315791 | A or C |
| 6 | rs12997453 | A or G |
| 7 | rs7041158 | C or T |
| 8 | rs2272998 | C, G, or T |
| 9 | rs13134862 | A or G |
| 10 | rs3780962 | C or T |
| 11 | rs433342 | A, C, or G |
| 12 | rs9546538 | C or T |
| 13 | rs16891982 | C or G |
| 14 | rs310644 | A or G |
| 15 | rs1426654 | A or G |
| 16 | rs3827760 | C or T |
| 17 | rs4891825 | A or G |
| 18 | rs4918664 | A or G |
| 19 | rs10497191 | C or T |
| 20 | rs12913832 | A or G |
| 21 | rs1876482 | C or T |

In an exemplary embodiment, the SNPs genotyped in an integrated system of the present disclosure to construct a nucleic acid profile of a human individual are rs9866013, rs1019029, rs2291395, rs12480506, and rs315791.

B. Means for Isolating a Nucleic Acid Sample

A means for isolating a nucleic acid sample from a biological material in the context of this invention comprises one or more reagent-filled disposable sufficient for use in a method for isolating the nucleic acid sample from the biological material. An isolated nucleic acid sample may include but need not be limited to RNA, cDNA, tRNA, mitochondrial DNA, ribosomal DNA, plasmid DNA, siRNA, genomic DNA, or any other naturally occurring or artificial nucleic acid molecule originating from a human individual. Preferably, a nucleic acid sample comprises genomic DNA.

Any method for isolating a nucleic acid sample from a biological material can be used, provided the method produces a nucleic acid sample in a form sufficiently pure to enable amplifying nucleic acid amplification products from the nucleic acid sample and determining the genotypes of the SNPs in the amplification products. Methods for isolating a nucleic acid sample from a biological material that are compatible with the present invention are known in the art (see, e.g., Gurvitz et al. "Exploiting biological materials in forensic science." Australas Biotechnol. 1994 March-April 4(2):88-91; Ma et al. "Extraction of high quality genomic DNA from microsamples of human blood." J Forensic Sci Soc. 1994 October-December 34(4):231-5; Laber et al. "Evaluation of four deoxyribonucleic acid (DNA) extraction protocols for DNA yield and variation in restriction fragment length polymorphism (RFLP) sizes under varying gel conditions." J Forensic Sci. 1992 March; 37(2):404-24.) Most preferred is extracting nucleic acid without further purifying the nucleic acid sample from impurities to simplify processing.

Preferably, a means for isolating a nucleic acid sample from a biological material comprises a cell lysis method and one or more reagent-containing disposables for cell lysis. Cell lysis methods are well known in the art and include cell lysis using mechanical or physical disruption of cell membranes, enzymatic lysis, chemical disruption of cell membranes, or combinations thereof. Non-limiting examples of mechanical cell lysis include sonication, pressure, such as the use of a French cell press, homogenization, grinding, freeze-thaw lysis, and grinding beads such as zirconium or glass grinding beads. Non-limiting examples of enzymatic disruption of cell membranes includes the use of lytic enzymes. Exemplary enzymes include beta glucurondiase; glucanase; glusulase; lysozyme; lyticase; mannanase; mutanolysin; zymolyase, cellulase, chitinase, lysostaphin, pectolyse, streptolysin O, and various combinations thereof. See, e.g., Wolska-Mitaszko, et al., Analytical Biochem., 116:241-47 (1981); Wiseman, Process Biochem., 63-65 (1969); and Andrews & Asenjo, Trends in Biotech., 5:273-77 (1987). Non-limiting examples of chemical disruption of cell membranes includes the use of alkaline denaturing agents such as sodium hydroxide (NaOH), detergents, chaotropic agents, or combinations thereof. Non-limiting examples of suitable detergents commonly used in the art for cell lysis include Triton X-100, Triton X-114, NP-40, Brij-35, Brij-58, Tween 20, Tween 80, Octyl glucoside, Octyl thioglucoside, SDS, CHAPS, CHAPSO, n-dodecyl-beta-maltoside, and sodium deoxycholate. Non-limiting examples of suitable chaotropic agents commonly used in the art for cell lysis include urea, guanidine HCl, guanidine thiocyanate, guanidium thiosulfate, and thiourea. As it will be recognized by an individual skilled in the art, chemical and enzymatic lysis methods may further comprise the use of neutralizing agents to stop the action of the chemical or enzymatic agent to prepare a sample for further manipulation. For instance, chemical lysis by alkaline lysis using NaOH is normally followed by neutralization of NaOH using an acid such as sodium acetate or potassium acetate.

In preferred embodiments, a means for isolating a nucleic acid sample from a provided biological material comprises a combination of mechanical lysis and chemical cell lysis, followed by neutralization of the chemical lysis agent using a neutralizing agent. In a preferred alternative of the embodiments, a means for isolating further comprises providing a diluent and a disposable comprising the diluent to dilute the lysed sample. Preferably, mechanical lysis is by zirconium beads, chemical lysis is by NaOH alkaline denaturing agent, neutralizing is by potassium acetate, and dilution is by water. As such, a preferred means for isolating a nucleic acid sample from a provided biological material comprises a reagent-filled disposable comprising a combination of zirconium beads and NaOH alkaline denaturing agent, a reagent filled disposable comprising potassium acetate neutralizing agent, and a reagent filled disposable comprising water diluting agent.

In exemplary embodiments, a means for isolating a nucleic acid sample from a provided biological material comprises a 5 ml vial comprising 600 μl NaOH solution at pH of 12.5 and 1150 mg zirconium beads, and a double barreled syringe comprising 1780 μl water in a first barrel and 120 μl neutralization buffer at pH of 9.5 in a second barrel.

C. Means for Amplifying Nucleic Acid Amplification Products and Determining the Genotypes A reagent kit of the present disclosure also comprises a means for amplifying nucleic acid amplification products comprising SNPs and a means for determining the genotypes of the SNPs in the amplification products. Preferably, a means for amplifying nucleic acid amplification products comprising SNPs and a means for determining the genotypes of the SNPs in the amplification products comprise reagents for use in methods for amplifying and genotyping that are compatible and can be performed simultaneously in a single disposable. As such, a single disposable comprises everything necessary for performing both the amplifying and the determining functions of the integrated system. Such compatible amplification and genotyping methods are described below.

As used herein, the phrase "amplifying a nucleic acid amplification product" is used to describe increasing the number of copies of a nucleic acid molecule. Suitable amplification methods include ligase chain reaction (see, e.g., Wu & Wallace, Genomics 4:560-569, 1988); strand displacement assay (see, e.g. Walker et al., Proc. Natl. Acad. Sci. USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., Proc. Natl. Acad. Sci. USA 86:1173-1177, 1989); and self-sustained sequence replication (3SR) (Guatelli et al., Proc. Natl. Acad. Sci. USA 87:1874-1878, 1990; WO 92/08800). A review of suitable amplification methods is provided, for example, by Abramson and Myers in Current Opinion in Biotechnology 4:41-47, 1993. If an mRNA gene product is to be amplified, it will first be converted into a cDNA molecule by reverse transcription using a reverse transcriptase enzyme to generate a cDNA molecule. Upon completion of the reverse transcription reaction, the cDNA can be used as the template for the primer-dependent nucleic acid amplification reaction. A person skilled in the art will be well aware of how to generate cDNA molecules from mRNA molecules.

In a preferred embodiment of the present invention, a means for amplifying nucleic acid amplification products comprises a primer-dependent nucleic acid amplification reaction. Ample guidance for performing primer-dependent amplification is provided in the art. Exemplary references include manuals such as PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Current Protocols in Molecular Biology (Ausubel et al., John Wiley & Sons, New York, 2003); Molecular Cloning: A Laboratory Manual (Sambrook & Russell, Cold Spring Harbor Press, Cold Spring Harbor, N.Y., $3^{rd}$ Ed, 2001).

Preferably, a primer-dependent nucleic acid amplification reaction is the polymerase chain reaction (PCR). In a PCR-based amplification, forward and reverse primers specific for the intended amplification product of the invention are contacted with a reaction mixture comprising a nucleic acid target sequence and free nucleotides in a suitable buffer. Thermal cycling of the resulting mixture in the presence of a DNA polymerase results in amplification of the sequence between the primers. Alternatively, PCR amplification may be performed at a uniform temperature (isothermal PCR). Examples of isothermal PCR methods may include the ramification amplifying method and the helicase-dependent amplification method. Preferably, a means for amplifying a nucleic acid amplification product uses primer-dependent PCR with thermal cycling.

Many variations of PCR have been developed, for instance Real Time PCR (also known as quantitative PCR, qPCR), hot-start PCR, competitive PCR, and so on, and these may all be employed where appropriate to the needs of the skilled man. In preferred embodiments, a PCR variant suitable for use in the present disclosure is a combination of Real Time PCR and hot-start PCR.

Methods of designing and synthesizing primers for amplifying a nucleic acid sequence using a PCR reaction are known in the art. PCR primers may be designed using standard primer design computer software techniques known to individuals skilled in the art. The variables considered during PCR primer design may include primer length, GC pair content, melting temperature, and size of the target nucleic acid amplified by the primer pair. Generally speaking, primers should not form hairpin structures or self- or hetero-primer pairs, but in some embodiments a primer forming a hairpin structure may be used.

Primers may comprise a sequence of 15, 20, 25, 30, 35, 40, 45, 50 or more bases complementary to a portion of a template. Preferably, primers have a sequence of 15-30 bases, more preferably 15-25 bases complementary to a portion of a nucleic acid sequence template. The melting temperature of primers may be 50, 55, 60, 65, 70 or 75° C. Preferably, the melting temperature of primers ranges between 50 and 70° C., more preferably between 55 and 65° C., and even more preferably between 58 and 60° C. The melting temperature of each primer of a primer pair may be the same. Alternatively, the melting temperature of each primer of a primer pair may be different for each primer. The difference in melting temperatures between each primer of a primer pair may be 1, 2, 3, 4, 5, 6, 7, 8, 9° C. or more. A primer pair may be designed to amplify a nucleic acid target product that may be 20, 30, 40, 50, 60, 70, 80, 90, 100, 200, 300, 400, 500, 600, 700, 800, or more base pairs in length. Preferably, a primer pair is designed to amplify a nucleic acid target product that is 20 to 400 base pairs in length, more preferably, 50-150 base pairs in length. The combined concentration of a forward and reverse primer in a PCR reaction may range from about 0.4 to about 1 µM, more preferably from about 0.6 to about 0.9 µM, and even more preferably about 0.8 µM.

A PCR reaction generally comprises a thermostable DNA polymerase. A thermostable DNA polymerase is an enzyme that is relatively stable to heat and eliminates the need to add enzyme prior to each PCR cycle. Non-limiting examples of thermostable polymerases may include polymerases isolated from the thermophilic bacteria *Thermus aquaticus* (Taq polymerase), *Thermus thermophilus* (Tth polymerase), *Thermococcus litoralis* (Tli or VENT™ polymerase), *Pyrococcus furiosus* (Pfu or DEEPVENT™ polymerase), *Pyrococcus woosii* (Pwo polymerase) and other *Pyrococcus* species, *Bacillus stearothermophilus* (Bst polymerase), *Sulfolobus acidocaldarius* (Sac polymerase), *Thermoplasma acidophilum* (Tac polymerase), *Thermus rubber* (Tru polymerase), *Thermus brockianus* (DYNAZYME™ polymerase) *Thermotoga neapolitana* (Tne polymerase), *Thermotoga maritime* (Tma) and other species of the *Thermotoga* genus (Tsp polymerase), and *Methanobacterium thermoautotrophicum* (Mth polymerase). The PCR reaction may comprise more than one thermostable polymerase with complementary properties leading to more efficient amplification of target sequences. For example, a nucleotide polymerase with high processivity (the ability to copy large nucleotide segments) may be complemented with another nucleotide polymerase with proofreading capabilities (the ability to correct mistakes during elongation of target nucleic acid sequence), thus creating a PCR reaction that can copy a long target sequence with high fidelity. The thermostable polymerase may be used in its wild type form. Alternatively, the polymerase may be modified to contain a fragment of the enzyme or to contain a mutation that provides beneficial properties to facilitate the PCR reaction. In one embodiment, the thermostable polymerase may be Taq polymerase. Many variants of Taq polymerase with enhanced properties are known and include AmpliTaq™, AmpliTaq™ Stoffel fragment, SuperTaq™, SuperTaq™ plus, LA Taq™, LApro Taq™, and EX Taq™. In a preferred embodiment, the thermostable polymerase is Taq polymerase. The concentration of DNA polymerase in a PCR reaction may range from about 0.01 to about 0.1 U/µL, more preferably from about 0.02 to about 0.08 U/µL, and even more preferably from about 0.04 to about 0.06 U/µL.

Preferably, a means for amplifying nucleic acid amplification products comprises reagents for a hot-start PCR method. In conventional PCR, a DNA polymerase is active at room temperature and to a lesser degree, even on ice. In some instances, when all the reaction components are put together, nonspecific primer annealing can occur due to these low temperatures. This nonspecific annealed primer can then be extended by the thermostable DNA polymerase of the reaction, generating nonspecific products and lowering product yields. Hot Start PCR significantly reduces nonspecific priming, the formation of primer dimers, and often, increases product yields. In hot start PCR, an amplification reaction further comprises an antibody against a DNA polymerase of the PCR reaction. Such an antibody inhibits polymerase activity before the onset of thermal cycling, preventing nonspecific amplification and primer dimer formation. When the reaction temperature is raised, the antibody is quickly inactivated and PCR proceeds. Preferably, a hot start PCR method for amplifying a nucleic acid amplification product comprises the TaqStart Antibody. The concentration of TaqStart Antibody in a PCR reaction may range from about 0.005 µg/µL to about 0.01 µg/µL, preferably about 0.0088 µg/µL.

Means suitable for determining the genotypes of the at least five SNPs are well known in the art. See for example Single Nucleotide Polymorphisms: Methods and Protocols, Pui-Yan Kwok, ed., 2003, Humana Press. Suitable means include allele-specific real time PCR, 5'-nuclease assays, template-directed dye-terminator incorporation, molecular beacon allele-specific oligonucleotide assays, assays employing invasive cleavage with Flap nucleases, allele-specific hybridization (ASH), molecular beacons (e.g., Scorpion probes), fluorescence resonance energy transfer (FRET) probes, induced FRET (iFRET) probes, minor grove binder (MGB) probes (e.g., MGB Eclipse probes), molecular torches, hybridization switch probes, array based hybridization, allele-specific ligation, primer extension, single-base extension (SBE) assays, sequencing, pyrophosphate sequencing, real-time pyrophosphate sequencing, sequence length polymorphism analysis, restriction length fragment polymorphisms (RFLP), RFLP-PCR, single-stranded conformational polymorphism (SSCP), PCR-SSCP, fragment sizing capillary electrophoresis, heteroduplex analysis, and mass array systems.

Preferably, a means for determining the genotype of the at least five SNPs comprises allele-specific hybridization (ASH). In essence, ASH comprises the use of an oligonucleotide as a probe for the presence of a target allele in a nucleic acid sequence. An ASH oligonucleotide probe is complementary to the sequence of a target nucleic acid sequence, and designed and used to be specific for only one version, or allele, of a nucleic acid sequence. For instance, when a nucleic acid sequence comprises a SNP, an ASH probe specifically binds to one version, or allele, of the nucleic acid sequence. Detecting the interaction of the ASH probe with the nucleic acid sequence determines the genotype of the SNP. Therefore, an ASH oligonucleotide acts as a probe for the presence of a target allele in nucleic acid sequence analysis. Advantageously, a means for determining the genotype of the at least five SNPs that comprises ASH probes can be readily used with Real Time PCR to determine the genotype of an SNP in the amplified nucleic acid target sequence.

In general, a probe is a nucleic acid oligonucleotide further comprising a label to detect the interaction of the probe with the nucleic acid sequence. As used herein, "label" refers to any atom or molecule which can provide a detectable signal, and which can be attached to a nucleic acid. Labels provide detectable signals that can quantitatively and qualitatively indicate the presence or absence of a specific nucleotide sequence. Labels can provide signals detectable by such techniques as colorimetric, fluorescent, electrophoretic, electrochemical, spectroscopic, chromatographic, densitometric, or radiographic techniques, and the like. Suitable labels for the present invention include, but are not limited to, enzyme substrates, radioactive atoms, fluorescent dyes, chromophores, chemiluminescent labels, electrochemiluminescent labels, ligands having specific binding partners, or any other labels that can interact with each other to enhance, alter, or diminish a signal. Labels may be self-quenching when comprised in a self-quenched oligonucleotide probe. Self-quenched fluorescent oligonucleotide probes may be as described in Nazarenko et al. 2002 (Multiplex quantitative PCR using self-quenched primers labeled with a single fluorophore. Nucleic Acids Research, 30:e37). Alternatively, labels may be molecules that do not themselves produce a detectable signal, but when used in conjunction with another label can produce or quench a detectable signal. For example, a label can be a quencher of a quencher-dye pair.

Preferably, a label comprises a fluorescent dye. As used herein, the terms "fluorophore" and "fluorescent dye" are used interchangeably and describe a chemical compound, which when excited by exposure to a particular wavelength of light, emits light (fluoresces), for example at a different wavelength of light. Also encompassed by the term "fluorophore" are luminescent molecules, which are chemical compounds which do not require exposure to a particular wavelength of light to fluoresce; luminescent compounds naturally fluoresce. Therefore, the use of luminescent signals can eliminate the need for an external source of electromagnetic radiation, such as a laser. Suitable fluorescent dyes include, for example, fluorescein, cascade blue, hexachloro-fluorescein, tetrachloro-fluorescein, TAMRA, ROX, Cy3, Cy3.5, Cy5, Cy5.5, 4,4-difluoro-5,7-diphenyl-4-bora-3a,4a-diaza-s-indacene-3-propionic acid, 4,4-difluoro-5,p-methoxyphenyl-4-bora-3a,4a-diaza-s-indacene-3-propionic acid, 4,4-difluoro-5-styryl-4-bora-3a,4-adiaza-S-indacene-propionic acid, 6-carboxy-X-rhodamine, N,N,N',N'-tetramethyl-6-carboxyrhodamine, 6-carboxyfluorescein (6-FAM), Texas Red, Eosin, fluorescein, 4,4-difluoro-5,7-diphenyl-4-bora-3a,4a-diaza-s-indacene-3-propionic acid, 4,4-difluoro-5,p-ethoxyphenyl-4-bora-3a,4a-diaza-s-indacene 3-propionic acid and 4,4-difluoro-5-styryl-4-bora-3a,4a-diaza-S-indacene-propionic acid, 2',7'-dimethoxy-4',5'-dichloro-6-carboxyfluorescein (JOE), VIC® (Applied Biosystems), LC Red 640, LC Red 705, Yakima yellow, as well as derivatives thereof. Suitable quenchers of fluorescent dyes include, for example, Dabcyl, QSY7™ (Molecular Probes, Eugene, Oreg.) and the like.

Preferably, a means for determining the genotype of the at least five SNPs comprises at least ten labeled ASH probes, each probe comprising a self-quenched fluorescent oligonucleotide probe complementary to a specific allele of each of the at least five SNPs. Even more preferably, a means for determining the genotype of the at least five SNPs comprises at least ten labeled ASH probes, each probe comprising a self-quenched oligonucleotide probe comprising the 6-FAM fluorescent dye. In exemplary embodiments, ASH probes of the present disclosure are self-quenching TaqMan hydrolysis probes with 3'-minor groove binder (MGB).

Methods of designing and synthesizing a self-quenched ASH probes for determining the genotype of an SNP using a Real Time PCR reaction are known in the art. Probes may comprise a sequence of about 10, 15, 20, 25, 30, 35, 40, 45, 50 or more bases complementary to a specific allele of an SNP. Preferably, probes have a sequence of 10-30 bases, more preferably 10-25 bases complementary to a specific allele of an SNP. The melting temperature of a probe may be 50, 55, 60, 65, 70 or 75° C. Preferably, the melting temperature of a probe ranges between 60 and 75° C., more preferably between 65 and 70° C., and even more preferably between 65 and 69° C. The concentration of a probe in a PCR reaction may range from about 0.1 to about 1 µM, more preferably from about 0.2 to about 0.5 µM, and even more preferably about 0.25 µM.

In a preferred embodiment, a means for amplifying nucleic acid amplification products comprising SNPs and a means for determining the genotypes of the SNPs in the amplification products comprise a single disposable comprising reagents for amplifying the nucleic acid products using Real Time, hot-start PCR and for determining the genotype of the SNPs using ASH self-quenched oligonucleotide probes comprising the 6-FAM fluorescent dye.

Additional reagents for amplifying and determining the genotype are commonly known in the art and comprise nucleotides, buffering agents, detergents, and other ingredients. The amplification and detection method of the present invention may be performed with any of the standard master mixes and enzymes available. Additional reagents in a PCR reaction may generally comprise about 10-50 mM Tris-HCl pH 8.3, up to about 70 mM KCl, about 4-6 mM or higher MgCl$_2$, about 50-300 µM each of dATP, dCTP, dGTP and dTTP, more preferably 200 µM each of dATP, dCTP, dGTP and dTTP, gelatin or BSA to about 100 µg/ml, non-ionic detergents such as Tween-20 or Nonidet P-40 or Triton X-100 at about 0.05-0.10% v/v, and/or betaine at about 0.25 to about 1 M. An example of suitable buffer conditions may be found in Example 2. Advantageously, all the reagents required for amplifying and determining the genotype of an SNP can be provided in a dried composition for reconstitution before performing the assays. Preferably, each amplification and genotyping reaction described herein is provided in a dried composition.

As it will be apparent to those skilled in the art, amplification and detection methods, including Real Time PCR methods normally comprise the use of internal and/or parallel control reactions that confirm conditions for amplification and detection are desirable. For instance, positive amplification controls can give a detectable product derived from a component that is separate and distinct from the target. Detection of the positive control product indicates that amplification is viable and operative within the reaction chamber. Positive amplification controls which give no detectable product from the control components indicate conditions within the reaction chamber that do not allow amplification. Conversely, negative amplification controls do not give a detectable product in the absence of a nucleic acid template, and inhibition (or internal) amplification controls can determine if a lack of signal is due to the presence of an inhibitor in the PCR reaction. Preferably, means for amplifying and means for determining the genotypes further comprise a positive and an internal control that confirm conditions for amplification and detection.

Any positive and internal control reactions suitable for use with a means for amplifying and means for determining the genotypes of the present disclosure may be used. It will be recognized, that a positive and an internal amplification control in a means of the present disclosure will use methods and conditions compatible with the methods and conditions used for amplifying and genotyping a nucleic acid sequence of interest. As such, in addition to reagents for amplifying a control target nucleic acid molecule, an amplification control comprises a probe determining if the target nucleic acid sequence has been amplified.

A positive amplification control may comprise reagents for amplifying any nucleic acid fragment to determine that the PCR is working. Preferably, a positive amplification control suitable for an integrated system of the present disclosure comprises reagents for amplifying a human-specific nucleic acid sequence. As used herein, the term "human-specific" is used to describe a nucleic acid sequence that is present only in the human genome and absent in the genomes of other living organisms, including the most closely-related non-human primates such as chimpanzees. Advantageously, in addition to confirming conditions for amplification and detection, such a human-specific positive control confirms the presence of nucleic acid sequences of human origin when a nucleic acid sample isolated from provided biological material is used as a template.

Human-specific nucleic acid sequences that may be used in a positive amplification control of the present disclosure are known in the art. Preferably, a positive amplification control in a means for amplifying and means for determining of the present disclosure comprises reagents for amplifying and detecting a conserved region of the human-specific HS5 nucleic acid sequence (see for example Ueda et al. 1990 "Human-specific sequences: Isolation of species-specific DNA regions by genome subtraction." Genomics 8:7-12). Reagents for amplifying and detecting a conserved region of the human-specific HS5 nucleic acid sequence comprise one forward and one reverse primer wherein the forward primer hybridizes to a target site corresponding to nucleotides 2837 to 2960, preferably nucleotides 2937 to 2960 of SEQ ID NO: 22 or a complementary strand thereof and the reverse primer hybridizes to a target site corresponding to nucleotides 3009 to 3132, preferably nucleotides 3009 to 3032 of SEQ ID NO: 22 or a complementary strand thereof. A nucleic acid probe in this embodiment hybridizes to the amplification product at a target site corresponding to nucleotides 2961 to 3008, preferably nucleotides 2967 to 2981 of SEQ ID NO: 22. Preferably, the nucleic acid template for the positive control is the nucleic acid sample isolated from a provided biological material.

Additionally, amplification methods may further comprise inhibition controls. Inhibitors can be found in various specimens used for amplification, and these substances can interfere with amplification reactions by interacting directly with nucleic acids and blocking the activity of the polymerase or other amplification mixture components, thereby preventing target amplification. Examples of amplification inhibitors include bile salts in feces, heme in blood, and urea in urine. As such, inhibition (or internal) controls added directly to a nucleic acid sample are often used in order to detect inhibition associated with the sample or the processing method. In the presence of inhibitors strong enough to affect an amplification reaction, the efficiency of amplification will decrease resulting in a reduced or no positive signal associated with the inhibition control.

An amplification inhibition control generally comprises reagents for amplifying a known nucleic acid fragment from a nucleic acid template. Such an inhibition control normally comprises all the reagents required for performing a PCR reaction, including a nucleic acid template for amplification. Any nucleic acid amplification reaction known to be effective at amplifying a nucleic acid fragment from a provided nucleic acid template may be used as an inhibition control. Preferably, an inhibition control amplifies a portion of the *Daneo rerio βactin*1 nucleic acid sequence of a template of SEQ ID NO: 30. As such, reagents for an amplification inhibition control comprises a forward primer that hybridizes to a target site corresponding to nucleotides 1 to 75, preferably nucleotides 56 to 75 of SEQ ID NO: 30 or a complementary strand thereof and the reverse primer hybridizes to a target site corresponding to nucleotides 126 to 200, preferably nucleotides 126-145 of SEQ ID NO: 30 or a complementary strand thereof. A nucleic acid probe, in this embodiment with a concentration of 0.25 µM, where in the melting temperature of the probe is between 65° C. and 69° C. and it is labeled with a self-quenching 6-FAM dye, such that the probe hybridizes to the PCR product at a target site corresponding to nucleotides 76-125, preferably nucleotides 100-110 of SEQ ID NO: 30. In exemplary embodiments, an amplification inhibition control generally uses a synthetic nucleic acid template of SEQ ID NO: 30, wherein the template is used at a concentration of 20 fg.

As described above, a means for amplifying and determining the genotypes of the SNPs in the amplification products comprises a single reagent-containing disposable for amplifying nucleic acid amplification products and determining the genotypes of the SNPs in the amplification products. Such a disposable must be capable of supporting the amplification method and the detection method chosen for the means. When the amplification and detection method is Real Time PCR with fluorescently labeled ASH probes, the disposable is a PCR vessel capable of withstanding temperature changes and optically clear to determine genotype.

In preferred embodiments, a disposable comprises more than one slot for simultaneous amplification and identification of more than one nucleic acid amplification product. A disposable comprising more than one slot would also allow performing amplification controls as necessary and as described above. As such, a single-disposable may comprise 1, 2, 3, 4, 5, 6, 7, 8, 9, 10, 11, 12, 13, 14, 15, 16, 17, 18, 19, 20 or more slots for performing individual amplification and identification reactions. Preferably, a disposable comprises at least one slot comprising reagents for amplification of a human-specific control, at least one slot comprising reagents for amplification of an inhibition control, and at least five slots, wherein each of the five slots comprises reagents for amplifying a nucleic acid amplification product comprising a single SNP and for determining the genotype of the SNP using Real Time PCR. Even more preferred is a disposable comprising at least one slot comprising reagents for amplification of a human-specific control, at least one slot comprising reagents for amplification of an inhibition control, and at least ten slots, wherein each two slots of the at least ten slots comprises reagents for amplification of a single nucleic acid amplification product comprising a single SNP, wherein a first of each two slots comprises reagent for determining a first allele of the SNP, and a second of each two slots comprises reagent for determining a second allele of the SNP.

Preferred SNPs and the alleles of the SNPs are as described in Section IaA. Reagents for amplifying and determining the genotype of each SNP in Table A are provided below:

Reagents for amplifying a nucleic acid amplification product comprising the rs9866013 SNP comprise one forward and one reverse primer wherein the forward primer hybridizes to a target site within chromosome positions 59,502,477 to 59,502,597, most preferably positions 59,502,577 to 59,502,596 of SEQ ID NO: 1 or a complementary strand thereof, and the reverse primer hybridizes to a target site within chromosome positions 59,502,616 to 59,502,751, most preferably positions 59,502,633 to 59,502,651 of SEQ ID NO: 1 or a complementary strand thereof. Reagents for determining the genotype of the rs9866013 SNP comprise two nucleic acid probes that hybridize to the nucleic acid amplification product comprising the rs9866013 SNP at a target site within positions 59,502,598 to 59, 502, 630, most preferably positions 59,502,604 to 59, 502, 616 of SEQ ID NO: 1. Each of the two nucleic acid probes specifically hybridizes to either the C or T alleles of the rs9866013 SNP in the amplified nucleic acid fragment to determine the genotype of the rs9866013 SNP.

Reagents for amplifying a nucleic acid amplification product comprising the rs1019029 SNP comprise one forward and one reverse primer wherein the forward primer hybridizes to a target site within chromosome positions 13,854,497 to Ser. No. 13/854,647, most preferably positions 13,854,597 to 13,854,616 of SEQ ID NO: 2 or a complementary strand thereof, and the reverse primer hybridizes to a target site within chromosome positions 13,854,655 to 59,502,794, most preferably positions 13,854,672 to 13,854,694 of SEQ ID NO: 2 or a complementary strand thereof. Reagents for determining the genotype of the rs1019029 SNP comprise two nucleic acid probes that hybridize to the nucleic acid amplification product comprising the rs1019029 SNP at a target site within positions 13,854,635 to 13,854, 667, most preferably positions 13,854,641 to 13,854,658 of SEQ ID NO: 2. Each of the two nucleic acid probes specifically hybridizes to either the C or T alleles of the rs1019029 SNP in the amplified nucleic acid fragment to determine the genotype of the rs1019029 SNP.

Reagents for amplifying a nucleic acid amplification product comprising the rs2291395 SNP comprise one forward and one reverse primer wherein the forward primer hybridizes to a target site within chromosome positions 82,568,106 to 82,568,246, most preferably positions 82,568,206 to 82,568,225 of SEQ ID NO: 3 or a complementary strand thereof, and the reverse primer hybridizes to a target site within chromosome positions 82,568,265 to 82,568,393, most preferably positions 82,568,274 to 82,568,293 of SEQ ID NO: 3 or a complementary strand thereof. Reagents for determining the genotype of the rs2291395 SNP comprise two nucleic acid probes that hybridize to the nucleic acid amplification product comprising the rs2291395 SNP at a target site within positions 82,568,247 to 82,568,279, most preferably positions 82,568,257 to 82,568,272 of SEQ ID NO: 3. Each of the two nucleic acid probes specifically hybridizes to either the A or G alleles of the rs22913959 SNP in the amplified nucleic acid fragment to determine the genotype of the rs2291395 SNP.

Reagents for amplifying a nucleic acid amplification product comprising the rs12480506 SNP comprise one forward and one reverse primer wherein the forward primer hybridizes to a target site within chromosome positions 16,260,696 to Ser. No. 16/260,754, most preferably positions 16,260,735 to 16,260,754 of SEQ ID NO: 4 or a complementary strand thereof, and the reverse primer hybridizes to a target site within chromosome positions 16,260,788 to Ser. No. 16/260,915, most preferably positions 16,260,796 to 16,260,815 of SEQ ID NO: 4 or a complementary strand thereof. Reagents for determining the genotype of the rs12480506 SNP comprise two nucleic acid probes that hybridize to the nucleic acid amplification product comprising the rs12480506 SNP at a target site within positions 16,260,755 to Ser. No. 16/260,787, most preferably positions 16,260,760 to 16,260,778 of SEQ ID NO: 4. Each of the two nucleic acid probes specifically hybridizes to either the A or G alleles of the rs12480506 SNP in the amplified nucleic acid fragment to determine the genotype of the rs12480506 SNP.

Reagents for amplifying a nucleic acid amplification product comprising the rs315791 SNP comprise one forward and one reverse primer wherein the forward primer hybridizes to a target site within chromosome positions 170,308,767 to 170,308,898, most preferably positions 170,308,867 to 170,308,886 of SEQ ID NO: 5 or a complementary strand thereof, and the reverse primer hybridizes to a target site within chromosome positions 170,308,930 to 170,309,051, most preferably positions 170,308,930 to 170,308,951 of SEQ ID NO: 5 or a complementary strand thereof. Reagents for determining the genotype of the rs315791 SNP comprise two nucleic acid probes that hybridize to the nucleic acid amplification product comprising the rs315791 SNP at a target site within positions 170,308,899 to 170,308,933, most preferably positions 170,308,909 to 170,308,922 of SEQ ID NO: 5. Each of the two nucleic acid probes specifically hybridizes to either the A or G alleles of the rs315791 SNP in the amplified nucleic acid fragment to determine the genotype of the rs315791 SNP.

Reagents for amplifying a nucleic acid amplification product comprising the rs12997453 SNP comprise one forward and one reverse primer wherein the forward primer hybridizes to a target site within chromosome positions 181,548,369 to 181,548,528, most preferably positions 181,548,469 to 181,548,492 of SEQ ID NO: 6 or a complementary strand thereof, and the reverse primer hybridizes to a target site within chromosome positions 181,548,534 to 181,548,668, most preferably positions 181,548,549 to 181,548,568 of SEQ ID NO: 6 or a complementary strand thereof. Reagents for determining the genotype of the rs12997453 SNP comprise two nucleic acid probes that hybridize to the nucleic acid amplification product comprising the rs12997453 SNP at a target site within positions 181,548,516 to 181,548,548, most preferably positions 181,548,519 to 181,548,543 of SEQ ID NO: 6. Each of the two nucleic acid probes specifically hybridizes to either the A or G alleles of the rs12997453 SNP in the amplified nucleic acid fragment to determine the genotype of the rs12997453 SNP.

Reagents for amplifying a nucleic acid amplification product comprising the rs7041158 SNP comprise one forward and one reverse primer wherein the forward primer hybridizes to a target site within chromosome positions 27,985,803 to 27,985,936, most preferably positions 27,985,903 to 27,985,924 of SEQ ID NO: 7 or a complementary strand thereof, and the reverse primer hybridizes to a target site within chromosome positions 27,985,942 to 27,986,083, most preferably positions 27,985,961 to 27,985,983 of SEQ ID NO: 7 or a complementary strand thereof. Reagents for determining the genotype of the rs7041158 SNP comprise two nucleic acid probes that hybridize to the nucleic acid amplification product comprising the rs7041158 SNP at a target site within positions 27,985,924 to 27,985,956, most preferably positions 27,985,929 to 27,985,950 of SEQ ID NO: 7. Each of the two nucleic acid probes specifically hybridizes to either the C or T alleles of the rs7041158 SNP in the amplified nucleic acid fragment to determine the genotype of the rs7041158 SNP.

Reagents for amplifying a nucleic acid amplification product comprising the rs2272998 SNP comprise one forward and one reverse primer wherein the forward primer hybridizes to a target site within chromosome positions 148,440,157 to 148,440,682, most preferably positions 148,440,257 to 148,440,279 of SEQ ID NO: 8 or a complementary strand thereof, and the reverse primer hybridizes to a target site within chromosome positions 148,440,324 to 148,440,464, most preferably positions 148,440,343 to 148,440,364 of SEQ ID NO: 8 or a complementary strand thereof. Reagents for determining the genotype of the rs2272998 SNP comprise three nucleic acid probes that hybridize to the nucleic acid amplification product comprising the rs2272998 SNP at a target site within positions 148,440,304 to 148,440,336, most preferably positions 148,440,314 to 148,440,329 of SEQ ID NO: 8. Each of the three nucleic acid probes specifically hybridizes to either the C, G, or T alleles of the rs2272998 SNP in the amplified nucleic acid fragment to determine the genotype of the rs2272998 SNP.

Reagents for amplifying a nucleic acid amplification product comprising the rs13134862 SNP comprise one forward and one reverse primer wherein the forward primer hybridizes to a target site within chromosome positions 75,500,543 to 75,500,682, most preferably positions 75,500,643 to 75,500,664 of SEQ ID NO: 9 or a complementary strand thereof, and the reverse primer hybridizes to a target site within chromosome positions 75,500,690 to 75,500,831, most preferably positions 75,500,708 to 75,500,731 of SEQ ID NO: 9 or a complementary strand thereof. Reagents for determining the genotype of the rs13134862 SNP comprise two nucleic acid probes that hybridize to the nucleic acid amplification product comprising the rs13134862 SNP at a target site within positions 75,500,670 to 75,500,702, most preferably positions 75,500,677 to 75,500,698 of SEQ ID NO: 9. Each of the two nucleic acid probes specifically hybridizes to either the A or G alleles of the rs13134862 SNP in the amplified nucleic acid fragment to determine the genotype of the rs13134862 SNP.

Reagents for amplifying a nucleic acid amplification product comprising the rs3780962 SNP comprise one forward and one reverse primer wherein the forward primer hybridizes to a target site within chromosome positions 17,151,203 to Ser. No. 17/151,343, most preferably positions 17,151,303 to 17,151,323 of SEQ ID NO: 10 or a complementary strand thereof, and the reverse primer hybridizes to a target site within chromosome positions 17,151,351 to Ser. No. 17/151,513, most preferably positions 17,151,394 to 17,151,413 of SEQ ID NO: 10 or a complementary strand thereof. Reagents for determining the genotype of the rs3780962 SNP comprise two nucleic acid probes that hybridize to the nucleic acid amplification product comprising the rs13134862 SNP at a target site within positions 17,151,331 to Ser. No. 17/151,363, most preferably positions 17,151,339 to 17,151,354 of SEQ ID NO: 10. Each of the two nucleic acid probes specifically hybridizes to either the C or T alleles of the rs3780962 SNP in the amplified nucleic acid fragment to determine the genotype of the rs3780962 SNP.

Reagents for amplifying a nucleic acid amplification product comprising the rs433342 SNP comprise one forward and one reverse primer wherein the forward primer hybridizes to a target site within chromosome positions 17,890,226 to Ser. No. 17/890,363, most preferably positions 17,890,326 to 17,890,348 of SEQ ID NO: 11 or a complementary strand thereof, and the reverse primer hybridizes to a target site within chromosome positions 17,890,371 to Ser. No. 17/890,503, most preferably positions 17,890,385 to 17,890,403 of SEQ ID NO: 11 or a complementary strand thereof. Reagents for determining the genotype of the rs433342 SNP comprise three nucleic acid probes that hybridize to the nucleic acid amplification product comprising the rs433342 SNP at a target site within positions 17,890,351 to Ser. No. 17/890,383, most preferably positions 17,890,359 to 17,890,373 of SEQ ID NO: 11. Each of the three nucleic acid probes specifically hybridizes to either the A, C, or G alleles of the rs433342 SNP in the amplified nucleic acid fragment to determine the genotype of the rs433342 SNP.

Reagents for amplifying a nucleic acid amplification product comprising the rs9546538 SNP comprise one forward and one reverse primer wherein the forward primer hybridizes to a target site within chromosome positions 83,882,458 to 83,882,596, most preferably positions 83,882,558 to 83,882,577 of SEQ ID NO: 12 or a complementary strand thereof, and the reverse primer hybridizes to a target site within chromosome positions 83,882,604 to 83,882,745, most preferably positions 83,882,626 to 83,882,645 of SEQ ID NO: 12 or a complementary strand thereof. Reagents for determining the genotype of the rs9546538 SNP comprise two nucleic acid probes that hybridize to the nucleic acid amplification product comprising the rs9546538 SNP at a target site within positions 83,882,584 to 83,882,616, most preferably positions 83,882,589 to 83,882,5608 of SEQ ID NO: 12. Each of the two nucleic acid probes specifically hybridizes to either the C or T alleles of the rs9546538 SNP in the amplified nucleic acid fragment to determine the genotype of the rs9546538 SNP.

Reagents for amplifying a nucleic acid amplification product comprising the rs16891982 SNP comprise one forward and one reverse primer wherein the forward primer hybridizes to a target site within chromosome positions 33,951,453 to 33,951,584, most preferably positions 33,951,553 to 33,951,576 of SEQ ID NO: 13 or a complementary strand thereof, and the reverse primer hybridizes to a target site within chromosome positions 33,951,592 to 33,951,752, most preferably positions 33,951,633 to 33,951,652 of SEQ ID NO: 13 or a complementary strand thereof. Reagents for determining the genotype of the rs9546538 SNP comprise two nucleic acid probes that hybridize to the nucleic acid amplification product comprising the rs16891982 SNP at a target site within positions 33,951,572 to 33,951,604, most preferably positions 33,951,580 to 33,951,593 of SEQ ID NO: 13. Each of the two nucleic acid probes specifically hybridizes to either the C or G alleles of the rs16891982 SNP in the amplified nucleic acid fragment to determine the genotype of the rs16891982 SNP.

Reagents for amplifying a nucleic acid amplification product comprising the rs310644 SNP comprise one forward and one reverse primer wherein the forward primer hybridizes to a target site within chromosome positions 63,527,913 to 63,528,147 most preferably positions 63,528,113 to 63,528,135 of SEQ ID NO: 14 or a complementary strand thereof, and the reverse primer hybridizes to a target site within chromosome positions 63,528,155 to 63,528,319, most preferably positions 63,528,197 to 63,528,219 of SEQ ID NO: 14 or a complementary strand thereof. Reagents for determining the genotype of the rs310644 SNP comprise two nucleic acid probes that hybridize to the nucleic acid amplification product comprising the rs310644 SNP at a target site within positions 63,528,135 to 63,528,167, most preferably positions 63,528,129 to 63,528,161 of SEQ ID NO: 14. Each of the two nucleic acid probes specifically hybridizes to either the A or G alleles of the rs310644 SNP in the amplified nucleic acid fragment to determine the genotype of the rs310644 SNP.

Reagents for amplifying a nucleic acid amplification product comprising the rs1426654 SNP comprise one forward and one reverse primer wherein the forward primer hybridizes to a target site within chromosome positions 48,134,158 to 48,134,283, most preferably positions 48,134,258 to 48,134,277 of SEQ ID NO: 15 or a complementary strand thereof, and the reverse primer hybridizes to a target site within chromosome positions 48,134,291 to 48,134,438, most preferably positions 48,134,315 to 48,134,338 of SEQ ID NO: 15 or a complementary strand thereof. Reagents for determining the genotype of the rs1426654 SNP comprise two nucleic acid probes that hybridize to the nucleic acid amplification product comprising the rs1426654 SNP at a target site within positions 48,134,271 to 48,134,303, most preferably positions 48,134,279 to 48,134,292 of SEQ ID NO: 15. Each of the two nucleic acid probes specifically hybridizes to either the A or G alleles of the rs1426654 SNP in the amplified nucleic acid fragment to determine the genotype of the rs1426654 SNP.

Reagents for amplifying a nucleic acid amplification product comprising the rs3827760 SNP comprise one forward and one reverse primer wherein the forward primer hybridizes to a target site within chromosome positions 108,896,987 to 108,897,141, most preferably positions 108,897,087 to 108,897,106 of SEQ ID NO: 16 or a complementary strand thereof, and the reverse primer hybridizes to a target site within chromosome positions 108,897,149 to 108,897,279, most preferably positions 108,897,160 to 108,897,179 of SEQ ID NO: 16 or a complementary strand thereof. Reagents for determining the genotype of the rs3827760 SNP comprise two nucleic acid probes that hybridize to the nucleic acid amplification product comprising the rs3827760 SNP at a target site within positions 108,897,129 to 108,897,161, most preferably positions 108,897,141 to 108,897,157 of SEQ ID NO: 16. Each of the two nucleic acid probes specifically hybridizes to either the C or T alleles of the rs3827760 SNP in the amplified nucleic acid fragment to determine the genotype of the rs3827760 SNP.

Reagents for amplifying a nucleic acid amplification product comprising the rs4891825 SNP comprise one forward and one reverse primer wherein the forward primer hybridizes to a target site within chromosome positions 70,200,250 to 70,200,423, most preferably positions 70,200,350 to 70,200,369 of SEQ ID NO: 17 or a complementary strand thereof, and the reverse primer hybridizes to a target site within chromosome positions 70,200,431 to 70,200,571, most preferably positions 70,200,452 to 70,200,471 of SEQ ID NO: 17 or a complementary strand thereof. Reagents for determining the genotype of the rs4891825 SNP comprise two nucleic acid probes that hybridize to the nucleic acid amplification product comprising the rs4891825 SNP at a target site within positions 70,200,411 to 70,200,443, most preferably positions 70,200,420 to 70,200,436 of SEQ ID NO: 17. Each of the two nucleic acid probes specifically hybridizes to either the A or G alleles of the rs4891825 SNP in the amplified nucleic acid fragment to determine the genotype of the rs4891825 SNP.

Reagents for amplifying a nucleic acid amplification product comprising the rs4918664 SNP comprise one forward and one reverse primer wherein the forward primer hybridizes to a target site within chromosome positions 93,161,152 to 93,161,304, most preferably positions 93,161,252 to 93,161,271 of SEQ ID NO: 18 or a complementary strand thereof, and the reverse primer hybridizes to a target site within chromosome positions 93,161,312 to 93,161,457, most preferably positions 93,161,338 to 93,161,357 of SEQ ID NO: 18 or a complementary strand thereof. Reagents for determining the genotype of the rs4918664 SNP comprise two nucleic acid probes that hybridize to the nucleic acid amplification product comprising the rs4918664 SNP at a target site within positions 93,161,292 to 93,161,3324, most preferably positions 93,161,302 to 93,161,319 of SEQ ID NO: 18. Each of the two nucleic acid probes specifically hybridizes to either the A or G alleles of the rs4918664 SNP in the amplified nucleic acid fragment to determine the genotype of the rs4918664 SNP.

Reagents for amplifying a nucleic acid amplification product comprising the rs10497191 SNP comprise one forward and one reverse primer wherein the forward primer hybridizes to a target site within chromosome positions 157,810,563 to 157,810,701, most preferably positions 157,810,663 to 157,810,682 of SEQ ID NO: 19 or a complementary strand thereof, and the reverse primer hybridizes to a target site within chromosome positions 157,810,709 to 157,810,873, most preferably positions 157,810,753 to 157,810,773 of SEQ ID NO: 19 or a complementary strand thereof. Reagents for determining the genotype of the rs10497191 SNP comprise two nucleic acid probes that hybridize to the nucleic acid amplification product comprising the rs10497191 SNP at a target site within positions 157,810,689 to 157,810,721, most preferably positions 157,810,696 to 157,810,713 of SEQ ID NO: 19. Each of the two nucleic acid probes specifically hybridizes to either the C or T alleles of the rs10497191 SNP in the amplified nucleic acid fragment to determine the genotype of the rs10497191 SNP.

Reagents for amplifying a nucleic acid amplification product comprising the rs12913832 SNP comprise one forward and one reverse primer wherein the forward primer hybridizes to a target site within chromosome positions 28,120,321 to 28,120,456, most preferably positions 28,120,421 to 28,120,441 of SEQ ID NO: 20 or a complementary strand thereof, and the reverse primer hybridizes to a target site within chromosome positions 28,120,464 to 28,120,606, most preferably positions 28,120,488 to 28,120,506 of SEQ ID NO: 20 or a complementary strand thereof. Reagents for determining the genotype of the rs12913832 SNP comprise two nucleic acid probes that hybridize to the nucleic acid amplification product comprising the rs12913832 SNP at a target site within positions 28,120,444 to 28,120,486 most preferably positions 28,120,466 to 28,120,484 of SEQ ID NO: 20. Each of the two nucleic acid probes specifically hybridizes to either the A or G alleles of the rs12913832 SNP in the amplified nucleic acid fragment to determine the genotype of the rs12913832 SNP.

Reagents for amplifying a nucleic acid amplification product comprising the rs1876482 SNP comprise one forward and one reverse primer wherein the forward primer hybridizes to a target site within chromosome positions 17,181,166 to Ser. No. 17/181,297, most preferably positions 17,181,266 to 17,181,285 of SEQ ID NO: 21 or a complementary strand thereof, and the reverse primer hybridizes to a target site within chromosome positions 17,181,305 to Ser. No. 17/181,448, most preferably positions 17,181,329 to 17,181,348 of SEQ ID NO: 21 or a complementary strand thereof. Reagents for determining the genotype of the rs1876482 SNP comprise two nucleic acid probes that hybridize to the nucleic acid amplification product comprising the rs1876482 SNP at a target site within positions 17,181,285 to Ser. No. 17/181,317, most preferably positions 17,181,293 to 17,181,310 of SEQ ID NO: 21. Each of the two nucleic acid probes specifically hybridizes to either the C or T alleles of the rs1876482 SNP in the amplified nucleic acid fragment to determine the genotype of the rs1876482 SNP.

In an exemplary embodiment, a reagent-containing disposable comprises one slot comprising reagents for amplification of the HS5 human-specific control of SEQ ID NO: 22, one slot comprising reagents for an inhibition control, the inhibition control comprising the amplification of a portion of the nucleic acid sequence of SEQ ID NO: 30, one slot comprising reagents for determining if the allele of the rs9866013 SNP is C, one slots for determining if the genotype of the rs9866013 SNP is T, one slot comprising reagents for determining if the allele of the rs1019029 SNP is C, one slots for determining if the genotype of the rs1019029 SNP is T, one slot comprising reagents for determining if the allele of the rs2291395 SNP is A, one slots for determining if the genotype of the rs2291395 SNP is G, one slot comprising reagents for determining if the allele of the rs12480506 SNP is A, one slots for determining if the genotype of the rs12480506 SNP is G, one slot comprising reagents for determining if the allele of the rs315791 SNP is A, one slots for determining if the genotype of the rs315791 SNP is C.

In preferred embodiments, when an instrument for nucleic acid amplification and detection of the present disclosure is the RAZOR® EX (BioFire Defense, Salt Lake City, Utah), a means for amplifying and determining the genotypes of the SNPs in the amplification products comprises a disposable pouch for use with the RAZOR® EX instrument. A RAZOR® EX disposable pouch comprises twelve slots for amplifying and determining the genotypes of SNPs and may be as described in U.S. Patent Publication No. 2013/0171045, the disclosure of which is incorporated herein in its entirety.

In exemplary embodiments, when a disposable is the RAZOR® EX disposable pouch, a means for amplifying and determining the genotypes of SNPs comprises the RAZOR® EX disposable pouch comprising freeze-dried reagents for amplifying nucleic acid amplification products comprising the rs9866013, rs1019029, rs2291395, rs12480506, rs315791SNPs, an determining the genotypes of the SNPs, and may comprise a layout as described in Table B.

TABLE B

Layout of the SNP assays in the disposable pouch for use with the RAZOR EX instrument

| Slot | SNP/Control | Allele |
|---|---|---|
| 1 | rs9866013 | C |
| 2 | rs9866013 | T |
| 3 | rs1019029 | C |
| 4 | rs1019029 | T |
| 5 | rs2291395 | A |
| 6 | rs2291395 | G |
| 7 | rs12480506 | A |
| 8 | rs12480506 | G |
| 9 | rs315791 | A |
| 10 | rs315791 | C |
| 11 | HS5 Human-Specific Control | |
| 12 | βactin1 inhibition Control | |

It will be recognized that when a disposable is the RAZOR® EX disposable pouch, a reagent kit further comprises a means for introducing a nucleic acid sample into the pouch. Preferably, a means for introducing a nucleic acid sample into the RAZOR® EX disposable pouch is a 3 ml blunt tipped plastic syringe.

b. Instrument for Nucleic Acid Amplification and Detection

A self-contained system of the present disclosure comprises an instrument for nucleic acid amplification and detection. As described above, amplification of nucleic acids comprises reaction mixtures be subjected to repeated rounds of heating and cooling. All commercially available instruments for nucleic acid amplification operate by changing the temperature of the environment of a reaction vessel, either by heating and cooling the environment, or by robotically moving the samples between environments. As such, an instrument for nucleic acid amplification and detection of the present disclosure is capable of subjecting an amplification reaction to repeated rounds of heating and cooling to perform the amplification reaction. Additionally, an instrument for nucleic acid amplification and detection of the present disclosure is capable of monitoring the production of a signal in real time during amplification to generate SNP allelic data. Monitoring amplification in real-time greatly reduces the amount of sample transfer required between amplification reaction and observation of results. Preferably an instrument of the present disclosure is capable of monitoring fluorescence.

Any commercially available real-time nucleic acid amplification instrument may be used in the present disclosure, provided the instrument is compatible with a reagent kit described in Section IaB, and provided the instrument can be used in austere field-forward conditions as described above.

Preferably, an instrument for nucleic acid amplification and detection of the present disclosure is capable of Real Time PCR. Also preferred, is an instrument that can generate dependable results in a short amount of time, is compact, lightweight, and easy to operate by a minimally trained technician under extreme conditions. Preferably, an instrument is battery operated for operation in remote areas. Also preferred, is an instrument comprising a bar code reader to facilitate operation of the instrument and to provide means for maintaining the chain of custody of a collected and analyzed specimen. For instance, a bar code reader may be used to scan a bar code imprinted on a reagent kit, thereby activating an operations protocol suitable for the reagent kit. In exemplary embodiments, an instrument of the present disclosure is the RAZOR® EX instrument (BioFire Defense, Salt Lake City, Utah).

II. Methods

In another aspect, a method of constructing a nucleic acid profile of a human individual is provided. A method comprises providing a biological material from a human individual and providing a self-contained system constructing a nucleic acid profile of a human individual described in Section I. The self-contained system is then used to isolate a nucleic acid sample from the provided biological material, and amplifying at least five nucleic acid amplification products from the nucleic acid sample, wherein each amplification product comprises a single nucleotide polymorphism (SNP). The self-contained system is also used determine the genotypes of the SNPs in the one or more amplification products, thereby constructing the nucleic acid profile of the human individual.

Advantageously, a method of the present disclosure is capable of constructing a nucleic acid profile of a human individual in austere filed-forward conditions and can be performed by minimally-trained individuals while still maintaining accuracy, sterility, and sample integrity. Additionally, methods of the present disclosure are capable of generating results rapidly to provide actionable data in near-real-time in clinical, forensic, or other settings.

Methods of providing a biological material from a human individual are known in the art. Preferably, a biological material is provided by swabbing the human individual, or a physical surface suspected of comprising biological material from a human individual using a swab comprising a point of breakage for collecting a biological material.

A nucleic acid sample is isolated from the provided biological material using the means provided with the reagent kit of the self-contained system. When the preferred means for isolating a nucleic acid sample from a provided biological material comprises a 5 ml vial comprising 600 µl NaOH at pH of 12.5 and zirconium beads, and a double barreled syringe comprising 1780 µl water in a first barrel and 120 µl neutralization buffer in a second barrel, a nucleic acid sample is isolated by breaking the swab tip comprising the biological material into the 5 ml vial and shaking the vial for a period ranging from about 1 second to about 1 minute, preferably for about 10 to 30 seconds, preferably for about 15 seconds. The contents of the double barreled syringe may then be added to the 5 ml vial, thereby isolating a nucleic acid sample.

Nucleic acid amplification products comprising SNPs may then be amplified using the means of amplification provided with the reagent kit of the self-contained system, and the genotypes of the SNPs may be determined using the means for determining genotypes provided with the reagent kit. As described above, a means for amplifying nucleic acid amplification products comprising SNPs and a means for determining the genotypes of the SNPs in the amplification products comprise reagents for use in methods for amplifying and genotyping that are compatible and can be performed simultaneously in a single disposable. As such, a preferred method comprises simultaneously amplifying and genotyping in a single disposable provided in a reagent kit of the self-contained system. When the means for amplifying and determining the genotypes of the SNPs in the amplification products comprises a disposable pouch comprising freeze-dried reagents for use with the RAZOR® EX instrument, a 3 ml syringe may be used to transfer the isolated nucleic acid sample into the disposable pouch, thereby hydrating the reagents in all 12 slots of the pouch. Plungers on the pouch are then depressed to force the reagents into the pouch as described by the manufacturer. Preferably, the RAZOR® EX disposable pouch comprises freeze-dried reagents for amplifying nucleic acid amplification products comprising the rs9866013, rs1019029, rs2291395, rs12480506, rs315791SNPs, and determining the genotypes of the SNPs.

The prepared pouch is then inserted into the RAZOR® EX instrument to amplify and determine the genotype. Preferably, a linear bar code on the RAZOR® EX disposable pouch is scanned using the integrated bar code scanner of the RAZOR® EX instrument to activate a thermalcycling protocol appropriate for the kit. Preferably, the RAZOR® EX disposable pouch comprises freeze-dried reagents for amplifying nucleic acid amplification products comprising the rs9866013, rs1019029, rs2291395, rs12480506, rs315791 SNPs, and determining the genotypes of the SNPs, and the thermalcycling protocol is as described in Table 7.

A nucleic acid profile of the human individual may then be constructed by using the SNP allelic data produced by the real-time amplification of the aforementioned thermal cycler. For example, when the genotypes of the rs9866013, rs1019029, rs2291395, rs12480506, rs315791SNPs are determined, an exemplary nucleic acid profile of the human individual may comprise two C alleles for rs9866013, one T allele and one C allele for rs1019029, two A alleles for rs2291395, one A allele and one G allele for rs12480506, and two A alleles for rs315791.

In some preferred embodiments, SNP allelic data of the nucleic acid profile generated as described above may be used to create a simplified pattern representing the nucleic acid profile. Preferably, SNP allelic data may be converted to binary code wherein each genotype of an SNP is assigned one of the values of the binary codes. Non-limiting examples of binary codes suitable for creating a simplified pattern representing the nucleic acid profile may include symbolic codes such as + and −, colorimetric codes such as red and green, and numerical codes such as 0 and 1. For instance, if the code is + and −, the alleles of each of the rs9866013, rs1019029, rs2291395, rs12480506, rs315791 SNPs may be assigned the values as shown in Table C. Using this assignation, an exemplary nucleic acid profile of a human individual that comprises two C alleles for rs9866013, one T allele and one C allele for rs1019029, two A alleles for rs2291395, one A allele and one G allele for rs12480506, and two C alleles for rs315791 would be represented as the simplified pattern: (+,−)(+,+)(+,−)(+,+)(−,+)(+)(+).

TABLE C

Conversion of allelic data to binary data

| SNP/Control | Genotype | Binary value |
|---|---|---|
| | | Slots 1 & 2 |
| rs9866013 | CC | +, − |
| | TT | −, + |
| | CT | +, + |
| | | Slots 3 & 4 |
| rs1019029 | CC | +, − |
| | TT | −, + |
| | CT | +, + |
| | | Slots 5 & 6 |
| rs2291395 | AA | +, − |
| | GG | −, + |
| | AG | +, + |
| | | Slots 7 & 8 |
| rs12480506 | AA | +, − |
| | GG | −, + |
| | AG | +, + |
| | | Slots 9 & 10 |
| rs315791 | AA | +, − |
| | CC | −, + |
| | AC | +, + |
| | | Slot 11 |
| Human-Specific Control | Positive | + |
| | Negative | − |
| | | Slot 12 |
| Inhibition Control | Positive | + |

In a preferred alternative of these embodiments, SNP allelic data is converted to a symbolic code. In another preferred alternative of these embodiments, SNP allelic data is converted to a colorimetric code.

In yet another aspect, a method of identifying an unidentified human individual is provided. The method comprises constructing a nucleic acid profile of the human individual as described above. In preferred embodiments, SNP allelic data of the nucleic acid profile are used to create a simplified pattern representing the nucleic acid profile. Preferably, SNP allelic data are converted to a code wherein each allele of an SNP is assigned one of the values of the code as described above.

The method further comprises using the constructed nucleic acid profile to compare to a database of nucleic acid profiles from referenced individuals to identify the human. It will be recognized that if the constructed nucleic acid profile is a simplified pattern representing the nucleic acid profile, the nucleic acid profiles in the database are also simplified pattern representing the nucleic acid profiles in the database.

Definitions

As used herein, the term "SNP" is an acronym for Single Nucleotide Polymorphism, and refers to when a single nucleotide is replaced with another.

The term "oligonucleotide" as used herein is defined as a molecule comprised of two or more deoxyribonucleotides or ribonucleotides, preferably more than three. The exact size will depend on many factors, which in turn depends on the ultimate function or use of the oligonucleotide. The oligonucleotide may be generated in any manner, including chemical synthesis, DNA replication, reverse transcription, or a combination thereof.

As used herein, "amplifying" refers to the process of synthesizing nucleic acid molecules that are complementary to one or both strands of a template nucleic acid molecule. Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme, and an appropriate buffer and/or co-factors for optimal activity of the polymerase enzyme (e.g., $MgCl_2$ and/or KCl).

The term "PCR" is an acronym for polymerase chain reaction and refers to a method of exponentially amplifying a fragment of DNA to facilitate detection.

The term "primer set" refers to a set of primers, viz. nucleic acid strands and related synthetic primer having appropriately similar or equivalent functionality.

The term "nucleotide" refers to the purine, & pyrimidine ribonucleotides which are the structural units of DNA, RNA, and cofactors.

As used herein, the term "3'-end" means the end of a nucleic acid sequence where the 3' position of the terminal residue is not bound by a nucleotide.

As used herein, the term "5'-end" means the end of a nucleic acid sequence where the 5' position of the terminal residue is not bound by a nucleotide.

As used herein, the phrase "amplifying [a nucleic acid molecule]" means to increase the number of copies of a nucleic acid molecule. The resulting amplification products may be called "amplicons."

As used herein, the term "complementary" means binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one single-stranded (ss) DNA molecule can bond to 3'-TAGC-5' of another ssDNA to form a double-stranded (ds) DNA. In this example, the sequence 5'-ATCG-3' is the reverse complement of 3'-TAGC-5'. Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

As used herein, the term "label" means an agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part of Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

As used herein, the term "nucleic acid molecule" means a deoxyribonucleotide or ribonucleotide polymer, which can include analogues of natural nucleotides that hybridize to nucleic acid molecules in a manner similar to naturally occurring nucleotides. In a particular example, a nucleic acid molecule is a ssDNA or RNA molecule, such as a primer. In another particular example, a nucleic acid molecule is a ds DNA, such as a target nucleic acid. The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties and modified phosphate backbones, for example as described in U.S. Pat. No. 5,866,336 to Nazarenko et al. Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethyl-aminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, methoxyaminomethyl-2-thiouracil, beta-D-mannosylqueosine, 51-methoxycarboxymethylura-cil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methyl-2-thiouracil, 3-(3-amino-3-N-2-carboxypropyl) uracil, and 2,6-diaminopurine.

As used herein, the term "primer" means an oligonucleotide, which, when hybridized to its complementary nucleic acid targets, allows strand extension by a polymerase. Primer pairs bracketing an amplicon can be used for amplification of a nucleic acid sequence, for example by PCR, TMA or other nucleic-acid amplification methods.

As used herein, the term "quenching of fluorescence" means a reduction of fluorescence. For example, quenching of a fluorophore's fluorescence on a sequence occurs when a quencher molecule (such as guanosine) is present in sufficient proximity to the fluorophore that it reduces the fluorescence signal of the reporter molecule during complementary strand synthesis.

As used herein, the term "real-time PCR" means a method for detecting and measuring products generated during each cycle of a PCR, which are proportionate to the amount of nucleic acid target prior to the start of PCR. The information obtained, such as an amplification curve, can be used to quantitate the initial amounts of nucleic acid target.

As used herein, the term "recombinant nucleic acid molecule" is one that has a sequence that is not naturally occurring or has a sequence that is made by an artificial combination of two otherwise separated segments of sequence. This artificial combination can be accomplished, for example, by chemical synthesis or by the artificial manipulation of isolated segments of nucleic acid molecules, for example, by genetic engineering techniques.

As used herein, the term "signal" means an indicator, such as a detectable physical quantity from which information can be obtained. In one example, a label emits a signal capable of detection, such as a fluorescent signal.

As used herein, the term "upstream" and "downstream" refer to a relative position in DNA or RNA. Each strand of DNA or RNA has a 5'-end and a 3'-end, so named for the carbons on the deoxyribose ring. Relative to the position on the strand, downstream is the region towards the 3'-end of the strand, and upstream is the region towards the 5'-end of the strand. Since DNA strands run in opposite directions, downstream on one strand is upstream on the other strand.

When introducing elements of the present disclosure or the embodiments(s) thereof, the articles "a," "an," "the," and "said" are intended to mean that there are one or more of the elements. The terms "comprising," "including," and "having" are intended to be inclusive and mean that there may be additional elements other than the listed elements.

Although the disclosure described herein is susceptible to various modifications and alternative iterations, specific embodiments thereof have been described in greater detail above. It should be understood, however, that the detailed description is not intended to limit the disclosure to the specific embodiments disclosed. Rather, it should be understood that the disclosure is intended to cover all modifications, equivalents, and alternatives falling within the spirit and scope of the disclosure as defined by the claim language.

EXAMPLES

The following examples illustrate various embodiments of the invention.

Introduction for Examples 1-9

The Examples presented herein describe the validation of a human identification system that may be used in field forward positions. The identification system in the examples below uses the RAZOR® EX BioDetection System manufactured by BioFire™ Defense and TaqMane MGB hydrolysis probes in allelic discrimination assays. The human identification system is a real-time polymerase chain reaction (PCR) assay that targets bi-allelic single nucleotide polymorphisms for individual identification (IISNPs). The RAZOR® EX Human Identification System performs rapid presumptive identification of individuals with a power of discrimination of 98.3%.

The human identification system described herein contains primers and fluorogenic probes that bind to and amplify five IISNPs. Single nucleotide polymorphisms (SNPs) are single base sequence variations between individuals at particular points in the genome. Their size and bi-allelic nature make them ideal candidates for rapid, short amplicon real-time PCR assays. IISNPs are SNPs that are useful for human identification due to high heterozygosity (>0.4) and low genetic variance among populations ($F_{ST}$<0.06). High heterozygosity maximizes the information at each SNP, and low $F_{ST}$ minimizes chance variation between populations. The human identification system also contains a human-specific control and an inhibition control. The human-specific control targets a human-specific gene region and indicates the presence of human DNA. The inhibition control consists of a fixed quantity of non-human synthetic DNA template and a primer and probe set specific for the template. Failure of the inhibition control is indicative of the presence of a PCR inhibitor in the sample.

Methods for Examples 1-9

Genetic Markers: SNPs, Human-Specific Control, and Inhibition Control

The human identification system described in these Examples uses five SNPs in real-time PCR assays to perform rapid identification of individuals. Additionally, one human-specific gene region is used as a positive control to detect human DNA and a non-human gene region is used to assess PCR inhibition. The characterization of the SNPs and two gene regions used in this system are described herein.

A. IISNPs

The SNPs selected for inclusion in the human identification system are bi-allelic, meaning that they have two possible alleles and three possible genotypes. Individuals inherit one allele from each of their parents. The five SNPs selected for inclusion in this system include rs9866013, rs1019029, rs2291395, rs12480506, and rs315791 (Table 1). These SNPs have been well characterized as suitable for human identification [1-4].

TABLE 1

Genomic locations and primer and probe sequence information for SNPs included in the RAZOR EX Human Identification System

| SNP | Chr. | Chr. Position | Forward Primer | Reverse Primer | Allele | TaqMan Probe |
|---|---|---|---|---|---|---|
| rs9866013 | 3 | 59502614 | SEQ ID NO: 31; TGCAAAG TGGGTTG TTTCTC | SEQ ID NO: 32; TGCAAAT GAACTCC CATCC | C | SEQ ID NO: 33; ACAGGGCAGGCAA |
| | | | | | T | SEQ ID NO: 34; CCCCTATTTACCTGCC |
| rs1019029 | 7 | 13854651 | SEQ ID NO: 35; GCCTACT CAAGCAG AGATAACG | SEQ ID NO: 36; GTGGCTT CATTTTC AACAGG | C | SEQ ID NO: 37; CTAAATGCCTAGTCTGCT |
| | | | | | T | SEQ ID NO: 38; CAGACTAGACATTTAGC |
| rs2291395 | 17 | 82568263 | SEQ ID NO: 39; AGGCTTT GTAGCCT TGAAGC | SEQ ID NO: 40; GACAGGC AGGTGAG TGACAG | A | SEQ ID NO: 41; CCCTCAATGTCACCTG |
| | | | | | G | SEQ ID NO: 42; CCCTCAGTGTCACCT |
| rs12480506 | 20 | 16260771 | SEQ ID NO: 43; GGGAGGA GACAGCT TCTTGA | SEQ ID NO: 44; CCAAAAT CCATGTT GTGAGC | A | SEQ ID NO: 45; TTCGTGTCCCTATGCTAG T |
| | | | | | G | SEQ ID NO: 46; TCGTGTCCCTGTGCTA |
| rs315791 | 5 | 170308916 | SEQ ID NO: 47; TACCAGG GGTGTTT CCCTTA | SEQ ID NO: 48; TTGTTAA TTTCTGT CTGCCACA | A | SEQ ID NO: 49; CATAGGCAAGTTTC |
| | | | | | C | SEQ ID NO: 50; CATAGGCCAGTTTCAT |

B. Human-Specific Control DNA Region

A human-specific DNA sequence characterized by the genome subtraction method and presented as HS5 [5, 6] was utilized as the marker region for development of a human-specific control assay. The proposed sequence allowed for a 3'-minor groove binder (MGB) probe-based control assay to be developed in a conserved region of the HS5 sequence. The genomic region utilized for TaqMan design was queried in NCBI utilizing the Basic Local Alignment Search Tool (BLAST) to ensure specificity to the targeted genomic region and the human species. The search demonstrated a 100% identical coverage of the HS5 region in *Homo sapiens*, with the most intraspecies homologous genomic region demonstrating 78% identical coverage—with two nucleotide mismatches within the probe region, 11 mismatches in the forward primer region, and six mismatches in the reverse primer region. In addition, the most interspecies homologous genomic region was of the Sumatran orangutan, producing 79% identical coverage—with three nucleotide mismatches in the probe region and 13 mismatches in the forward primer region. No mismatches were found in the reverse primer region for the Sumatran orangutan. Table 2 provides the targeted region for the human-specific control assay and the components to the developed TaqMan assay.

TABLE 2

Genomic locations and primer and probe sequence information for the human-specific control

| Marker | Chr. | NCBI Accession # | Forward Primer | Reverse Primer | TaqMan Probe |
|---|---|---|---|---|---|
| HS5 | 12 | X17579.1 | SEQ ID NO: 24; GTATGAAG GCAGACAC ATACATGA | SEQ ID NO: 25; TTGTCAAC TTTGTTGA AGATCAGA | SEQ ID NO: 26; CATGATAG AGAACCC |
| Target Sequence | | | 5'GTATGAAGGCAGACACATAC ATGAATGGAACATGATAGAGAA CCCAGAAATAAAACCACACACC TACAGTCATCTGATCTTCAACA AAGTTGACAA3' SEQ ID NO: 22 | | |

C. Inhibition Control Gene Region

The inhibition control was developed using the Beta Actin gene sequence specific to the *Danio rerio* species (zebrafish). The genomic region utilized for TaqMan design was queried in NCBI using BLAST to ensure specificity to the targeted genomic region, and more importantly, that a homologous region did not exist within the human genome. The search demonstrated a 100% identical coverage of the beta-actin gene region in zebrafish, with the most homologous genomic region found in the *Channa striata* (snakehead) producing 88% identical coverage—with three nucleotide mismatches within the probe region, six mismatches in the forward primer region, and two mismatches in the reverse primer region. No homologous regions were found within mammalian genomes, including *Homo sapiens*. A MGB probe-based control assay was developed with a standardized 200 base pair synthetic oligonucleotide, representing the zebrafish βactin1 gene amplicon region. This oligonucleotide serves as template for the TaqMan chemistry. Table 3 provides the synthetic oligonucleotide, target region for the human-specific control assay, and the components to the developed TaqMan assay.

TABLE 3

Genomic locations and primer and probe sequence information for the inhibition control

| Marker | Chr. | NCBI Accession # | Forward Primer | Reverse Primer | TaqMan Probe |
|---|---|---|---|---|---|
| βactin1 | 3 | NC_007114 | SEQ ID NO: 27; GAGGGAC TTCCTTT GTCTGG | SEQ ID NO: 28; TCCTGTT TTGCTCT GCATTC | SEQ ID NO: 29; TCACTAGC GCCCACC |
| Synthetic Oligonucleotide Sequence | | | SEQ ID NO: 30; 5'GCGCTGCTGCCAGGGAGAGGCGTT TCAGCAAGCATGTGACCATCTGGAGT CAACTTCCTGTTTTGCTCTGCATTCT ACAGTCTGACCGCTGGTGGGCGCTAG TGACAGCGCGCGCCTCAGATATGCCA GACAAAGGAAGTCCCTCTGCATTCTC TCATTATTACCATAAAAGGCAATGGT TTGAGCCGCTTTGCGGCTGC3' | | |
| Target Sequence | | | SEQ ID NO: 23; 5'GAGGGACTTCCTTTGTCTGGCATA TCTGAGGCGCGCGCTGTCACTAGCGC CCACCAGCGGTCAGACTGTAGAATGC AGAGCAAAACAGGA3' | | |

Population Studies

Population studies have been previously performed to determine the suitability of these SNPs for individual identification (IISNPs) [1-4]. IISNPs are SNPs that are useful for human identification due to high heterozygosity (>0.4) and low genetic variance among populations ($F_{ST}$<0.06) (Table 4). High heterozygosity maximizes the information at each SNP, and low $F_{ST}$ minimizes chance variation between populations. These criteria were determined based on a set of 44 populations (44p) representing the major continental regions of the world including Africa, Southwest Asia, Europe, Northwest Asia, East Asia, Northeast Asia, Pacific Islands, North America, and South America [2,4].

TABLE 4

Average heterozygosity and $F_{ST}$ values for each IISNP [4]

| SNP | Avg. Het (44p) | $F_{ST}$ (44p) |
|---|---|---|
| rs9866013 | 0.419 | 0.0468 |
| rs1019029 | 0.474 | 0.0419 |
| rs2291395 | 0.473 | 0.0486 |
| rs12480506 | 0.403 | 0.0492 |
| rs315791 | 0.472 | 0.0539 |

Assay Components, Methods, Reaction Conditions, Thermalcycling Parameters, and Data Analysis Settings A. Assay Components A single RAZOR® EX Human Identification System kit contains the following components:
1. Foam swab
2. 3 ml vial of DNA-free water
3. Extraction tube containing lysis buffer and beads
4. Double barreled syringe containing neutralization solution
5. 3 ml blunt tipped plastic syringe
6. RAZOR Human Identification Pouch No additional components are necessary to utilize the kit.

B. Methods i. Purified DNA Sample Preparation

Purified DNA samples were diluted to the desired concentration with the bead beating extraction reagents included in the RAZOR® EX Human Identification System kit. The bead beating extraction materials consist of two components: one 5 ml extraction tube containing 600 μl lysis buffer and beads and one double barreled syringe containing 1780 μl water and 120 μl neutralization buffer. To create the diluent, the contents of the double barreled syringe were added to the 5 ml extraction tube.

ii. Dried Biological Stain Collection and Extraction

Deposited biological fluid samples were collected via swabbing with moistened foam swabs. Extraction was performed by breaking the tip of the swab into the 5 ml extraction tube that contained lysis buffer and beads. The sample was manually shaken for 15 seconds. Then, the contents of the double barreled syringe were added to the 5 ml extraction tube. The sample was shaken briefly to mix the reagents.

iii. Sample Loading

Diluted purified DNA or extracted biological fluids were drawn into a 3 ml syringe. The tip of the syringe was inserted into the sample inlet port of the RAZOR Human Identification Pouch to rehydrate the amplification reagents contained in slots 1-11. The same syringe was then inserted into the control inlet port of the RAZOR Human Identification Pouch to rehydrate the inhibition control reagents contained in slot 12.

iv. Instrument Loading

First, the 35MINRN4 thermalcycling protocol was loaded on the RAZOR® EX via a 2D barcode. To begin each run, a linear barcode was scanned to assign the appropriate thermalcycling protocol (35MINRN4) and an identification number to the sample. The green plastic comb was removed from the pouch, and a metal tool was used to turn the plungers 90° to unlock their positions. The plungers were depressed to force the rehydrated reagents into the individual lanes of the plastic pouch. Then, the pouch was inserted into RAZOR® EX instrument, and the run was started.

C. Reaction Conditions

The layout for the pouch is depicted in Table 5. A single well of the RAZOR Human Identification Pouch contains the following premixed lyophilized components: stabilization buffer, amplification buffer, TaqStart antibody, Taq polymerase, nucleotide mix, and sequence specific primers and fluorogenic probes for the SNPs and controls. Additionally, the inhibition control assay contains non-human synthetic DNA template. The reaction conditions, including amplification reagent concentrations, are listed in Table 6. During the developmental validation of the RAZOR® EX Human Identification System, the system was stored and operated at room temperature.

TABLE 5

Layout of the SNP assays in the RAZOR Human Identification Pouch

| Slot | SNP/Control | Allele |
|---|---|---|
| 1 | rs9866013 | C |
| 2 | rs9866013 | T |
| 3 | rs1019029 | C |
| 4 | rs1019029 | T |
| 5 | rs2291395 | A |
| 6 | rs2291395 | G |
| 7 | rs12480506 | A |
| 8 | rs12480506 | G |
| 9 | rs315791 | A |
| 10 | rs315791 | C |
| 11 | Human-Specific Control | |
| 12 | Inhibition Control | |

TABLE 6

RAZOR EX Human Identification System reaction components and concentrations

| Slots | Component | Volume (µl) |
|---|---|---|
| 1-11 | 4X Stabilization Buffer | 25 |
| 12 | 4X Stabilization Buffer | 24 |
| 1-11 | 50 mM Buffer 10X with BSA | 10 |
| 12 | 40 mM Buffer 10X with BSA | 10 |
| 1-12 | TaqStart Antibody | 0.264 |
| 1-12 | Taq Polymerase | 1.2 |
| 1-12 | 25 mM Roche Nucleomix | 0.80 |
| 1-12 | 100 µM Forward Primer | 0.40 |
| 1-12 | 100 µM Reverse Primer | 0.40 |
| 1-12 | 100 µM TaqMan MGB Probe | 0.25 |
| 12 | 20 fg/µl non-human synthetic DNA template | 1.0 |

D. Thermalcycling Parameters

The thermalcycling parameters for the RAZOR® EX Human Identification System are contained within a 2D barcode for amplification protocol 35MINRN4. The barcode can be scanned using the integrated RAZOR® EX Razor EX scanner. The complete thermalcycling program can be found in Table 7.

TABLE 7

RAZOR EX Human Identification System amplification parameters Amplification protocol 35MINRN4

| | |
|---|---|
| Hold: | 96° C. for 2 minutes |
| 50 cycles: | 96° C. for 5 seconds |
| | 64° C. for 25 seconds |

E. Data Analysis Settings

The following data analysis settings are programmed into an analysis algorithm developed by Bode Cellmark and are used for analysis of the raw RAZOR® EX data. The analysis settings are comprised of four major elements:

1. Exponential Amplification Equation

Baseline is 400 RFU

The ΔRFU is calculated from the difference between the RFU values of two points that are five cycles apart. Initiated at cycle 5, ΔRFU will be calculated for each subsequent cycle (5-50). For example, the difference in fluorescence at cycle 1 from cycle 5, cycle 2 from cycle 6, cycle 36 from 40, etc.

To be considered a positive call, five consecutive ΔRFU values (not aggregate), between cycles 5 and 50, must be greater than 42 ΔRFU.

2. Late Amplification Equation

Baseline is 400 RFU

The ΔRFU is calculated from the difference between the RFU values of two points that are five cycles apart. Beginning at cycle 48, ΔRFU will be calculated for each subsequent cycle (48-50). For example, the difference in fluorescence at cycle 44 from cycle 48, cycle 45 from cycle 49, and cycle 46 from 50.

To be considered a positive call, the three consecutive ΔRFU values (not aggregate), between cycles 48 and 50, must be greater than 40 ΔRFU.

3. Minimum Allele Presence

At each SNP locus, the presence of at least one allele must be detected. Wells 1-2, 3-4, 5-6, 7-8, and 9-10 represent paired wells for an individual SNP locus. For the run to be accepted, at least one assay from each paired well must return a positive call. When both alleles for any SNP are negative, the run has failed.

4. Positive Amplification of Controls

Both the human-specific control assay (well 11) and the inhibition control assay (well 12) must return positive calls for the run to be considered successful. If either control generates a negative result, the run has failed.

Example 1: Evaluation of Species Specificity

Description: The human specificity of the RAZOR® EX Human Identification System was examined using four different non-human DNA samples as described above.

Procedure: Twenty-five microliters of non-human blood (rat, bovine, canine, and rhesus monkey) were spotted on foam swabs in triplicate. The swabs were extracted using the bead beating extraction procedure included in the RAZOR® EX Human Identification System kit. The resulting fluorescence values were compared to those obtained from 5 ng/well of purified human DNA from a donor who was heterozygous for each SNP. Species specificity samples were run on RAZOR® EX 218 with the 35MINRN4 protocol.

Results and Discussion: Only rhesus monkey DNA had any significant cross reaction with the RAZOR® EX Human Identification System (Table 8). This was not unexpected as the rhesus genome shares approximately 93% of its sequence with the human genome [10]. Specifically, the rhesus monkey DNA reacted with the TaqMan probes for rs2291395 allele G, rs315791 allele C, and the human-specific control. Rat, bovine, and canine DNA showed little to no consistent cross reactivity (Table 8); however, one canine DNA sample generated a positive call for rs2291395 G (743 RFU) and another canine DNA sample generated a positive call for the human-specific control (174 RFU). Because these positive results were not replicated across the triplicate canine samples, it is not likely that they represent true cross reactivity of canine DNA with the RAZOR® EX Human Identification System. The inconsistent results obtained with canine DNA may be due to low level exogenous human DNA contamination introduced into the pouches during the lyophilization process (see Example 8).

Conclusions: The RAZOR® EX Human Identification System is a human-specific DNA identification system, and it demonstrates little to no consistent cross reactivity with other non-primate animals. More stringent manufacturing processes may need to be considered to ensure the RAZOR® EX Human Identification System is free of human DNA contamination.

Example 2: Sensitivity Studies

Description: The sensitivity of the RAZOR® EX Human Identification System was tested on a range of purified human DNA concentrations, from 0.0001-0.10 ng/µl (0.01-10.0 ng/well).

Procedure: Sensitivity was examined with various concentrations of purified DNA from three known donors who represented all possible genotypes for each SNP. Purified DNA was diluted to 0.0001 ng/µl, 0.001 ng/µl, 0.01 ng/µl, and 0.10 ng/µl in the bead beating extraction reagents included in the RAZOR® EX Human Identification System kit. One hundred microliters of diluted DNA was input into each pouch well, resulting in total DNA inputs of 0.01 ng/well, 0.1 ng/well, 1.0 ng/well, and 10.0 ng/well. Sensitivity samples were run on RAZOR® EX 1218 with the 35MINRN4 protocol.

Results and Discussion:

The expected positive and negative SNP calls were obtained for all of the 0.1 ng/well, 1.0 ng/well, and 10.0 ng/well samples (Table 9). These samples generated robust fluorescence values and accurate calls. Allelic dropout was observed in several of the 0.01 ng/well samples: genotype C/T with rs9866013 alleles C and T, genotype A/G with rs2291395 allele A, and genotypes G/G and A/G with rs12480506 allele G (Table 9). Additionally, the inhibition control did not amplify for one sample. It is unknown why this occurred as the sensitivity study samples did not contain

TABLE 8

Species specificity results

| SNP | Allel | N | Rat RFU | Rat +Calls | Bovine RFU | Bovine +Calls | Canine RFU | Canine +Calls |
|---|---|---|---|---|---|---|---|---|
| rs9866013 | C | 3 | 48.67 ± 3.21 | 0 | 44.33 ± 22.19 | 0 | 69.00 ± 31.76 | 0 |
|  | T | 3 | 30.67 ± 10.07 | 0 | 9.33 ± 16.17 | 0 | 50.76 ± 37.00 | 0 |
| rs1019029 | C | 3 | 7.33 ± 8.08 | 0 | 16.33 ± 24.09 | 0 | 23.33 ± 25.17 | 0 |
|  | T | 3 | 22.67 ± 12.01 | 0 | 15.00 ± 12.00 | 0 | 37.67 ± 21.20 | 0 |
| rs2291395 | A | 3 | 21.33 ± 4.16 | 0 | 8.33 ± 14.43 | 0 | 16.33 ± 24.09 | 0 |
|  | G | 3 | 25.33 ± 14.57 | 0 | 11.33 ± 19.63 | 0 | 287.00 ± 395.09 | 1 |
| rs12480506 | A | 3 | 8.67 ± 5.51 | 0 | 17.33 ± 30.02 | 0 | 14.33 ± 19.86 | 0 |
|  | G | 3 | 8.33 ± 10.41 | 0 | 2.67 ± 4.62 | 0 | 35.67 ± 31.79 | 0 |
| rs315791 | A | 3 | 12.33 ± 1.53 | 0 | 0.00 ± 0.00 | 0 | 14.33 ± 23.12 | 0 |
|  | C | 3 | 20.33 ± 15.95 | 0 | 5.67 ± 6.03 | 0 | 35.33 ± 30.60 | 0 |
| Human-Specific |  | 3 | 29.67 ± 13.58 | 0 | 27.67 ± 40.20 | 0 | 73.67 ± 90.01 | 1 |
| Inhibition |  | 3 | 813.33 ± 39.55 | 3 | 888.67 ± 70.68 | 3 | 1047.00 ± 68.64 | 3 |

| SNP | Allel | Rhesus Monkey RFU | Rhesus Monkey +Calls | Human RFU | Human +Calls |
|---|---|---|---|---|---|
| rs9866013 | C | 26.00 ± 14.93 | 0 | 747.00 ± 19.31 | 3 |
|  | T | 51.67 ± 16.62 | 0 | 965.00 ± 75.62 | 3 |
| rs1019029 | C | 35.00 ± 18.33 | 0 | 608.33 ± 76.51 | 3 |
|  | T | 28.33 ± 8.14 | 0 | 648.33 ± 65.19 | 3 |
| rs2291395 | A | 23.00 ± 7.21 | 0 | 693.67 ± 29.77 | 3 |
|  | G | 719.00 ± 285.43 | 3 | 878.33 ± 48.52 | 3 |
| rs12480506 | A | 18.33 ± 19.30 | 0 | 516.00 ± 16.09 | 3 |
|  | G | 7.33 ± 12.70 | 0 | 648.00 ± 39.89 | 3 |
| rs315791 | A | 28.67 ± 17.67 | 0 | 682.00 ± 38.12 | 3 |
|  | C | 622.33 ± 162.31 | 3 | 907.33 ± 56.37 | 3 |
| Human-Specific |  | 123.00 ± 19.31 | 3 | 944.67 ± 23.69 | 3 |
| Inhibition |  | 667.67 ± 160.81 | 3 | 1180.67 ± 135.5 | 3 |

Notes:
RFU: mean fluorescence value;
+calls: positive calls any PCR inhibitors. It is possible the sample was loaded incorrectly into the well containing the inhibition control. One false positive at rs315791 allele A was also observed with a 0.01 ng/well sample.

Conclusions: The RAZOR® EX Human Identification System is efficient in the range of 0.1 ng/well to 10.0 ng/well; therefore, the limit of detection of the assay is 0.1 ng/well.

TABLE 9

Sensitivity study results

| SNP | Allele | Genotype | Exp. + Calls | 0.01 ng/well RFU | +Calls | 0.1 ng/well RFU | +Calls |
|---|---|---|---|---|---|---|---|
| rs9866013 | C | C/C | 3 | 573.67 ± 26.10 | 3 | 744.33 ± 200.76 | 3 |
|  |  | C/T | 3 | 330.33 ± 250.48 | 2 | 655.67 ± 116.52 | 3 |
|  |  | T/T | 0 | 44.67 ± 19.04 | 0 | 47.33 ± 8.39 | 0 |
|  | T | T/T | 3 | 664.00 ± 98.24 | 3 | 920.67 ± 232.00 | 3 |
|  |  | C/T | 3 | 265.33 ± 259.18 | 2 | 642.00 ± 213.45 | 3 |
|  |  | C/C | 0 | 43.33 ± 38.37 | 0 | 21.67 ± 13.80 | 0 |
| rs1019029 | C | C/C | 3 | 657.33 ± 48.64 | 3 | 751.67 ± 180.10 | 3 |
|  |  | C/T | 3 | 431.67 ± 83.16 | 3 | 551.33 ± 121.33 | 3 |
|  |  | T/T | 0 | 16.67 ± 28.87 | 0 | 9.33 ± 12.10 | 0 |
|  | T | T/T | 3 | 666.00 ± 128.74 | 3 | 630.67 ± 241.58 | 3 |
|  |  | C/T | 3 | 382.67 ± 98.11 | 3 | 595.33 ± 103.00 | 3 |
|  |  | C/C | 0 | 55.67 ± 25.32 | 0 | 68.33 ± 4.73 | 0 |
| rs2291395 | A | A/A | 3 | 284.00 ± 314.27 | 3 | 599.67 ± 245.61 | 3 |
|  |  | A/G | 3 | 197.00 ± 201.32 | 2 | 399.00 ± 216.80 | 3 |
|  |  | G/G | 0 | 23.67 ± 4.73 | 0 | 26.33 ± 21.08 | 0 |
|  | G | G/G | 3 | 430.33 ± 260.72 | 3 | 970.00 ± 424.87 | 3 |
|  |  | A/G | 3 | 443.67 ± 237.05 | 3 | 632.00 ± 232.79 | 3 |
|  |  | A/A | 0 | 21.67 ± 22.01 | 0 | 16.00 ± 13.75 | 0 |
| rs12480506 | A | A/A | 3 | 498.33 ± 111.38 | 3 | 470.67 ± 190.27 | 3 |
|  |  | A/G | 3 | 297.67 ± 129.06 | 3 | 423.00 ± 128.71 | 3 |
|  |  | G/G | 0 | 45.00 ± 10.44 | 0 | 51.67 ± 27.15 | 0 |
|  | G | G/G | 3 | 378.67 ± 321.05 | 2 | 951.00 ± 222.67 | 3 |
|  |  | A/G | 3 | 274.67 ± 226.58 | 2 | 633.33 ± 127.08 | 3 |
|  |  | A/A | 0 | 40.67 ± 28.94 | 0 | 39.67 ± 25.32 | 0 |
| rs315791 | A | A/A | 3 | 481.67 ± 95.77 | 3 | 869.00 ± 166.64 | 3 |
|  |  | A/C | 3 | 224.00 ± 27.84 | 3 | 470.67 ± 179.58 | 3 |
|  |  | C/C | 0 | 127.00 ± 177.11 | 1 | 56.67 ± 40.82 | 0 |
|  | C | C/C | 3 | 549.00 ± 375.48 | 3 | 779.67 ± 347.13 | 3 |
|  |  | A/C | 3 | 463.33 ± 244.51 | 3 | 630.67 ± 229.99 | 3 |
|  |  | A/A | 0 | 42.67 ± 5.77 | 0 | 66.67 ± 23.25 | 0 |
| Human Specific Control |  |  | 3 | 297.33 ± 67.24 | 9 | 615.67 ± 391.80 | 9 |
|  |  |  | 3 | 335.67 ± 131.80 |  | 606.00 ± 162.86 |  |
|  |  |  | 3 | 291.33 ± 163.10 |  | 775.33 ± 64.01 |  |
| Inhibition Control |  |  | 3 | 777.33 ± 671.30 | 8 | 1,232.00 ± 319.22 | 9 |
|  |  |  | 3 | 1,207.33 ± 76.17 |  | 977.67 ± 258.78 |  |
|  |  |  | 3 | 1,200.67 ± 77.86 |  | 1,240.33 ± 51.81 |  |

| SNP | Allele | Genotype | 1.0 ng/well RFU | +Calls | 10 ng/well RFU | +Calls |
|---|---|---|---|---|---|---|
| rs9866013 | C | C/C | 993.00 ± 68.77 | 3 | 1,065.00 ± 28.21 | 3 |
|  |  | C/T | 716.00 ± 16.09 | 3 | 693.67 ± 31.64 | 3 |
|  |  | T/T | 65.67 ± 47.98 | 0 | 46.00 ± 14.73 | 0 |
|  | T | T/T | 1,166.67 ± 131.35 | 3 | 1,323.67 ± 143.29 | 3 |
|  |  | C/T | 822.67 ± 25.03 | 3 | 923.00 ± 114.84 | 3 |
|  |  | C/C | 70.67 ± 3.51 | 0 | 73.33 ± 26.58 | 0 |
| rs1019029 | C | C/C | 893.67 ± 121.22 | 3 | 948.67 ± 101.86 | 3 |
|  |  | C/T | 616.33 ± 40.86 | 3 | 571.67 ± 7.09 | 3 |
|  |  | T/T | 19.33 ± 4.04 | 0 | 34.33 ± 41.19 | 0 |
|  | T | T/T | 943.00 ± 75.29 | 3 | 1,009.67 ± 46.65 | 3 |
|  |  | C/T | 702.67 ± 35.35 | 3 | 681.67 ± 34.08 | 3 |
|  |  | C/C | 90.00 ± 13.89 | 0 | 75.33 ± 22.48 | 0 |
| rs2291395 | A | A/A | 951.67 ± 145.77 | 3 | 1,162.33 ± 67.57 | 3 |
|  |  | A/G | 626.00 ± 53.84 | 3 | 717.67 ± 78.56 | 3 |
|  |  | G/G | 48.33 ± 7.37 | 0 | 43.33 ± 10.26 | 0 |
|  | G | G/G | 1,318.00 ± 78.54 | 3 | 1,249.33 ± 110.70 | 3 |
|  |  | A/G | 827.67 ± 156.05 | 3 | 1,011.67 ± 133.99 | 3 |
|  |  | A/A | 49.33 ± 25.54 | 0 | 82.00 ± 23.64 | 0 |
| rs12480506 | A | A/A | 735.33 ± 61.46 | 3 | 858.67 ± 97.29 | 3 |
|  |  | A/G | 548.67 ± 31.13 | 3 | 529.33 ± 27.61 | 3 |
|  |  | G/G | 71.00 ± 7.55 | 0 | 67.00 ± 20.42 | 0 |
|  | G | G/G | 1,015.00 ± 41.58 | 3 | 1,044.67 ± 127.16 | 3 |
|  |  | A/G | 849.00 ± 94.32 | 3 | 682.33 ± 102.65 | 3 |
|  |  | A/A | 74.67 ± 15.50 | 0 | 96.00 ± 25.71 | 0 |
| rs315791 | A | A/A | 914.33 ± 98.08 | 3 | 947.67 ± 82.03 | 3 |
|  |  | A/C | 564.67 ± 59.00 | 3 | 643.00 ± 112.07 | 3 |
|  |  | C/C | 79.67 ± 8.14 | 0 | 100.33 ± 31.64 | 0 |

TABLE 9-continued

Sensitivity study results

| | | | | | |
|---|---|---|---|---|---|
| C | C/C | 1,217.33 ± 41.19 | 3 | 1,341.67 ± 86.70 | 3 |
| | A/C | 784.33 ± 62.53 | 3 | 934.33 ± 66.58 | 3 |
| | A/A | 100.67 ± 5.03 | 0 | 88.00 ± 9.00 | 0 |
| Human Specific Control | | 774.00 ± 224.40 | 9 | 902.00 ± 100.96 | 9 |
| | | 976.33 ± 55.43 | | 989.33 ± 199.15 | |
| | | 1,034.33 ± 109.26 | | 1,003.33 ± 107.62 | |
| Inhibition Control | | 1,128.33 ± 146.65 | 9 | 1,089.00 ± 134.71 | 9 |
| | | 1,254.33 ± 74.00 | | 1,194.67 ± 179.85 | |
| | | 1,220.67 ± 94.30 | | 1,156.00 ± 60.89 | |

Notes:
RFU: mean fluorescence value;
+calls: positive calls

Example 3: Stability

Description

The RAZOR® EX Human Identification System was tested with biological substances subjected to various environmental and chemical insults. Aged blood, semen, and saliva samples were examined. Additionally, purified DNA samples were subjected to known PCR inhibitors and artificial DNA degradation to mimic challenging sample types.

Procedure:

Biological Fluids: The RAZOR® EX Human Identification System was examined in conjunction with blood, semen, and saliva samples deposited on glass in triplicate in the following volumes: 1 µl and 25 µl blood, 1 µl and 25 µl semen, and 5 µl and 25 µl saliva. The samples were aged at room temperature for zero, one, and two weeks prior to sampling. Deposited biological fluid samples were collected via swabbing with moistened foam swabs. Extraction was performed using the bead beating extraction reagents included in the RAZOR® EX Human Identification System kit. All samples were amplified on RAZOR® EX 1218 with the 35MINRN4 protocol.

Inhibitors: In triplicate, 5 ng purified DNA from a donor who was heterozygous for each SNP was combined with the following concentrations of humic acid, hematin, or indigo dye: 0 ng, 500 ng, 1,000 ng, 1,500 ng, and 2,000 ng humic acid; 100 uM, 200 uM, 300 uM, and 400 uM hematin, and 1 mM, 2 mM, 4 mM, and 10 mM indigo dye. All samples were amplified on RAZOR® EX 1218 with the 35MINRN4 protocol.

Artificial Degradation: Five nanograms of purified DNA from a donor who was heterozygous for each SNP was subjected to artificial DNA degradation via UV irradiation. In triplicate, DNA was irradiated for 240 s, 480 s, 960 s, 1920 s, and 3840 s. All samples were amplified on RAZOR® EX 1218 with the 35MINRN4 protocol.

Results and Discussion:

Biological Fluids: At time point zero, one 25 µl blood sample exhibited allelic dropout at rs315791 allele A; however, a closer inspection of the real-time PCR graph revealed that this sample did amplify successfully. The software was unable to make a positive call due to the presence of many spikes in the sample's amplification curve. The spikes observed in this sample indicated that 25 µl of blood exceeds the ideal quantity for successful amplification and accurate genotyping. At the one week time point, both volumes of blood generated full and correct full profiles. At the two week time point, all blood samples except for one 1 µl blood sample generated a full and correct SNP profile (Table 10). At every time point, both volumes of semen and saliva samples generated full and correct SNP profiles (Table 11 and Table 12). For the 25 µl semen samples, the mean fluorescence values obtained for the inhibition control suggested that excess semen may have an inhibitory effect on the TaqMan assays. Several statistically significant differences (p<0.05) were observed between the aged biological stain samples and the time point zero samples (Table 10, Table 11, and Table 12). These differences resulted from natural degradative and oxidative forces that affect exposed biological samples.

Inhibitors: In general, a decrease in mean fluorescence value was observed as the amount of inhibitor in a DNA sample increased (Table 13). Additionally, more allelic dropout was observed in the samples that contained higher amounts of inhibitor (Table 14). With the exception of rs2291395 allele G, every SNP assay resulted in allelic dropout in ≥33% of the samples containing 2000 ng humic acid. Allelic dropout was also observed for every SNP assay in ≥33% of the samples containing 300 µM hematin, and no results were generated for any SNP assay for the samples containing 400 µM hematin. Every SNP assay exhibited allelic dropout for ≥33% of the samples containing 10 mM indigo dye.

Artificial Degradation: In general, a decrease in mean fluorescence value and an increase in allelic dropout were observed as the UV irradiation time increased (Table 15 and Table 16). SNP assays rs315791 A & C were the first to exhibit allelic dropout with samples that were subjected to UV irradiation for 1920 seconds. For the samples that were subject to UV irradiation for 3840 seconds, allelic dropout was observed with SNP assays rs1019029 C & T, rs2291395 A, rs12480506 A & G, and rs315791 A & C.

Conclusions: The RAZOR® EX Human Identification System is compatible with both freshly dried biological stains and stains that have been dried for up to two weeks. To obtain the best results, the user should aim to collect less than 25 µl of dried blood and semen. Although full profiles can be obtained from 1 µl of blood and semen, a slightly larger volume should be collected to produce consistent results. The system functioned well with both 5 µl and 25 µl saliva. The RAZOR® EX Human Identification System is capable of producing full and correct SNP profiles with up to 1500 ng humic acid, 200 µM hematin, and 4 mM indigo dye. Additionally, full and correct SNP profiles were obtained from artificially degraded DNA samples that had been subjected to UV irradiation for up to 960 seconds.

TABLE 10

Stability results for dried blood stains
Blood

| | | | | Positive Calls | | | RFU | | | p-value | |
|---|---|---|---|---|---|---|---|---|---|---|---|
| SNP | Allele | Amount (µl) | Exp. | Week 0 | Week 1 | Week 2 | Week 0 | Week 1 | Week 2 | Week 1 | Week 2 |
| rs9866013 | C | 1 | 3 | 3 | 3 | 3 | 632.00 ± 25.24 | 530.00 ± 39.89 | 466.67 ± 276.50 | 0.020* | 0.409 |
| | | 25 | 3 | 3 | 3 | 3 | 471.33 ± 41.20 | 552.00 ± 28.79 | 609.67 ± 28.15 | 0.050 | 0.009* |
| | T | 1 | 3 | 3 | 3 | 3 | 779.67 ± 50.72 | 668.67 ± 138.68 | 564.00 ± 329.37 | 0.263 | 0.374 |
| | | 25 | 3 | 3 | 3 | 3 | 553.67 ± 47.59 | 713.00 ± 30.51 | 714.00 ± 114.37 | 0.008* | 0.088 |
| rs1019029 | C | 1 | 0 | 0 | 0 | 0 | 37.33 ± 13.01 | 29.67 ± 25.70 | 15.67 ± 27.14 | 0.669 | 0.280 |
| | | 25 | 0 | 0 | 0 | 0 | 12.67 ± 21.94 | 0.00 ± 0.00 | 3.00 ± 5.20 | 0.374 | 0.374 |
| | T | 1 | 3 | 3 | 3 | 3 | 836.00 ± 37.27 | 818.33 ± 109.24 | 750.00 ± 203.93 | 0.804 | 0.512 |
| | | 25 | 3 | 3 | 3 | 3 | 648.00 ± 45.04 | 784.33 ± 89.91 | 797.00 ± 105.53 | 0.079 | 0.088 |
| rs2291395 | A | 1 | 3 | 3 | 3 | 2 | 444.00 ± 31.43 | 543.33 ± 89.01 | 317.00 ± 277.96 | 0.142 | 0.512 |
| | | 25 | 3 | 3 | 3 | 3 | 421.67 ± 33.86 | 566.67 ± 74.90 | 568.00 ± 128.49 | 0.038* | 0.129 |
| | G | 1 | 3 | 3 | 3 | 2 | 579.00 ± 119.05 | 531.00 ± 134.79 | 381.33 ± 320.75 | 0.668 | 0.374 |
| | | 25 | 3 | 3 | 3 | 3 | 522.00 ± 215.80 | 944.67 ± 358.06 | 705.00 ± 160.73 | 0.155 | 0.304 |
| rs12480506 | A | 1 | 3 | 3 | 3 | 2 | 617.67 ± 107.75 | 681.00 ± 36.51 | 475.67 ± 411.41 | 0.390 | 0.594 |
| | | 25 | 3 | 3 | 3 | 3 | 437.67 ± 47.54 | 686.00 ± 72.51 | 722.33 ± 93.55 | 0.008* | 0.009* |
| | G | 1 | 0 | 0 | 0 | 0 | 62.33 ± 27.23 | 62.33 ± 6.43 | 40.67 ± 36.68 | 1.000 | 0.472 |
| | | 25 | 0 | 0 | 0 | 0 | 16.00 ± 14.42 | 56.67 ± 32.87 | 48.33 ± 34.82 | 0.121 | 0.211 |
| rs315791 | A | 1 | 3 | 3 | 3 | 2 | 435.33 ± 65.45 | 457.67 ± 68.30 | 380.00 ± 357.24 | 0.704 | 0.805 |
| | | 25 | 3 | 2 | 3 | 3 | 370.33 ± 56.90 | 572.00 ± 152.68 | 721.00 ± 298.38 | 0.099 | 0.116 |
| | C | 1 | 3 | 3 | 3 | 3 | 726.33 ± 72.50 | 690.67 ± 78.56 | 602.00 ± 262.78 | 0.594 | 0.474 |
| | | 25 | 3 | 3 | 3 | 3 | 584.33 ± 11.37 | 809.00 ± 36.51 | 756.67 ± 160.86 | 0.001* | 0.204 |
| Human-Specific Control | | 1 | 3 | 3 | 3 | 3 | 703.00 ± 31.00 | 634.33 ± 30.57 | 594.33 ± 322.10 | 0.052 | 0.619 |
| | | 25 | 3 | 3 | 3 | 3 | 566.67 ± 40.46 | 817.33 ± 136.92 | 754.33 ± 152.55 | 0.038* | 0.109 |
| Inhibition Control | | 1 | 3 | 3 | 3 | 3 | 1080.33 ± 113.44 | 1061.33 ± 255.68 | 1027.67 ± 141.2 | 0.912 | 0.641 |
| | | 25 | 3 | 3 | 3 | 3 | 689.33 ± 41.04 | 838.67 ± 62.32 | 889.00 ± 48.07 | 0.026* | 0.005* |

Notes:
*p < 0.05 (two-tailed test);
Exp.: expected positive calls;
RFU: mean fluorescence value

TABLE 1

Stability results for dried semen stains
Semen

| | | | | Positive Calls | | | RFU | | | p-value | |
|---|---|---|---|---|---|---|---|---|---|---|---|
| SNP | Allele | Amount (µl) | Exp. | Week 0 | Week 1 | Week 2 | Week 0 | Week 1 | Week 2 | Week 1 | Week 2 |
| rs9866013 | C | 1 | 0 | 0 | 0 | 0 | 36.00 ± 14.42 | 35.67 ± 4.16 | 37.00 ± 6.56 | 0.971 | 0.918 |
| | | 25 | 0 | 0 | 0 | 0 | 0.00 ± 0.00 | 4.00 ± 6.93 | 0.00 ± 0.00 | 0.374 | — |
| | T | 1 | 3 | 3 | 3 | 3 | 1017.33 ± 220.57 | 1100.33 ± 82.03 | 1107.00 ± 41.04 | 0.574 | 0.527 |
| | | 25 | 3 | 3 | 3 | 3 | 524.00 ± 35.59 | 347.67 ± 41.19 | 428.33 ± 51.16 | 0.005* | 0.056 |
| rs1019029 | C | 1 | 3 | 3 | 3 | 3 | 521.00 ± 136.21 | 548.67 ± 28.02 | 537.67 ± 24.79 | 0.748 | 0.845 |
| | | 25 | 3 | 3 | 3 | 3 | 194.00 ± 25.51 | 175.00 ± 20.07 | 190.33 ± 50.93 | 0.368 | 0.917 |
| | T | 1 | 3 | 3 | 3 | 3 | 712.67 ± 50.52 | 611.67 ± 41.06 | 640.00 ± 15.72 | 0.055 | 0.076 |
| | | 25 | 3 | 3 | 3 | 3 | 241.67 ± 25.01 | 177.67 ± 37.82 | 221.67 ± 17.62 | 0.071 | 0.321 |
| rs2291395 | A | 1 | 3 | 3 | 3 | 3 | 754.67 ± 54.00 | 670.67 ± 111.46 | 539.00 ± 16.64 | 0.305 | 0.003* |
| | | 25 | 3 | 3 | 2 | 3 | 150.33 ± 33.49 | 96.33 ± 44.64 | 134.33 ± 18.01 | 0.169 | 0.506 |
| | G | 1 | 3 | 3 | 3 | 3 | 938.00 ± 83.54 | 775.67 ± 152.20 | 757.00 ± 86.02 | 0.181 | 0.059 |
| | | 25 | 3 | 3 | 3 | 3 | 260.33 ± 57.14 | 168.67 ± 75.65 | 176.00 ± 33.18 | 0.169 | 0.092 |
| rs12480506 | A | 1 | 3 | 3 | 3 | 3 | 838.00 ± 110.89 | 729.33 ± 23.46 | 939.33 ± 147.85 | 0.172 | 0.396 |
| | | 25 | 3 | 3 | 3 | 3 | 258.67 ± 55.01 | 183.00 ± 41.87 | 217.67 ± 58.50 | 0.131 | 0.426 |
| | G | 1 | 0 | 0 | 0 | 0 | 107.67 ± 21.73 | 50.00 ± 9.17 | 62.67 ± 13.32 | 0.013 | 0.038 |
| | | 25 | 0 | 0 | 0 | 0 | 0.00 ± 0.00 | 0.00 ± 0.00 | 0.00 ± 0.00 | N/A | N/A |
| rs315791 | A | 1 | 3 | 3 | 3 | 3 | 606.67 ± 82.48 | 557.00 ± 54.67 | 622.33 ± 20.40 | 0.434 | 0.765 |
| | | 25 | 3 | 3 | 2 | 3 | 244.00 ± 52.31 | 214.67 ± 77.69 | 230.33 ± 34.02 | 0.616 | 0.724 |
| | C | 1 | 3 | 3 | 3 | 3 | 812.67 ± 45.94 | 766.00 ± 52.46 | 837.00 ± 70.45 | 0.311 | 0.643 |
| | | 25 | 3 | 3 | 3 | 3 | 462.67 ± 60.47 | 371.67 ± 20.84 | 425.00 ± 57.03 | 0.069 | 0.476 |
| Human-Specific Control | | 1 | 3 | 3 | 3 | 3 | 916.67 ± 106.27 | 830.00 ± 118.17 | 966.00 ± 54.62 | 0.398 | 0.514 |
| | | 25 | 3 | 3 | 3 | 3 | 410.67 ± 97.90 | 312.67 ± 94.11 | 396.00 ± 67.67 | 0.279 | 0.841 |
| Inhibition Control | | 1 | 3 | 3 | 3 | 3 | 1146.67 ± 195.50 | 1011.00 ± 41.73 | 1038.67 ± 115.48 | 0.305 | 0.456 |
| | | 25 | 3 | 3 | 2 | 3 | 439.67 ± 91.84 | 199.00 ± 182.53 | 378.33 ± 70.44 | 0.111 | 0.411 |

Notes:
*p < 0.05 (two-tailed test);
Exp.: expected positive calls;
RFU: mean fluorescence value

TABLE 2

Stability results for dried saliva stains
Saliva

| | | | Positive Calls | | | RFU | | | p-value | |
|---|---|---|---|---|---|---|---|---|---|---|
| SNP | Allele | Amount (µl) | Exp. | Week 0 | Week 1 | Week 2 | Week 0 | Week 1 | Week 2 | Week 1 | Week 2 |
| rs9866013 | C | 5 | 0 | 0 | 0 | 0 | 52.67 ± 6.66 | 48.00 ± 15.10 | 41.00 ± 5.29 | 0.650 | 0.076 |
| | | 25 | 0 | 0 | 0 | 0 | 48.33 ± 12.74 | 54.00 ± 9.17 | 43.00 ± 8.66 | 0.566 | 0.581 |
| | T | 5 | 3 | 3 | 3 | 3 | 1,202.67 ± 77.50 | 974.33 ± 140.54 | 962.67 ± 134.58 | 0.069 | 0.055 |
| | | 25 | 3 | 3 | 3 | 3 | 1,312.67 ± 66.25 | 930.33 ± 356.15 | 1,190.33 ± 128.81 | 0.142 | 0.217 |
| rs1019029 | C | 5 | 3 | 3 | 3 | 3 | 1,000.00 ± 65.87 | 947.67 ± 106.83 | 892.00 ± 107.09 | 0.510 | 0.211 |
| | | 25 | 3 | 3 | 3 | 3 | 974.33 ± 46.14 | 896.67 ± 133.76 | 871.67 ± 29.14 | 0.396 | 0.031 * |
| | T | 5 | 0 | 0 | 0 | 0 | 86.00 ± 10.58 | 83.67 ± 19.86 | 85.33 ± 28.02 | 0.866 | 0.971 |
| | | 25 | 0 | 0 | 0 | 0 | 82.00 ± 32.97 | 90.67 ± 3.21 | 58.67 ± 4.93 | 0.694 | 0.345 |
| rs2291395 | A | 5 | 3 | 3 | 3 | 3 | 685.67 ± 93.61 | 598.00 ± 82.02 | 468.33 ± 59.16 | 0.289 | 0.027 * |
| | | 25 | 3 | 3 | 3 | 3 | 764.33 ± 68.24 | 646.67 ± 69.90 | 647.67 ± 83.26 | 0.105 | 0.134 |
| | G | 5 | 3 | 3 | 3 | 3 | 825.67 ± 129.39 | 708.33 ± 235.89 | 681.00 ± 127.47 | 0.492 | 0.240 |
| | | 25 | 3 | 3 | 3 | 3 | 1,022.33 ± 207.74 | 910.00 ± 212.71 | 837.33 ± 124.02 | 0.549 | 0.256 |
| rs12480506 | A | 5 | 3 | 3 | 3 | 3 | 833.33 ± 37.58 | 767.67 ± 126.75 | 737.33 ± 112.45 | 0.438 | 0.233 |
| | | 25 | 3 | 3 | 3 | 3 | 932.00 ± 143.10 | 701.33 ± 118.58 | 644.33 ± 51.19 | 0.098 | 0.031 * |
| | G | 5 | 0 | 0 | 0 | 0 | 86.33 ± 27.10 | 74.33 ± 1.53 | 73.33 ± 19.55 | 0.523 | 0.537 |
| | | 25 | 0 | 0 | 0 | 0 | 107.33 ± 37.53 | 88.67 ± 20.26 | 78.33 ± 24.01 | 0.491 | 0.323 |
| rs315791 | A | 5 | 3 | 3 | 3 | 3 | 606.00 ± 65.60 | 525.00 ± 89.03 | 539.67 ± 67.87 | 0.273 | 0.290 |
| | | 25 | 3 | 3 | 3 | 3 | 645.67 ± 42.15 | 532.33 ± 122.32 | 529.33 ± 37.85 | 0.204 | 0.024 * |
| | C | 5 | 3 | 3 | 3 | 3 | 769.33 ± 40.25 | 683.00 ± 106.69 | 681.33 ± 34.39 | 0.260 | 0.045 |
| | | 25 | 3 | 3 | 3 | 3 | 861.00 ± 42.46 | 765.33 ± 69.06 | 774.00 ± 93.55 | 0.110 | 0.216 |
| Human-Specific Control | | 5 | 3 | 3 | 3 | 3 | 793.67 ± 60.70 | 665.33 ± 171.80 | 754.67 ± 110.21 | 0.290 | 0.620 |
| | | 25 | 3 | 3 | 3 | 3 | 840.67 ± 167.36 | 654.00 ± 289.05 | 736.67 ± 240.28 | 0.388 | 0.572 |
| Inhibition Control | | 5 | 3 | 3 | 3 | 3 | 1,260.00 ± 184.40 | 973.00 ± 120.22 | 1,012.00 ± 100.26 | 0.087 | 0.110 |
| | | 25 | 3 | 3 | 3 | 3 | 1,204.33 ± 219.53 | 1,005.33 ± 170.83 | 942.33 ± 134.80 | 0.283 | 0.153 |

Notes:
Exp.: * $p < 0.05$ (two-tailed test); expected positive calls;
RFU: mean fluorescence value

TABLE 3

Mean fluorescence values generated by inhibited DNA samples

Humic Acid RFU

| SNP | Allele | 0 ng | 500 ng | 1000 ng | 1500 ng | 2000 ng |
|---|---|---|---|---|---|---|
| rs9866013 | C | 679.33 ± 27.74 | 575.67 ± 71.49 | 584.33 ± 85.13 | 463.33 ± 75.10 | 68.67 ± 12.50 |
| | T | 862.33 ± 87.58 | 631.33 ± 171.73 | 760.00 ± 29.51 | 653.67 ± 113.24 | 15.33 ± 14.19 |
| rs1019029 | C | 522.67 ± 78.81 | 570.33 ± 146.55 | 544.33 ± 79.10 | 403.33 ± 19.01 | 15.33 ± 14.19 |
| | T | 587.67 ± 29.02 | 581.67 ± 104.17 | 684.67 ± 32.39 | 389.00 ± 169.14 | 113.00 ± 142.03 |
| rs2291395 | A | 713.67 ± 97.34 | 602.00 ± 208.03 | 762.67 ± 205.65 | 542.33 ± 86.96 | 36.33 ± 26.76 |
| | G | 777.67 ± 83.34 | 657.67 ± 208.50 | 909.67 ± 44.86 | 579.67 ± 115.65 | 425.67 ± 130.19 |
| rs12480506 | A | 537.33 ± 34.02 | 468.67 ± 205.69 | 473.33 ± 61.44 | 277.33 ± 100.83 | 40.00 ± 27.18 |
| | G | 700.67 ± 46.18 | 627.00 ± 201.50 | 623.67 ± 30.99 | 275.33 ± 136.06 | 56.33 ± 44.88 |
| rs315791 | A | 617.33 ± 155.44 | 423.33 ± 104.31 | 508.00 ± 96.91 | 303.00 ± 65.11 | 50.67 ± 26.10 |
| | C | 788.33 ± 152.75 | 627.67 ± 166.00 | 680.33 ± 52.32 | 376.00 ± 90.02 | 72.33 ± 58.16 |
| Human-Specific Control | | 896.00 ± 45.30 | 456.33 ± 365.17 | 557.00 ± 61.54 | 82.00 ± 29.14 | 56.00 ± 14.18 |
| Inhibition Control | | 896.00 ± 45.30 | 920.00 ± 168.68 | 851.33 ± 177.70 | 275.83 ± 232.84 | 69.00 ± 9.17 |

Hematin RFU

| SNP | Allele | 0 µM | 100 µM | 200 µM | 300 µM | 400 µM |
|---|---|---|---|---|---|---|
| rs9866013 | C | 679.33 ± 27.74 | 649.44 ± 58.77 | 432.67 ± 20.03 | 149.33 ± 188.24 | 36.67 ± 3.51 |
| | T | 862.33 ± 87.58 | 636.00 ± 40.26 | 403.33 ± 101.66 | 165.33 ± 105.34 | 21.00 ± 16.00 |
| rs1019029 | C | 522.67 ± 78.81 | 541.33 ± 52.20 | 413.67 ± 70.73 | 83.33 ± 76.22 | 21.33 ± 23.18 |
| | T | 587.67 ± 29.02 | 604.33 ± 68.85 | 390.33 ± 59.52 | 160.00 ± 150.40 | 14.67 ± 13.05 |
| rs2291395 | A | 713.67 ± 97.34 | 572.00 ± 81.22 | 393.67 ± 167.83 | 175.67 ± 127.36 | 13.00 ± 1.73 |
| | G | 777.67 ± 83.34 | 873.33 ± 142.15 | 562.67 ± 122.93 | 280.67 ± 229.26 | 22.67 ± 12.10 |
| rs12480506 | A | 537.33 ± 34.02 | 530.33 ± 49.81 | 385.00 ± 35.51 | 169.67 ± 172.18 | 31.33 ± 18.45 |
| | G | 700.67 ± 46.18 | 704.00 ± 56.51 | 483.33 ± 122.35 | 133.33 ± 114.48 | 9.67 ± 8.39 |
| rs315791 | A | 617.33 ± 155.44 | 501.00 ± 63.98 | 311.67 ± 58.32 | 88.67 ± 58.35 | 27.00 ± 5.20 |
| | C | 788.33 ± 152.75 | 727.67 ± 71.11 | 407.33 ± 137.15 | 125.33 ± 161.72 | 23.33 ± 13.87 |
| Human-Specific Control | | 788.33 ± 203.63 | 656.33 ± 69.60 | 192.67 ± 17.01 | 46.33 ± 17.21 | 45.33 ± 16.04 |
| Inhibition Control | | 896.00 ± 45.30 | 875.33 ± 118.51 | 518.00 ± 435.60 | 428.17 ± 735.41 | 53.67 ± 20.55 |

TABLE 3-continued

Mean fluorescence values generated by inhibited DNA samples

Indigo Dye $\overline{RFU}$

| SNP | Allele | 0 mM | 1 mM | 2 mM | 4 mM | 10 mM |
|---|---|---|---|---|---|---|
| rs9866013 | C | 679.33 ± 27.74 | 536.00 ± 51.64 | 532.67 ± 45.94 | 337.67 ± 33.50 | 151.33 ± 110.34 |
|  | T | 862.33 ± 87.58 | 817.33 ± 47.44 | 720.33 ± 86.75 | 513.67 ± 73.70 | 305.67 ± 239.21 |
| rs1019029 | C | 522.67 ± 78.81 | 595.00 ± 55.76 | 506.67 ± 83.50 | 372.00 ± 71.04 | 275.00 ± 148.36 |
|  | T | 587.67 ± 29.02 | 563.00 ± 51.22 | 513.00 ± 60.83 | 345.67 ± 34.53 | 310.67 ± 196.45 |
| rs2291395 | A | 713.67 ± 97.34 | 622.33 ± 51.42 | 589.67 ± 26.31 | 452.00 ± 71.08 | 258.33 ± 223.20 |
|  | G | 777.67 ± 83.34 | 685.33 ± 85.98 | 692.00 ± 148.36 | 524.00 ± 45.43 | 131.33 ± 82.98 |
| rs12480506 | A | 537.33 ± 34.02 | 458.33 ± 72.61 | 428.67 ± 25.70 | 330.67 ± 36.83 | 91.00 ± 57.71 |
|  | G | 700.67 ± 46.18 | 643.33 ± 52.17 | 497.67 ± 91.58 | 378.33 ± 36.30 | 157.67 ± 124.30 |
| rs315791 | A | 617.33 ± 155.44 | 481.67 ± 42.45 | 386.67 ± 20.23 | 268.67 ± 34.70 | 195.00 ± 181.36 |
|  | C | 788.33 ± 152.75 | 791.00 ± 95.50 | 643.67 ± 104.64 | 409.00 ± 64.21 | 259.67 ± 196.63 |
| Human-Specific Control |  | 788.33 ± 203.63 | 735.00 ± 100.46 | 652.67 ± 108.35 | 349.00 ± 61.73 | 337.00 ± 265.57 |
| Inhibition Control |  | 896.00 ± 45.30 | 894.33 ± 31.56 | 859.67 ± 174.74 | 394.33 ± 51.05 | 136.33 ± 112.61 |

TABLE 4

Positive calls generated by inhibited DNA samples

| SNP | Allele | Exp. + Calls | Humic Acid 0 ng | 500 ng | 1000 ng | 1500 ng | 2000 ng | Hematin 0 μM | 100 μM | 200 μM | 300 μM | 400 μM | Indigo Dye 0 mM | 1 mM | 2 mM | 4 mM | 10 mM |
|---|---|---|---|---|---|---|---|---|---|---|---|---|---|---|---|---|---|
| rs9866013 | C | 3 | 3 | 3 | 3 | 3 | 0 | 3 | 3 | 3 | 1 | 0 | 3 | 3 | 3 | 3 | 1 |
|  | T | 3 | 3 | 3 | 3 | 3 | 0 | 3 | 3 | 3 | 2 | 0 | 3 | 3 | 3 | 3 | 2 |
| rs1019029 | C | 3 | 3 | 3 | 3 | 3 | 0 | 3 | 3 | 3 | 2 | 0 | 3 | 3 | 3 | 3 | 2 |
|  | T | 3 | 3 | 3 | 3 | 3 | 1 | 3 | 3 | 3 | 2 | 0 | 3 | 3 | 3 | 3 | 2 |
| rs2291395 | A | 3 | 3 | 3 | 3 | 3 | 0 | 3 | 3 | 3 | 2 | 0 | 3 | 3 | 3 | 3 | 1 |
|  | G | 3 | 3 | 3 | 3 | 3 | 3 | 3 | 3 | 3 | 2 | 0 | 3 | 3 | 3 | 3 | 0 |
| rs12480506 | A | 3 | 3 | 3 | 3 | 3 | 0 | 3 | 3 | 3 | 1 | 0 | 3 | 3 | 3 | 3 | 0 |
|  | G | 3 | 3 | 3 | 3 | 3 | 1 | 3 | 3 | 3 | 2 | 0 | 3 | 3 | 3 | 3 | 0 |
| rs315791 | A | 3 | 3 | 3 | 3 | 3 | 0 | 3 | 3 | 3 | 1 | 0 | 3 | 3 | 3 | 3 | 1 |
|  | C | 3 | 3 | 3 | 3 | 3 | 0 | 3 | 3 | 3 | 1 | 0 | 3 | 3 | 3 | 3 | 1 |
| Human-Specific Control |  | 3 | 3 | 3 | 3 | 3 | 0 | 3 | 3 | 3 | 0 | 0 | 3 | 3 | 3 | 3 | 2 |
| Inhibition Control |  | 3 | 3 | 3 | 3 | 3 | 0 | 3 | 3 | 3 | 2 | 0 | 3 | 3 | 3 | 3 | 0 |

TABLE 5

Mean fluorescence values generated by artificially degraded DNA samples

| SNP | Allele | $\overline{RFU}$ 0 sec | 240 sec | 480 sec |
|---|---|---|---|---|
| rs9866013 | C | 747.00 ± 19.31 | 712.67 ± 16.29 | 677.33 ± 32.35 |
|  | T | 965.00 ± 75.62 | 840.00 ± 11.00 | 871.67 ± 67.16 |
| rs1019029 | C | 608.33 ± 76.51 | 631.67 ± 42.10 | 543.67 ± 7.09 |
|  | T | 648.33 ± 65.19 | 656.00 ± 83.26 | 629.67 ± 74.00 |
| rs2291395 | A | 693.67 ± 29.77 | 681.00 ± 60.75 | 675.00 ± 81.73 |
|  | G | 878.33 ± 48.52 | 937.00 ± 87.71 | 945.00 ± 21.38 |
| rs12480506 | A | 516.00 ± 16.09 | 614.33 ± 45.54 | 594.00 ± 85.49 |
|  | G | 648.00 ± 39.89 | 723.00 ± 63.32 | 665.00 ± 57.11 |
| rs315791 | A | 682.00 ± 38.12 | 651.67 ± 142.61 | 615.00 ± 51.80 |
|  | C | 907.33 ± 56.37 | 970.67 ± 99.81 | 789.00 ± 34.66 |
| Human-Specific Control |  | 944.67 ± 23.69 | 1,067.00 ± 182.76 | 896.67 ± 20.82 |
| Inhibition Control |  | 1,180.67 ± 135.50 | 1,256.00 ± 176.27 | 1,207.67 ± 99.95 |

| SNP | Allele | $\overline{RFU}$ 960 sec | 1920 s | 3840 s |
|---|---|---|---|---|
| rs9866013 | C | 614.00 ± 61.02 | 408.67 ± 113.23 | 289.67 ± 150.51 |
|  | T | 727.00 ± 101.57 | 462.33 ± 78.68 | 544.33 ± 80.03 |
| rs1019029 | C | 558.00 ± 47.84 | 382.67 ± 63.52 | 122.67 ± 144.43 |
|  | T | 513.33 ± 52.55 | 411.00 ± 150.57 | 20.33 ± 15.57 |

TABLE 5-continued

Mean fluorescence values generated by artificially degraded DNA samples

| rs2291395 | A | 525.00 ± 93.54 | 365.67 ± 137.66 | 194.00 ± 164.33 |
| --- | --- | --- | --- | --- |
| | G | 766.33 ± 43.56 | 686.33 ± 83.07 | 469.00 ± 201.00 |
| rs12480506 | A | 520.67 ± 221.41 | 357.67 ± 132.31 | 43.33 ± 13.05 |
| | G | 549.00 ± 53.25 | 541.33 ± 168.36 | 172.00 ± 174.52 |
| rs315791 | A | 427.67 ± 11.15 | 88.67 ± 58.35 | 102.67 ± 58.11 |
| | C | 652.67 ± 77.69 | 303.33 ± 281.12 | 46.33 ± 24.13 |
| Human-Specific Control | | 809.00 ± 142.92 | 506.67 ± 163.67 | 356.33 ± 80.04 |
| Inhibition Control | | 1,260.67 ± 129.87 | 1,018.33 ± 38.08 | 1,107.00 ± 93.04 |

TABLE 6

Positive calls generated by artificially degraded DNA samples

| SNP | Allele | Expected Call | Positive Calls | | | | | |
| --- | --- | --- | --- | --- | --- | --- | --- | --- |
| | | | 0 sec | 240 sec | 480 sec | 960 sec | 1920 sec | 3840 sec |
| rs9866013 | C | 3 | 3 | 3 | 3 | 3 | 3 | 3 |
| | T | 3 | 3 | 3 | 3 | 3 | 3 | 3 |
| rs1019029 | C | 3 | 3 | 3 | 3 | 3 | 3 | 1 |
| | T | 3 | 3 | 3 | 3 | 3 | 3 | 0 |
| rs2291395 | A | 3 | 3 | 3 | 3 | 3 | 3 | 2 |
| | G | 3 | 3 | 3 | 3 | 3 | 3 | 3 |
| rs12480506 | A | 3 | 3 | 3 | 3 | 3 | 3 | 0 |
| | G | 3 | 3 | 3 | 3 | 3 | 3 | 1 |
| rs315791 | A | 3 | 3 | 3 | 3 | 3 | 1 | 1 |
| | C | 3 | 3 | 3 | 3 | 3 | 2 | 0 |
| Human-Specific Control | | 3 | 3 | 3 | 3 | 3 | 3 | 3 |
| Inhibition Control | | 3 | 3 | 3 | 3 | 3 | 3 | 3 |

Example 4: Repeatability—Precision and Accuracy

Description:

The precision and accuracy of the RAZOR® EX Human Identification System within the same RAZOR® EX device were tested with 5 ng of DNA from donors representing all genotypes for each SNP. Accuracy is used to describe the closeness of a measurement to the true value. Precision is the closeness of agreement among a set of results.

Procedure:

In triplicate, purified DNA from three known donors who represented all possible genotypes for each SNP was diluted to 0.05 ng/μl in the bead beating extraction reagents included in the RAZOR® EX Human Identification System kit. One hundred microliters of the diluted DNA was used to rehydrate each well of the RAZOR Human Identification Pouch (5 ng DNA per well). Repeatability samples were run on RAZOR® EX 1218 with the 35MINRN4 protocol.

Results and Discussion:

The results for the repeatability testing are displayed in Table 17.

Accuracy: Accuracy was determined by comparing the expected SNP calls to the obtained SNP calls. The results show that allelic discrimination with the RAZOR® EX Human Identification System is accurate; however, one homozygous A/A sample generated a false positive call with the TaqMan probe for rs12480506 allele G (Table 17). This can most likely be attributed to low level exogenous human DNA that may have been introduced into some of the pouches during lyophilization. Despite this, the overall results are consistent with the expected calls for each DNA donor.

Precision: Precision was determined through two methods: assessing the standard deviations of the fluorescence values (RFU) generated by the triplicate sets and examining the number of calls that were in agreement for each SNP probe. For each SNP probe, the standard deviation was within one-third of the average fluorescence value. This amount of variation does not have a negative impact on the overall efficacy of the RAZOR® EX Human Identification System. Additionally, some degree of variation in fluorescence is expected due to the effects of the lyophilization process on the amplification reagents.

For the majority of the TaqMan assays, the calls for the triplicate sets were in 100% agreement with each other. This included the assays for rs9866013 C & T, rs1019029 C & T, rs2291395 A & G, rs12480506 A, rs315791 A & C, the human-specific control, and the inhibition control. For rs12480506 allele G, one homozygous A/A sample generated a false positive call, which did not agree with the calls generated by the other samples in the triplicate set. The cause of this difference was hypothesized above.

Conclusions:

Overall, the RAZOR® EX Human Identification System produces precise and accurate results; however, more stringent manufacturing processes may need to be considered to ensure the RAZOR Human Identification Pouches are free of human DNA contamination.

TABLE 7

Repeatability results

| SNP | Allele | Donor Genotype | Expected + Calls | +Calls | RFU | | | $\overline{\text{RFU}}$ | SD |
| --- | --- | --- | --- | --- | --- | --- | --- | --- | --- |
| | | | | | Rep 1 | Rep 2 | Rep 3 | | |
| rs9866013 | C | C/C | 3 | 3 | 951 | 995 | 961 | 969.0 | 23.1 |
| | | C/T | 3 | 3 | 566 | 634 | 623 | 607.7 | 36.5 |
| | | T/T | 0 | 0 | 50 | 53 | 67 | 56.7 | 9.1 |
| | T | T/T | 3 | 3 | 887 | 1124 | 1210 | 1073.7 | 167.3 |
| | | C/T | 3 | 3 | 439 | 685 | 861 | 661.7 | 212.0 |
| | | C/C | 0 | 0 | 87 | 108 | 83 | 92.7 | 13.4 |
| rs1019029 | C | C/C | 3 | 3 | 427 | 895 | 790 | 704.0 | 245.6 |
| | | C/T | 3 | 3 | 397 | 539 | 586 | 507.3 | 98.4 |
| | | T/T | 0 | 0 | 44 | 94 | 45 | 61.0 | 28.6 |

TABLE 7-continued

Repeatability results

| SNP | Allele | Donor Genotype | Expected + Calls | +Calls | RFU Rep 1 | Rep 2 | Rep 3 | $\overline{\text{RFU}}$ | SD |
|---|---|---|---|---|---|---|---|---|---|
| | T | T/T | 3 | 3 | 823 | 1034 | 753 | 870.0 | 146.3 |
| | | C/T | 3 | 3 | 438 | 477 | 595 | 503.3 | 81.7 |
| | | C/C | 0 | 0 | 49 | 72 | 92 | 71.0 | 21.5 |
| rs2291395 | A | A/A | 3 | 3 | 697 | 1040 | 1085 | 940.7 | 212.2 |
| | | A/G | 3 | 3 | 564 | 869 | 539 | 657.3 | 183.7 |
| | | G/G | 0 | 0 | 0 | 20 | 31 | 17.0 | 15.7 |
| | G | G/G | 3 | 3 | 807 | 947 | 1012 | 922.0 | 104.8 |
| | | A/G | 3 | 3 | 616 | 985 | 559 | 720.0 | 231.3 |
| | | A/A | 0 | 0 | 9 | 75 | 95 | 59.7 | 45.0 |
| rs12480506 | A | A/A | 3 | 3 | 650 | 924 | 737 | 770.3 | 140.0 |
| | | A/G | 3 | 3 | 404 | 395 | 536 | 445.0 | 78.9 |
| | | G/G | 0 | 0 | 43 | 97 | 95 | 78.3 | 30.6 |
| | G | G/G | 3 | 3 | 822 | 1047 | 1191 | 1020.0 | 186.0 |
| | | A/G | 3 | 3 | 398 | 704 | 770 | 624.0 | 198.5 |
| | | A/A | 0 | 1 | 74 | 159 | 68 | 100.3 | 50.9 |
| rs315791 | A | A/A | 3 | 3 | 401 | 726 | 679 | 602.0 | 175.7 |
| | | A/C | 3 | 3 | 412 | 662 | 522 | 532.0 | 125.3 |
| | | C/C | 0 | 0 | 28 | 69 | 93 | 63.3 | 32.9 |
| | C | C/C | 3 | 3 | 893 | 971 | 844 | 902.7 | 64.0 |
| | | A/C | 3 | 3 | 693 | 940 | 731 | 788.0 | 133.0 |
| | | A/A | 0 | 0 | 29 | 84 | 66 | 59.7 | 28.0 |
| Human Specific Control | | | 3 | 3 | 596 | 779 | 730 | 701.7 | 94.7 |
| | | | 3 | 3 | 680 | 1063 | 736 | 826.3 | 206.9 |
| | | | 3 | 3 | 553 | 917 | 874 | 781.3 | 198.9 |
| Inhibition Control | | | 3 | 3 | 1204 | 1169 | 1014 | 1129.0 | 101.1 |
| | | | 3 | 3 | 963 | 1229 | 906 | 1032.7 | 172.4 |
| | | | 3 | 3 | 824 | 1056 | 1052 | 977.3 | 132.8 |

Notes:
$\overline{\text{RFU}}$: mean fluorescence value;
+calls: positive calls;
SD: standard deviation

Example 5: Reproducibility—Precision and Accuracy

Description:

The precision and accuracy of the RAZOR® EX Human Identification System among different RAZOR® EX devices were tested with 5 ng of DNA from donors representing all genotypes for each SNP. Accuracy is used to describe the closeness of a measurement to the true value. Precision is the closeness of agreement among a set of results.

Procedure:

Purified DNA from three known donors who represented all possible genotypes for each SNP was diluted to 0.05 ng/µl in the bead beating extraction reagents included in the RAZOR® EX Human Identification System kit. One hundred microliters of the diluted DNA was used to rehydrate each well of the RAZOR® Human Identification Pouch (5 ng DNA per well). One triplicate set of reproducibility samples was run on RAZOR® EX 1218 with the 35MINRN4 protocol. A second triplicate set of reproducibility samples was run on RAZOR® EX 1203 with the 35MINRN4 protocol.

Results and Discussion:

The results for the repeatability testing are displayed in Table 18.

Accuracy: Accuracy was determined by comparing the expected calls to the calls obtained with each RAZOR® EX device. The results for both RAZOR® EX devises show that allelic discrimination with the RAZOR® EX Human Identification System is accurate; however, one homozygous A/A sample generated a false positive call with the TaqMan probe for rs12480506 allele G on RAZOR® EX 1218 (Table 18). This false positive can most likely be attributed to low level exogenous human DNA that may have been introduced into some of the pouches during lyophilization. Despite this, the overall results obtained with both RAZOR® EX 1203 and RAZOR® EX 1218 are consistent with each other and the expected calls for each DNA donor.

Precision: Precision was determined through two methods: comparing the fluorescence values (RFU) generated by the triplicate sets on each RAZOR® EX device and examining the number of calls for each SNP probe that were in agreement between the RAZOR® EX devices. Two-tailed t-test comparisons of the fluorescence values generated by each RAZOR® EX device revealed the assays for rs1019029 C & T, rs2291395 A & G, rs12480506 A, rs315791 A & C, and the human-specific control generated similar fluorescence values between the two RAZOR® EX devices. Statistically significant differences ($p < 0.05$) were observed between the fluorescence values generated by each device at rs9866013 C & T and the inhibition control (Table 18). These results suggested that the detection sensitivity between RAZOR® EX devices may differ for the assays located in the extreme ends of the RAZOR Human Identification Pouch.

For the majority of the TaqMan assays, the calls for the triplicate sets were in 100% agreement between the RAZOR® EX devices. This included the assays for rs9866013 C & T, rs1019029 C & T, rs2291395 A & G, rs12480506 A, rs315791 A & C, the human-specific control, and the inhibition control. For rs12480506 allele G, one homozygous A/A sample generated a false positive call, which did not agree with the calls generated by the other samples on either RAZOR® EX device. The cause of this difference was hypothesized above.

Conclusions:

Overall, the RAZOR® EX Human Identification System generates precise and accurate results between different RAZOR® EX devices; however, more stringent manufacturing processes may need to be considered to ensure the RAZOR Human Identification Pouches are free of human DNA contamination.

Results and Discussion:

The fluorescence values generated by the aged biological fluid samples were averaged (Table 19). For blood, the 1 µl samples generated lower mean fluorescence values than the 25 µl samples, whereas the 1 µl semen samples generated higher mean fluorescence values than the 25 µl semen samples. The mean fluorescence values generated by the

TABLE 8

Reproducibility results

| SNP | Allele | Donor Genotype | Positive Calls Expected | RAZOR EX 1203 | RAZOR EX 1218 | RFU RAZOR EX 1203 | RAZOR EX 1218 | p-value |
|---|---|---|---|---|---|---|---|---|
| rs9866013 | C | C/C | 3 | 3 | 3 | 808.7 ± 100.3 | 969.0 ± 23.1 | 0.054 |
| | | C/T | 3 | 3 | 3 | 492.3 ± 45.3 | 607.7 ± 36.5 | 0.026* |
| | | T/T | 0 | 0 | 0 | 22.3 ± 11.0 | 56.7 ± 9.1 | 0.014* |
| | T | T/T | 3 | 3 | 3 | 830.7 ± 52.9 | 1,073.7 ± 167.3 | 0.074 |
| | | C/T | 3 | 3 | 3 | 542.7 ± 57.4 | 661.7 ± 212.0 | 0.401 |
| | | C/C | 0 | 0 | 0 | 47.0 ± 4.0 | 92.7 ± 13.4 | 0.005* |
| rs1019029 | C | C/C | 3 | 3 | 3 | 645.7 ± 46.1 | 704.0 ± 245.6 | 0.707 |
| | | C/T | 3 | 3 | 3 | 422.3 ± 33.3 | 507.3 ± 98.4 | 0.229 |
| | | T/T | 0 | 0 | 0 | 36.0 ± 10.6 | 61.0 ± 28.6 | 0.228 |
| | T | T/T | 3 | 3 | 3 | 669.3 ± 153.3 | 870.0 ± 146.3 | 0.176 |
| | | C/T | 3 | 3 | 3 | 441.3 ± 111.7 | 503.3 ± 81.7 | 0.481 |
| | | C/C | 0 | 0 | 0 | 59.7 ± 9.6 | 71.0 ± 21.5 | 0.452 |
| rs2291395 | A | A/A | 3 | 3 | 3 | 797.0 ± 94.8 | 940.7 ± 212.2 | 0.345 |
| | | A/G | 3 | 3 | 3 | 533.3 ± 123.6 | 657.3 ± 183.7 | 0.387 |
| | | G/G | 0 | 0 | 0 | 33.0 ± 11.5 | 17.0 ± 15.7 | 0.228 |
| | G | G/G | 3 | 3 | 3 | 799.0 ± 299.3 | 922.0 ± 104.8 | 0.538 |
| | | A/G | 3 | 3 | 3 | 605.0 ± 93.0 | 720.0 ± 231.3 | 0.469 |
| | | A/A | 0 | 0 | 0 | 57.7 ± 5.5 | 59.7 ± 45.0 | 0.946 |
| rs12480506 | A | A/A | 3 | 3 | 3 | 616.3 ± 92.4 | 770.3 ± 140.0 | 0.187 |
| | | A/G | 3 | 3 | 3 | 411.3 ± 84.6 | 445.0 ± 78.9 | 0.641 |
| | | G/G | 0 | 0 | 0 | 64.3 ± 28.9 | 78.3 ± 30.6 | 0.596 |
| | G | G/G | 3 | 3 | 3 | 820.0 ± 73.7 | 1,020.0 ± 186.0 | 0.158 |
| | | A/G | 3 | 3 | 3 | 395.0 ± 152.7 | 624.0 ± 198.5 | 0.188 |
| | | A/A | 0 | 0 | 1 | 75.7 ± 28.4 | 100.3 ± 50.9 | 0.504 |
| rs315791 | A | A/A | 3 | 3 | 3 | 519.0 ± 160.8 | 602.0 ± 175.7 | 0.579 |
| | | A/C | 3 | 3 | 3 | 407.0 ± 92.1 | 532.0 ± 125.3 | 0.236 |
| | | C/C | 0 | 0 | 0 | 73.3 ± 15.8 | 63.3 ± 32.9 | 0.660 |
| | C | C/C | 3 | 3 | 3 | 867.7 ± 72.4 | 902.7 ± 64.0 | 0.565 |
| | | A/C | 3 | 3 | 3 | 557.7 ± 163.3 | 788.0 ± 133.0 | 0.131 |
| | | A/A | 0 | 0 | 0 | 51.7 ± 23.6 | 59.7 ± 28.0 | 0.725 |
| Human-Specific Control | | | 3 | 3 | 3 | 729.7 ± 88.2 | 701.7 ± 94.7 | 0.727 |
| | | | 3 | 3 | 3 | 698.7 ± 73.6 | 826.3 ± 206.9 | 0.371 |
| | | | 3 | 3 | 3 | 540.7 ± 131.1 | 781.3 ± 198.9 | 0.155 |
| Inhibition Control | | | 3 | 3 | 3 | 740.3 ± 96.2 | 1,129.0 ± 101.1 | 0.008* |
| | | | 3 | 3 | 3 | 768.7 ± 11.0 | 1,032.7 ± 172.4 | 0.117 |
| | | | 3 | 3 | 3 | 688.3 ± 40.1 | 977.3 ± 132.8 | 0.023* |

Notes:
*p < 0.05 (two-tailed test);
RFU: mean fluorescence value;
+calls: positive calls Example 6: Mock Casework Samples Description:

The RAZOR® EX Human Identification System was tested using 18 mock casework samples.

Procedure:

The RAZOR® EX Human Identification System was examined in conjunction with blood, semen, and saliva samples deposited on glass in triplicate in the following volumes: 1 µl and 25 µl blood, 1 µl and 25 µl semen, and 5 µl and 25 µl saliva. The samples were aged at room temperature for two weeks prior to sampling. Deposited biological fluid samples were collected via swabbing with moistened foam swabs. Extraction was performed using the bead beating extraction reagents included in the RAZOR® EX Human Identification System kit. All of the samples were amplified on RAZOR® EX 1218 with the 35MINRN4 protocol.

saliva samples were not consistently higher for either the 5 µl or 25 µl samples. Based on the mean fluorescence values obtained from the inhibition control, excess semen may have an inhibitory effect on the TaqMan assays. In general, the biological fluid samples generated full and correct SNP profiles (Table 19). Three 25 µl and two 1 µl blood samples produced full SNP profiles. One 1 µl blood sample exhibited allelic dropout with SNP assays rs2291395 alleles A and G, rs12480506 allele A, and rs315791 allele A. All of the semen and saliva samples generated full SNP profiles.

Conclusions:

The RAZOR® EX Human Identification System can successfully generate the expected SNP profiles from dried blood, semen, and saliva stains. Very small volumes of biological fluids are necessary for the system to be effective; however, care must be taken when collecting samples to ensure that neither too much nor too little biological material is being collected.

TABLE 9

| | | Blood | | | | Semen | | |
| --- | --- | --- | --- | --- | --- | --- | --- | --- |
| SNP | Allele | DNA (μl) | Exp. + Calls | +Calls | $\overline{\text{RFU}}$ | DNA (μl) | Exp. + Calls | +Calls |
| rs9866013 | C | 1 | 3 | 3 | 466.67 ± 276.50 | 1 | 0 | 0 |
| | | 25 | 3 | 3 | 609.67 ± 28.15 | 25 | 0 | 0 |
| | T | 1 | 3 | 3 | 564.00 ± 329.37 | 1 | 3 | 3 |
| | | 25 | 3 | 3 | 714.00 ± 114.37 | 25 | 3 | 3 |
| rs1019029 | C | 1 | 0 | 0 | 15.67 ± 27.14 | 1 | 3 | 3 |
| | | 25 | 0 | 0 | 3.00 ± 5.20 | 25 | 3 | 3 |
| | T | 1 | 3 | 3 | 750.00 ± 203.93 | 1 | 3 | 3 |
| | | 25 | 3 | 3 | 797.00 ± 105.53 | 25 | 3 | 3 |
| rs2291395 | A | 1 | 3 | 2 | 317.00 ± 277.96 | 1 | 3 | 3 |
| | | 25 | 3 | 3 | 568.00 ± 128.49 | 25 | 3 | 3 |
| | G | 1 | 3 | 2 | 381.33 ± 320.75 | 1 | 3 | 3 |
| | | 25 | 3 | 3 | 705.00 ± 160.73 | 25 | 3 | 3 |
| rs12480506 | A | 1 | 3 | 2 | 475.67 ± 411.41 | 1 | 3 | 3 |
| | | 25 | 3 | 3 | 722.33 ± 93.55 | 25 | 3 | 3 |
| | G | 1 | 0 | 0 | 40.67 ± 36.68 | 1 | 0 | 0 |
| | | 25 | 0 | 0 | 48.33 ± 34.82 | 25 | 0 | 0 |
| rs315791 | A | 1 | 3 | 2 | 380.00 ± 357.24 | 1 | 3 | 3 |
| | | 25 | 3 | 3 | 721.00 ± 298.38 | 25 | 3 | 3 |
| | C | 1 | 3 | 3 | 602.00 ± 262.78 | 1 | 3 | 3 |
| | | 25 | 3 | 3 | 756.67 ± 160.86 | 25 | 3 | 3 |
| Human-Specific Control | | 1 | 3 | 3 | 594.33 ± 322.10 | 1 | 3 | 3 |
| | | 25 | 3 | 3 | 754.33 ± 152.55 | 25 | 3 | 3 |
| Inhibition Control | | 1 | 3 | 3 | 1027.67 ± 141.2 | 1 | 3 | 3 |
| | | 25 | 3 | 3 | 889.00 ± 48.07 | 25 | 3 | 3 |

| | | Semen | Saliva | | | |
| --- | --- | --- | --- | --- | --- | --- |
| SNP | Allele | $\overline{\text{RFU}}$ | DNA (μl) | Exp. + Calls | +Calls | $\overline{\text{RFU}}$ |
| rs9866013 | C | 37.00 ± 6.56 | 5 | 0 | 0 | 41.00 ± 5.29 |
| | | 0.00 ± 0.00 | 25 | 0 | 0 | 43.00 ± 8.66 |
| | T | 1107.00 ± 41.04 | 5 | 3 | 3 | 962.67 ± 134.58 |
| | | 428.33 ± 51.16 | 25 | 3 | 3 | 1,190.33 ± 128.81 |
| rs1019029 | C | 537.67 ± 24.79 | 5 | 3 | 3 | 892.00 ± 107.09 |
| | | 190.33 ± 50.93 | 25 | 3 | 3 | 871.67 ± 29.14 |
| | T | 640.00 ± 15.72 | 5 | 0 | 0 | 85.33 ± 28.02 |
| | | 221.67 ± 17.62 | 25 | 0 | 0 | 58.67 ± 4.93 |
| rs2291395 | A | 539.00 ± 16.64 | 5 | 3 | 3 | 468.33 ± 59.16 |
| | | 134.33 ± 18.01 | 25 | 3 | 3 | 647.67 ± 83.26 |
| | G | 757.00 ± 86.02 | 5 | 3 | 3 | 681.00 ± 127.47 |
| | | 176.00 ± 33.18 | 25 | 3 | 3 | 837.33 ± 124.02 |
| rs12480506 | A | 939.33 ± 147.85 | 5 | 3 | 3 | 737.33 ± 112.45 |
| | | 217.67 ± 58.50 | 25 | 3 | 3 | 644.33 ± 51.19 |
| | G | 62.67 ± 13.32 | 5 | 0 | 0 | 73.33 ± 19.55 |
| | | 0.00 ± 0.00 | 25 | 0 | 0 | 78.33 ± 24.01 |
| rs315791 | A | 622.33 ± 20.40 | 5 | 3 | 3 | 539.67 ± 67.87 |
| | | 230.33 ± 34.02 | 25 | 3 | 3 | 529.33 ± 37.85 |
| | C | 837.00 ± 70.45 | 5 | 3 | 3 | 681.33 ± 34.39 |
| | | 425.00 ± 57.03 | 25 | 3 | 3 | 774.00 ± 93.55 |
| Human-Specific Control | | 966.00 ± 54.62 | 5 | 3 | 3 | 754.67 ± 110.21 |
| | | 396.00 ± 67.67 | 25 | 3 | 3 | 736.67 ± 240.28 |
| Inhibition Control | | 1038.67 ± 115.48 | 5 | 3 | 3 | 1,012.00 ± 100.26 |
| | | 378.33 ± 70.44 | 25 | 3 | 3 | 942.33 ± 134.80 |

Notes:
RFU: mean fluorescence value;
+calls: positive calls

Example 7: Controls

A. Human-Specific Control
Description:
The human-specific control was assessed by examining DNA from four different non-human species.
Procedure:
Twenty-five microliters of non-human blood were spotted on foam swabs in triplicate. The swabs were extracted using the bead beating extraction procedure included in the RAZOR® EX Human Identification System kit. The resulting fluorescence values were compared to those obtained from 5 ng/well of purified human DNA from a donor who was heterozygous for each SNP.

Results and Discussion:
Only rhesus monkey DNA had any significant cross reaction with the human-specific control (Table 20). This was not unexpected as the rhesus genome shares approximately 93% of its sequence with the human genome [10]. Other animal DNA showed little to no consistent cross reactivity (Table 20); however, one canine DNA sample generated a positive call for the human-specific control (174 RFU). Because this positive result was not replicated across the triplicate canine samples, it is not likely that it represents true cross reactivity of canine DNA with the human-specific control. The inconsistent results obtained with canine DNA may be due to low level exogenous human DNA contamination introduced into the pouches during the lyophilization process (see Example 8).

Conclusions:

The human-specific control in the RAZOR® EX Human Identification System is human-specific, but it does show some cross reactivity with higher primates. Little to no consistent cross reactivity is observed with non-primate animals. More stringent manufacturing processes may need to be considered to ensure the RAZOR® EX Human Identification System is free of human DNA contamination.

TABLE 10

Human-specific control assessment

| Species | Human-Specific Control RFU | Positive Calls |
|---|---|---|
| Rat | 29.67 ± 13.58 | 0 |
| Bovine | 27.67 ± 40.20 | 0 |
| Canine | 73.67 ± 90.01 | 1 |
| Rhesus Monkey | 123.00 ± 19.31 | 3 |
| Human | 944.67 ± 23.69 | 3 |

Notes:
RFU: mean fluorescence value

B. Inhibition Control

Description:

The inhibition control was assessed by examining purified DNA combined with various concentrations of known PCR inhibitors.

Procedure:

In triplicate, 5 ng purified DNA from a donor who was heterozygous for each SNP was combined with the following concentrations of humic acid, hematin, or indigo dye: 0 ng, 500 ng, 1,000 ng, 1,500 ng, and 2,000 ng humic acid; 100 uM, 200 uM, 300 uM, and 400 uM hematin, and 1 mM, 2 mM, 4 mM, and 10 mM indigo dye. All samples were amplified on RAZOR® EX 1218 with the 35MINRN4 protocol.

Results and Discussion:

In general, DNA samples exhibited a decrease in mean fluorescence value as the amount of inhibitor increased (Table 21). For humic acid and indigo dye inhibited samples in which one or more SNP alleles dropped out, the inhibition control also failed to amplify; however, for two of the hematin inhibited samples, the inhibition control amplified successfully while some of the other assays failed to produce results (Table 22).

Conclusions:

The presence of the inhibition control allows for the detection of PCR inhibitors in the sample. Because the inhibition control PCR reagents contain a synthetic non-human oligonucleotide that functions as the template DNA, the inhibition control should consistently produce high fluorescence values. In instances where the inhibition control produces low fluorescence values or fails to amplify, it is likely that a PCR inhibitor is present.

TABLE 11

Mean fluorescence values generated by the inhibition control

| Inhibitor | Amount | RFU |
|---|---|---|
| Humic Acid | 0 ng | 896.00 ± 45.30 |
| | 500 ng | 920.00 ± 168.68 |
| | 1000 ng | 851.33 ± 177.70 |
| | 1500 ng | 275.83 ± 232.84 |
| | 2000 ng | 69.00 ± 9.17 |
| Hematin | 0 μM | 896.00 ± 45.30 |
| | 100 μM | 875.00 ± 118.51 |
| | 200 μM | 518.00 ± 435.60 |
| | 300 μM | 428.17 ± 735.41 |
| | 400 μM | 53.67 ± 20.55 |
| Indigo Dye | 0 mM | 896.00 ± 45.30 |
| | 1 mM | 894.33 ± 31.56 |
| | 2 mM | 859.67 ± 174.74 |
| | 4 mM | 394.33 ± 51.05 |
| | 10 mM | 136.33 ± 112.61 |

TABLE 12

Positive calls generated by the inhibited DNA samples

| | | | Humic Acid | | | | | Hematin | | | | | Indigo Dye | | | | |
|---|---|---|---|---|---|---|---|---|---|---|---|---|---|---|---|---|---|
| SNP | Allele | Exp. + Call | 0 ng | 500 ng | 1000 ng | 1500 ng | 2000 ng | 0 μM | 100 μM | 200 μM | 300 μM | 400 μM | 0 mM | 1 mM | 2 mM | 4 mM | 10 mM |
| rs9866013 | C | + | 3 | 3 | 3 | 3 | 0 | 3 | 3 | 3 | 1 | 0 | 3 | 3 | 3 | 3 | 1 |
| | T | + | 3 | 3 | 3 | 3 | 0 | 3 | 3 | 3 | 2 | 0 | 3 | 3 | 3 | 3 | 2 |
| rs1019029 | C | + | 3 | 3 | 3 | 3 | 0 | 3 | 3 | 3 | 2 | 0 | 3 | 3 | 3 | 3 | 2 |
| | T | + | 3 | 3 | 3 | 3 | 1 | 3 | 3 | 3 | 2 | 0 | 3 | 3 | 3 | 3 | 2 |
| rs2291395 | A | + | 3 | 3 | 3 | 3 | 0 | 3 | 3 | 3 | 2 | 0 | 3 | 3 | 3 | 3 | 1 |
| | G | + | 3 | 3 | 3 | 3 | 3 | 3 | 3 | 3 | 2 | 0 | 3 | 3 | 3 | 3 | 0 |
| rs12480506 | A | + | 3 | 3 | 3 | 3 | 0 | 3 | 3 | 3 | 1 | 0 | 3 | 3 | 3 | 3 | 0 |
| | G | + | 3 | 3 | 3 | 3 | 1 | 3 | 3 | 3 | 2 | 0 | 3 | 3 | 3 | 3 | 0 |
| rs315791 | A | + | 3 | 3 | 3 | 3 | 0 | 3 | 3 | 3 | 1 | 0 | 3 | 3 | 3 | 3 | 1 |
| | C | + | 3 | 3 | 3 | 3 | 0 | 3 | 3 | 3 | 1 | 0 | 3 | 3 | 3 | 3 | 1 |
| Human-Specific Control | | + | 3 | 3 | 3 | 3 | 0 | 3 | 3 | 3 | 0 | 0 | 3 | 3 | 3 | 3 | 2 |
| Inhibition Control | | + | 3 | 3 | 3 | 3 | 0 | 3 | 3 | 3 | 2 | 0 | 3 | 3 | 3 | 3 | 0 |

Example 8: Assessment of Contamination

Description:

The presence of exogenous DNA originating from reagents, consumables, the operator, and/or the environment was evaluated.

Procedure:

Three RAZOR Human Identification Pouches were rehydrated with the bead beating extraction reagents included in the RAZOR® EX Human Identification System kit. Each pouch was run on RAZOR® EX 1218 with the 35MINRN4 protocol.

Results and Discussion:

Two of the three pouches produced the expected results with no amplification observed for any TaqMan assay except the inhibition control (Table 23). The third pouch generated a false positive with the TaqMan probe for rs1019029 allele T (159 RFU), which indicated the presence of exogenous DNA. It is unlikely that the extraction reagents were the source of the contamination as the same reagent mix was used to rehydrate all three pouches. Although the source of the contamination is unknown, it is possible that low level exogenous human DNA was introduced into some of the pouches during lyophilization. Similar false positives resulting from exogenous DNA were observed during species specificity testing, repeatability testing, and reproducibility testing.

Conclusions:

The majority of the TaqMan assays did not exhibit any contamination resulting from exogenous DNA. During contamination assessment, a single RAZOR Human Identification Pouch generated a positive SNP call for SNP assay rs1019029 allele T, which indicated the presence of exogenous DNA in that reaction. As this call was not consistently observed, it is likely that low level exogenous human DNA was introduced into some of the pouches during lyophilization. More stringent manufacturing processes may need to be considered to ensure the RAZOR® EX Human Identification System is free of human DNA contamination.

TABLE 13

Contamination assessment results

| SNP | Allele | Contamination RFU | + Calls |
|---|---|---|---|
| rs9866013 | C | 27.67 ± 15.37 | 0 |
|  | T | 11.33 ± 6.03 | 0 |
| rs1019029 | C | 24.33 ± 4.16 | 0 |
|  | T | 63.33 ± 83.51 | 1 |
| rs2291395 | A | 21.33 ± 6.43 | 0 |
|  | G | 18.67 ± 14.50 | 0 |
| rs12480506 | A | 17.00 ± 14.73 | 0 |
|  | G | 12.00 ± 9.64 | 0 |
| rs315791 | A | 17.67 ± 6.03 | 0 |
|  | C | 27.33 ± 14.29 | 0 |
| Human-Specific |  | 49.67 ± 15.28 | 0 |
| Inhibition |  | 1088.33 ± 30.62 | 3 |

Notes:
RFU: mean fluorescence value;
+ calls: positive calls

Example 9: Failure to Perform Rate and Error Rate

Description:

The results from various developmental validation studies were used to determine the failure to perform rate and error rate of the RAZOR® EX Human Identification System. For the purpose of this study, the failure to perform rate was defined as the frequency with which the inhibition control failed to produce an amplification result (false negative) or a mechanical error occurred that prevented the pouch from being operational. The error rate was defined as the frequency with which any RAZOR Human Identification Pouch did not generate the expected profile (false negatives or false positives were generated for any assay).

Procedure:

The failure to perform rate was determined by examining the data from all the pouches that did not contain inhibited samples. The samples that met these criteria were the species specificity samples, the sensitivity study samples, the stability study samples, the degraded DNA samples, the repeatability/reproducibility samples and the contamination assessment samples. In total, 144 pouches were examined for failed inhibition controls. Additionally, the number of pouches with failed vacuum seals was determined. From the lot of pouches used for developmental validation testing, 189 pouches were examined for functioning vacuum seals.

The error rate was determined by examining the data from pouches on which the recommended sample concentrations or volumes were used. Full and correct profiles were expected from these samples. The samples that met these criteria were the 0.1-10 ng sensitivity study samples, the 1 μl and 25 μl saliva stability study samples, and the repeatability/reproducibility samples. The blood and semen stability study samples were not included because it is recommended for the user to collect a volume between 1 μl and 25 μl. In total, 63 pouches were examined.

Results and Discussion:

Overall, one inhibition control failed to amplify and one vacuum seal failed to function (Table 24). The failed inhibition control was observed in a 0.01 ng/well sensitivity study sample (Table 9). The cause for the control failure is unknown. Based on these results, the failure to perform rate is <1%.

Of the 63 pouches examined for determining the error rate, only one pouch generated an incorrect call (Table 25). The incorrect call was a false positive obtained with rs12480506 allele G on RAZOR® EX 1218 during repeatability/reproducibility testing (Table 17 and Table 18). This false positive can most likely be attributed to low level exogenous human DNA that may have been introduced into some of the pouches during lyophilization. Based on these results, the error rate is 1.6%.

Conclusions:

The failure to perform rate of the RAZOR® EX Human Identification System is <1%. The error rate of the RAZOR® EX Human Identification System is 1.6%.

TABLE 14

RAZOR EX Human Identification System failure to perform rate

| N | Failed Inhibition Controls | Failure to Perform Rate (%) | N | Failed Vacuum Seal | Failure to Perform Rate (%) |
|---|---|---|---|---|---|
| 144 | 1 | 0.7% | 189 | 1 | 0.5% |

TABLE 15

RAZOR EX Human Identification System error rate

| Validation Study | N | Pouches with Incorrect Calls | ErrorRate (%) |
|---|---|---|---|
| Sensitivity 0.1 ng | 9 | 0 | 0% |
| Sensitivity 1.0 ng | 9 | 0 | 0% |
| Sensitivity 10 ng | 9 | 0 | 0% |
| Stability 5 μl saliva 0 weeks | 3 | 0 | 0% |
| Stability 5 μl saliva 1 week | 3 | 0 | 0% |
| Stability 5 μl saliva 2 weeks | 3 | 0 | 0% |

TABLE 15-continued

RAZOR EX Human Identification System error rate

| Validation Study | N | Pouches with Incorrect Calls | ErrorRate (%) |
|---|---|---|---|
| Stability 25 μl saliva 0 weeks | 3 | 0 | 0% |
| Stability 25 μl saliva 1 week | 3 | 0 | 0% |
| Stability 25 μl saliva 2 weeks | 3 | 0 | 0% |
| Repeatability/Reproducibility | 18 | 1 | 5.6% |
| Total | 63 | 1 | 1.6% |

Notes:
N: number of pouches examined

One skilled in the art would readily appreciate that the methods, compositions, and products described herein are representative of exemplary embodiments, and not intended as limitations on the scope of the disclosure. It will be readily apparent to one skilled in the art that varying substitutions and modifications may be made to the present disclosure disclosed herein without departing from the scope and spirit of the disclosure.

The present disclosure illustratively described herein suitably may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

REFERENCES

[1] J. J. Kim, P. Verdu, A. J. Pakstis, W. C. Speed, J. R. Kidd and K. K. Kidd, "Use of autosomal loci for clustering individuals and populations of East Asian origin," *Human Genetics*, vol. 117, pp. 511-9, 2005.

[2] K. K. Kidd, A. J. Pakstis, W. C. Speed, E. L. Grigorenko, S. L. Kajuna, N. J. Karoma, S. Kungulilo, J. J. Kimi, R. B. Lu, A. Odunsi, F. Okonofua, J. Parnas, L. O. Schulz, O. V. Zhukova and J. R. Kidd, "Developing a SNP panel for forensic identification of individuals," *Forensic Science International*, vol. 164, pp. 20-32, 2006.

[3] A. J. Pakstis, W. C. Speed, J. R. Kidd and K. K. Kidd, "Candidate SNPs for a universal individual identification panel," *Human Genetics*, vol. 121, pp. 305-17, 2007.

[4] A. J. Pakstis, W. C. Speed, R. Fang, F. C. Hyland, M. R. Furtado, J. R. Kidd and K. K. Kidd, "SNPs for a universal individual identification panel," *Human Genetics*, vol. 127, pp. 315-24, 2010.

[5] S. Ueda, K. Washio and K. Kurosaki, "Human-specific sequences: isolation of species-specific DNA regions by genome subtraction," *Genomics*, vol. 8, pp. 7-12, 1990.

[6] S. Ueda and Y. Watanabe, "Characterization of human-specific DNA sequences obtained by genome substraction," *Human Evolution*, vol. 10, no. 1, pp. 63-68, 1995.

[7] S. F. Altschul, W. Gish, W. Miller, E. W. Myers and D. J. Lipman, "Basic local alignment search tool," *Journal of Molecular Biology*, vol. 215, pp. 403-410, 1990.

[8] R. I. Tang, A. Dodd, W. C. McNabb and D. R. Love, "Validation of zebrafish (*Danrio rerio*) reference genes for quantitative real-time RT-PCR normalization," *Acta*, vol. 39, no. 5, pp. 384-390, Biochimica et Biophysica Sinica.

[9] A. T. McCurley and G. V. Callard, "Characterization of housekeeping genes in zebrafish: male-female differences and effects of tissue type, developmental stage and chemical treatment," *BMC Molecular Biology*, vol. 9, no. 102, 2008.

[10] R. A. Gibbs and et al, "Evolutionary and biomedical insights from the rhesus macaque genome," *Science*, vol. 316, pp. 222-34, 2007.

What is claimed is:

1. A self-contained system for constructing a nucleic acid profile of a human individual in a field forward position, the system comprising:
   a) a reagent kit, the kit comprising:
      i) means for isolating a nucleic acid sample from a biological material obtained from the individual;
      ii) means for amplifying between five and twenty-one nucleic acid amplification products from the nucleic acid sample in i), wherein each amplification product comprises a single nucleotide polymorphism (SNP) suitable for constructing the nucleic acid profile of a human individual, and further wherein the five to twenty-one nucleic acid amplification products comprise the SNPs rs9866013, rs1019029, rs2291395, rs12480506, and rs315791; and
      iii) means for determining the genotypes of the SNP in the five to twenty-one amplification products, wherein determining the genotypes of the SNP in the five to twenty-one amplification products constructs the nucleic acid profile of the human individual; and
   b) an instrument for nucleic acid amplification and detection, wherein the instrument is compatible with the kit in a),
wherein the self-contained system is capable of constructing a nucleic acid profile capable of identification of the individual with a power of discrimination of more than 98%.

2. The system of claim 1, wherein the self-contained system further comprises means for collecting the biological material.

3. The system of claim 2, wherein the means for collecting the biological material is a foam swab with a point of breakage.

4. The system of claim 1, wherein the means for isolating the nucleic acid sample from the biological material comprise at least one mechanical lysis agent and at least one chemical cell lysis agent, wherein the mechanical lysis agent and the chemical lysis agent can be used in combination; a neutralizing agent, wherein the neutralizing agent neutralizes the chemical lysis agent and a diluting agent.

5. The system of claim 4, wherein the means for isolating the nucleic acid sample from the provided biological material comprises a 5 ml vial comprising 600 μl NaOH at pH 12.5 and 1150 mg zirconium beads, and a double barreled syringe comprising 1780 μl water in a first barrel, and 120 μl neutralization buffer in a second barrel.

6. The system of claim 1, wherein the means for amplifying and the means for determining the genotypes is:
   a) a single reagent-containing disposable comprising reagents for amplifying a nucleic acid amplification product comprising a single SNP and for determining the genotype of the SNP using Real Time PCR, and
   b) a means for introducing the sample to the reagent-containing disposable.

7. The system of claim 6, wherein the single reagent-containing disposable is a PCR vessel having:
   a) at least one slot comprising one or more reagents for amplification of a human-specific control;
   b) at least one slot containing one or more reagents for an inhibition control; and
   c) at least five slots, each slot comprising reagents for amplifying a nucleic acid amplification product comprising a single SNP and for determining the genotype of the SNP using real time PCR.

8. The system of claim 6, wherein the single reagent-containing disposable is a PCR vessel comprising more than one slot, and wherein
   a) a first slot comprises reagents for amplification of a human-specific control;
   b) a second slot comprises reagents for an inhibition control; and
   c) at least ten slots, wherein each two slots of the at least ten slots comprise reagents for amplification of a single nucleic acid amplification product comprising a single SNP, and wherein a first of each two slots comprises one or more reagents for determining a first allele of the SNP, and a second of each two slots comprises reagents for determining a second allele of the SNP.

9. The system of claim 6, wherein the reagents are lyophilized.

10. The system of claim 1, wherein a SNP suitable for constructing the nucleic acid profile has a heterozygosity of more than 0.4, and an Fst of less than 0.06.

11. The system of claim 1, wherein the five to twenty-one nucleic acid amplification products comprise five to twenty-one SNPs selected from rs9866013, rs1019029, rs2291395, rs12480506, rs315791, rs12997453, rs7041158, rs2272998, rs13134862, rs3780962, rs433342, rs9546538, rs16891982, rs310644, rs1426654, rs3827760, rs4891825, rs4918664, rs10497191, rs12913832, rs1876482, and combinations thereof.

12. The system of claim 1, wherein the system comprises:
   a) a 5 ml vial comprising 600 μl NaOH at pH of 12.5 and 1150 mg zirconium beads, and a double barreled syringe comprising 1780 μl water in a first barrel, and 120 μl neutralization buffer in a second barrel;
   b) a reagent pouch for use with the instrument for nucleic acid amplification and detection, wherein the reagent pouch comprises freeze-dried reagents for amplifying nucleic acid amplification products comprising the rs9866013, rs1019029, rs2291395, rs12480506, and rs315791 SNPs and determining the genotypes of the SNPs, and reagents for amplification of the HS5 human-specific control, and a beta actin inhibition control;
   c) a 3 ml syringe; and
   d) the instrument for nucleic acid amplification and detection.

13. The system of claim 1, wherein the system comprises:
   a) a 5 ml vial comprising 600 μl NaOH at pH of 12.5 and 1150 mg zirconium beads, and a double barreled syringe comprising 1780 μl water in a first barrel, and 120 μl neutralization buffer in a second barrel;

b) a reagent pouch for use with the instrument for nucleic acid amplification and detection, the reagent pouch comprising:
  i) a first slot comprising freeze-dried reagents for amplifying and determining the presence of an HS5 human-specific control;
  ii) a second slot comprising freeze-dried reagents for amplifying and determining the presence of a βactin1 inhibition control; and
  iii) at least ten slots, wherein each two slots of the at least ten slots comprise freeze-dried reagents for amplification of a single nucleic acid amplification product selected from the rs9866013, rs1019029, rs2291395, rs12480506, and rs315791 SNPs, and wherein a first of each two slots comprises one or more reagents for determining a first allele of each SNP, and a second of each two slots comprises reagents for determining a second allele of each SNP;
c) a 3 ml syringe; and
d) an instrument for nucleic acid amplification and detection.

14. The system of claim 13, wherein the reagent pouch comprises
  a) a first slot comprising freeze-dried reagents for amplifying and determining the presence of an HS5 human-specific control, the freeze-dried reagents comprising a forward primer of SEQ ID NO: 24, a reverse primer of SEQ ID NO: 25, and a TaqMan probe of SEQ ID NO: 26;
  b) a second slot comprising freeze-dried reagents for amplifying and determining the presence of a βactin1 inhibition control, the freeze-dried reagents comprising a forward primer of SEQ ID NO: 27, a reverse primer of SEQ ID NO: 28, a TaqMan probe of SEQ ID NO: 29, and a template of SEQ ID NO: 30;
  c) a third slot comprising freeze-dried reagents for amplifying and determining a C allele of the rs9866013 SNP, the freeze-dried reagents comprising a forward primer of SEQ ID NO: 31, a reverse primer of SEQ ID NO: 32, and a TaqMan probe of SEQ ID NO: 33;
  d) a fourth slot comprising freeze-dried reagents for amplifying and determining a T allele of the rs9866013 SNP, the freeze-dried reagents comprising a forward primer of SEQ ID NO: 31, a reverse primer of SEQ ID NO: 32, and a TaqMan probe of SEQ ID NO: 34;
  e) a fifth slot comprising freeze-dried reagents for amplifying and determining a C allele of the rs1019029 SNP, the freeze-dried reagents comprising a forward primer of SEQ ID NO: 35, a reverse primer of SEQ ID NO: 36, and a TaqMan probe of SEQ ID NO: 37;
  f) a sixth slot comprising freeze-dried reagents for amplifying and determining a T allele of the rs1019029 SNP, the freeze-dried reagents comprising a forward primer of SEQ ID NO: 35, a reverse primer of SEQ ID NO: 36, and a TaqMan probe of SEQ ID NO: 38;
  g) a seventh slot comprising freeze-dried reagents for amplifying and determining a A allele of the rs2291395 SNP, the freeze-dried reagents comprising a forward primer of SEQ ID NO: 39, a reverse primer of SEQ ID NO: 40, and a TaqMan probe of SEQ ID NO: 41;
  h) an eighth slot comprising freeze-dried reagents for amplifying and determining a G allele of the rs2291395 SNP, the freeze-dried reagents comprising a forward primer of SEQ ID NO: 39, a reverse primer of SEQ ID NO: 40, and a TaqMan probe of SEQ ID NO: 42;
  i) a ninth slot comprising freeze-dried reagents for amplifying and determining an A allele of the rs12480506 SNP, the freeze-dried reagents comprising a forward primer of SEQ ID NO: 43, a reverse primer of SEQ ID NO: 44, and a TaqMan probe of SEQ ID NO: 45;
  j) a tenth slot comprising freeze-dried reagents for amplifying and determining a G allele of the rs12480506 SNP, the freeze-dried reagents comprising a forward primer of SEQ ID NO: 43, a reverse primer of SEQ ID NO: 44, and a TaqMan probe of SEQ ID NO: 46;
  k) an eleventh slot comprising freeze-dried reagents for amplifying and determining an A allele of the rs315791 SNP, the freeze-dried reagents comprising a forward primer of SEQ ID NO: 47, a reverse primer of SEQ ID NO: 48, and a TaqMan probe of SEQ ID NO: 49; and
  l) a twelfth slot comprising freeze-dried reagents for amplifying and determining a C allele of the rs315791 SNP, the freeze-dried reagents comprising a forward primer of SEQ ID NO: 47, a reverse primer of SEQ ID NO: 48, and a TaqMan probe of SEQ ID NO: 50.

* * * * *

SEQUENCE LISTING

```
<160> NUMBER OF SEQ ID NOS: 50

<210> SEQ ID NO 1
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 1
ctggtccaca ggaaatctgt cacaataaga tataaggttt tcagactgag attcgtaaac     60
aaaactcctc aaaaattgta ctttgatcca aatgcagatt catatagtgc cttcagaacc    120
tttgagatct gattctattt ttaaagcttc ttagaagaga gattgcaaag tgggttgttt    180
ctctagccag acagggcagg naaatagggg tggctggtgg gatgggagtt catttgcacc    240
catgtacaaa ttgctggggg tcatggtgag ctggaaacct acagccctca gctgcagcca    300
gtggctgctg tgcagtggga atatgggtca gatcagtgag agctttaagt ttcttagagg    360
acatggaaac ctgtaatttt taagcaggga atttcacaac t                        401
```

<210> SEQ ID NO 2
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 2

```
tgatggtgcc attgcactcc agcctgggcg atggagcaag actccatcaa aaaaaaaaaa      60
aatgcgtgaa catatgtaat tagagaaaaa tattagggaa attgcaaaat aatttattag     120
ccttattcag atctagagat gatcaaggat aagctcagcc tactcaagca gagataacgt     180
ctgtgtggaa acgctaaatg nctagtctgc ttctatcttg tgtttaaagg agaatcctgt     240
tgaaaatgaa gccactatca tggttaagag gatttgaaat ctaagatcag gagtgactgc     300
tttcggtgaa tacaagtttc taagactaga agatggacat tctaaagttc agaaaagtc      360 acttctcaaa tcactaagtt atgttgcttc cttcacaatg t                         401
```

<210> SEQ ID NO 3
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 3

```
ctcctgcccc tccagccccc ggggagcggg gtcttcaggg tacaaggtgg gccgagtgat      60
gccatctgac ctcaatttaa tggctgacaa ctcacagcct gaaaatgaaa aggaagcttc     120
aggtggagac agcccgaagg taaaggcttt gtagccttga agcagcccct gggggacagt     180
gtgtagccac agggccctca ntgtcacctg cctgtcactc acctgcctgt ccagtgacag     240
ccctgccagg gcatcggtgg ggatgtgggc ttgattctgg tgttgctgct gtgttcttgg     300
tattggggct ttttgcaagt gtactcgttt agtcattcaa cgcacatctt agggtctccc     360
taatagctgt aggcccaggt gctgagggct gggcagacag c                         401
```

<210> SEQ ID NO 4
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 4

```
gaggcagggg aaggaagcag ggagaggaaa ggaggagaga aggaggaagc aggagagagg      60
gaagagagtg tggtgttggg taagtcacca cccctatcta caacatttac tgggcacctc     120
ctgacgttgg aacagtcgcc accatctgtg tgctaaccgg ctgtgggagg agacagcttc     180
ttgaacaaat tcgtgtccct ntgctagtca ggccctgggt tctaagctca caacatggat     240
tttggtggct aaagttttt ttttccccca caggactatg ttagctgtct ttaaaagaag      300
aaaaaagaaa taggcacggt gtggaatact cagtaagtag acaaatttta ccgagtaaaa     360
ttactgagta actcacagac agtacaactc acccttttcca a                        401
```

<210> SEQ ID NO 5
<211> LENGTH: 403
<212> TYPE: DNA
<213> ORGANISM: Homo sapiens
<220> FEATURE:
<221> NAME/KEY: misc_feature
<222> LOCATION: (203)..(203)
<223> OTHER INFORMATION: n is a or c

<400> SEQUENCE: 5

```
tatatttatt gaacacctgc tatgtgctaa agaatgtaat gggattcagg agtgaacaaa      60
cataaagtca tcgatctcat ggagactaat aatgataatg ttataataat ggtgatgatg     120
atggtgatta atgagcattg agtatttact ttgtaccagg ggtgtttccc ttactgtaaa     180
atgaggaaac taatgcatag gcnagtttca tccttatgtg gcagacagaa attaacaaag     240
gagcaaataa gaggtgcgag ggctctatgt acaatttggt agccactagc ctggctattt     300
aaatctaaag tcatggaaat gcaataaaat tcaaaattca gttccttggt cacacatatt     360
tcaaatgctc aacacttaca catatccagt ggcagtcact tcg                       403
```

<210> SEQ ID NO 6
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 6

```
ggggaaggaa gggaggaaag aaggaaggaa aaagagaaaa aggctgagtg agtagttgtt      60
tgcttactag gacctgtaag agtctgtgat tctatattct ttactactat gttagaaaaa     120
taaccaaaga tcctaagtct gatcaattgt ttgtcagaat gttttatgct ttaaagatac     180
aggttatctg tattacattg ngttttttacc tacctttctt gcacatcatc agagctgtta    240
aatggtaaaa atgatatttc acagtcttct gccctaaaat gtaatgaaat ttgttattaa     300
cagtcattga acctgggata caattttttgg tttaagaaaa agacttactt aagttttgcc    360
agtgccttaa caacagcaaa atctctccgt tggttagggg a                         401
```

<210> SEQ ID NO 7
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 7

```
ccttgaaatt ccccccaaca cttcccaggc catcctgaat atcccagcaa acagagcaga      60
agaaaggtga atgaagatat caagtgcaga cagactccag tgaggtgaaa attgcaatgg     120
tgagaggttg atggtaaaat caaacggaac ttgttatttt gtcattctga tggactggaa     180
ctgaggattt tcaatttcct ntccaaccca agacacttct cactggaaaa ctctcacaat     240
cacatttata acaaaggaga ggcaatgtta ttcctcagaaa ttccttttag aaagtaaact    300
gccttgttgg ggaaagtatt tcttctgggt ggtagatgac taggccctga ggaaattggt    360
ttaggctgaa tcttacttaa caaaccttgg ggtggagctg g                         401
```

<210> SEQ ID NO 8

```
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or g or t

<400> SEQUENCE: 8
atttgtcttt ctcgcgtgtg acatgtttgg aagtcccgtt aaactggcat ctgttctgtt      60
ttaggagaaa cccgatgcta gccccacgtc acttcagctg cggtcccaga tcgaagtaag     120
cacaatgact ttaatcatct agttttgctt ctgccttttt ttttaagtg  acactctgta     180
caaatcagat gaagcctgct nctctgacca cactgactat acgaatcttc tctcgtagga    240
gtcgcttggc ttctgtagcg ccgtgtcaac cccagaagtg gaaagaaagt aagtctttct    300
ccctctgccc aggaccacct tccaagaagg tgtcttttag gtccatgctg acggaaatca    360
aacaggcgat catgtgcgta tgtactatgg agttatgcga t                        401

<210> SEQ ID NO 9
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 9
ttgagaaata tagccacagt ccaaagatta tctataacta taatgaagct attttaaaac      60
ataaatcagg aataatacac tattaaactc tgtacgaagc acttgaattg cttacagtga    120
ttcttgccta aggatgaaca gcaattttc  aagcccacac ctccagatga gagtcagata    180
tatcttagat gaagcaatag ngtcaagagt agaaatttca gtaggagagc tataccaaga    240
agacctgttc atccttgcct tatagattta tttaatgaac taaaagcaat gacaaacttt    300
catgatatac ctaagacaaa aatgtttaat tcccaaaaaa gacttggtgc aaaagactat    360
caagaatgtg cagctccaaa aagactgatt ttcaaacaaa a                        401

<210> SEQ ID NO 10
<211> LENGTH: 401
<212> TYPE: DNA
<213> ORGANISM: Homo sapiens

<400> SEQUENCE: 10
cagcaccgtg acacaactgt ccctcatgtg tgtttccaac attattgacc ctgggtccaa      60
aaatgggcat tgtttgagct gtttgtctac tggcaatgat ggatctgcat tgatccttcc    120
aaaccctctg tcctggttct gtgactggtg gtgtgtattc tgcggtagcg ggcttttgaa    180
gaaaaacact aacctgtcct cacgggtgaa agctgtatatc ttgaccttgt tcatcccatg    240
tttctttgtt tttgaggatt attattgtta tttttaatgt atctaagttt tttaaaagtt    300
gtctttaac  ttaaaaaatt atgtcatttt tttcacaaat tgttagattg gtagaaaagt    360
aatttgccat cactttcagt ggcaaaaact tcaattactt t                        401

<210> SEQ ID NO 11
<211> LENGTH: 401
<212> TYPE: DNA
<213> ORGANISM: Homo sapiens
<220> FEATURE:
<221> NAME/KEY: misc_feature
```

<222> LOCATION: (201)..(201)
<223> OTHER INFORMATION: n is a or c or g

<400> SEQUENCE: 11

```
ttcaaaattt atacaacatc caatcatttc tcaccacctc tattgctaat gtctggccca      60
agctaccaat ggaagattcc aaacaatttt ttagaattac aatgagacaa cattctatac     120
tgagcctttc ctgggcaaac cgggatattt ggtcattcac cgacaaagct ttacataatc     180
tgtgagcatc cacctcctca ncacatctct tttcccatca tttttgcctg ttctggctac     240
attggcctct ttggcatttt tggaaaaccc tgaaatacac agacttctca gggcgattgc     300
acttgctgtt ctctctacct ggaatgctct tctgaaaatc tctgtggttt gctccatgac     360
atccttcagg tctttgctca ggtattccct tcccagagat a                         401
```

<210> SEQ ID NO 12
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 12

```
aggggagggg ggcggagaag agagttgcta agaagctctg ctcgttccag cctggtgcac      60
tctgaaagat ctgacaccct ctgctgatct gcagtagcaa aaatccatct ggctagggaa     120
tgctgaaaga aaaaaaaatc aatccacgta cagggcaagc gttaaaaatg tgggcataaa     180
aggctgacga tctacataga ngcttatttt aaatggatta tttgattatt tttgcgtgct     240
ggaaacttta ccctttcctt tccttaacga gttcacagcc cccaccagct ccaccattcg     300
gaaaggagtg cttttaaaac atttatttcc caatggcttg aataaaatta gtgtcagggt     360
gtcaagcgaa cagcaatttg aggtaattat actgcacgcc a                         401
```

<210> SEQ ID NO 13
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or g

<400> SEQUENCE: 13

```
gatgctttat atggtccttt ttaaggtgat agttttcct gacgtccata gatttattaa      60
gaatctggta ttttaaacag taggaaatac acatagaaat atcaaatcca agttgtgcta     120
gaccagaaac tttagaaga catccttagg agagagaaag acttacaaga ataaagtgag     180
gaaaacacgg agttgatgca naagccccaa catccaacct cgactcctct ttcgtagatg     240
agaaactctg tggagttgtg tgcactatag ggatccccgc ggtacacaat ctgaaagaga     300
gattggaggc tgttgaggta caaatgcaat gtagtaagaa cccttctcat gcactctgct     360
tctccacctc tggggagcaa atgtccctgc ctgagggacc c                         401
```

<210> SEQ ID NO 14
<211> LENGTH: 401
<212> TYPE: DNA
<213> ORGANISM: Homo sapiens
<220> FEATURE:
<221> NAME/KEY: misc_feature
<222> LOCATION: (201)..(201)

<223> OTHER INFORMATION: n is a or g

<400> SEQUENCE: 14

```
aaaggatttg tcttctgcct tgtgaaagac agatgtcaga ctaatcaggc ttatccgatg      60
tgctacatga gatggaaagc gtgtgaaata gtaagtcaca ctaagtcttc tggaggttct     120
atttacgggt ttggttttga tatgaatgtt gcagaaactc tataaaattc ctagaaatct     180
gatacgttat cctatgatat ntatcctatc tcacatgcta ttcctagaaa tctggtgcaa     240
tgttatcagt cataattttg gttattacat aaaatgctg catgccacag aaataaccaa      300
gtttccttgc caaccgtgtc acgaatataa taaactctca tcagatcctg agccatggct     360
atcttaagtc ttcggtcatt cacagttatt atcttacttt g                         401
```

<210> SEQ ID NO 15
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 15

```
aatgaagtca taaagaagca aaacattgga ctcttttaat ctgtgtattt tattttctta     60
gtttaatagt ggttttatgt gaagctgtag ctttgagtat ctattgtgtt tagttgtaaa    120
gacatactct ttcactttat taggcataac aatcatttca tttatgttca gcccttggat    180
tgtctcagga tgttgcaggc ncaacttttca tggcagcggg cagttcagct cctgaattag   240
ttactgcttt cctaggtaaa tattgctcct tatacttctt gcttactcag tgtgattttt    300
attttcttca agttaacact aacttagctg gtactatctt gcacataggt gtatttatca   360
caaagggaga tattggcatt agcaccatcc ttggatctgc a                        401
```

<210> SEQ ID NO 16
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 16

```
ataatttaa aaaaattttt ttcaaataat ttttatttca tttaaataat ttttcagtgt      60
tgaccttcta ttgactgtga cttgcaacat ctaactgtgg ccattggtgt ctgtaggtct    120
tagccccacg gagctgccat ttgattgcct cgagaagact agccgaatgc tcagctccac   180
gtacaactct gagaaggctg ntgtgaaaac gtggcgccac ctcgccgaga gcttcggcct   240
gaagagggat gagattgggg gcatgacaga cggcatgcaa ctctttgacc gcatcagcac   300
ggcaggctac agcatccctg agctactcac aaaactggtg cagattgagc ggctggatgc   360
tgtggagtcc ttgtgtgcag acatactgga gtgggcgggg g                        401
```

<210> SEQ ID NO 17
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 17

```
atagcacagt tacttctttc aaaattgcta acataaaagc aggatttact ttctaaggaa    60
ataaggagag gtgggtggag ggaaggacag gcttacacca cacagtaaaa atgtgtccaa   120
aataagccag accctcaatc aagacaaact gcaactcaca taaaagtgta acaatctcaa   180
tcccccttaa tgttttcatc ngcttcattc agacacccat cctttaccaa ccctagagat   240
tcccctccc  ttcagatgtc tctcatcttg atggaattaa gcctctcagc catctggcct   300
caaaaacaaa gcttgctaca agcctaacaa tgaatgaaaa ggtaaagtat tctaatggct   360
taacaagttt tcagttcttt cttgttattc cacctgtgag t                      401
```

<210> SEQ ID NO 18
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 18

```
tggggaagca catcgtcata gagtggatga ccgccactgg gaaactgact catggctgaa    60
ataaggcaat agcttttcaag gcaggaatgg gagaaagcaa attatgagcc gagtgtactc  120
tggtgagtct gggagtgttt cctctcagct cagctatggt ggacacccaa aggtgggcag   180
agagagtaag agaaccctcaa ntcaccatgg agtcctccaa agaggaatct tttggtcaga  240
actcttgcca tgaagaaata atctgcccat aaaactaagt ttaggatggg tgtggtgtct   300
cacgcctgta atcccagcac tttgggaggc tgaggcgggg aggcttgctt gaggccagga   360
gtttgaggct agcctggaca acatagcaag accctgtctc t                      401
```

<210> SEQ ID NO 19
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 19

```
gtaattcaaa atgctaacaa gtgaaagaaa catctaatcc atgatgaaca tttccaagct    60
ttccctgaac catcaaaaat ctctctttcc aaaaaataat ctctctggca gtgggggcc   120
taagcacatg tgtagccaaa ctactcagtt atcctgcact gaaaaccacc cacatccttc   180
ccatttatag gcaatctctc ntacatcatc ataagcaaca atttcaacta ccaccacctc   240
ctcagcccca aggtctccaa tatccaccct cttcatcctt tcaccgaaca ctttctagaa   300
cagcaactac acaggcttcc tccatgtccc ccatccagtc ttcagtccac agtgttctgc   360
cttagtcaat ccagtgaaat accccttgtt aaggttctac g                      401
```

<210> SEQ ID NO 20
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is a or g

<400> SEQUENCE: 20

```
gagctgtcca acaaaggaca agagtttcgt gtcttaattc aaaatgcccc caagtataac    60
tctgaaaaca tttctagtct tgtaatcaac atcagggtaa aaatcatgtg ttaatacaaa   120
ggtacaggaa caaagaattt gttcttcatg gctctctgtg tctgatccaa gaggcgaggc   180
cagtttcatt tgagcattaa ntgtcaagtt ctgcacgcta tcatcatcag gggccgaggc   240
ttctcttttgt ttttaattaa ttgttttttaa ctgtgagttt atatacactt gaagcagtat   300
acatttagaa atggtctact tgtcgtttct ttgattacta cccatgagac agtattagta   360
attctggcct atgaaattgg caaagaaaac taccagtggt g                        401
```

<210> SEQ ID NO 21
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: n is c or t

<400> SEQUENCE: 21

```
gccctctatt aaaactgtag gttgcatttg tatcttccaa gacaggtatt atcacaagct    60
tgcataggta tctatttcaa ctaagcaatg gtgatttcat acatcatctt gtttacaaag   120
tagttttccac ttggagcata gtgagctgtt gatagagctt ttgtggtggg aacccaggag   180
cacatcaatt gcagagacaa ncaccaatag tgagggtaca gcccatggca ttttctttat   240
gtgtcacgtg gtattataat ttctttgccc cagtttaata aagatggcaa tgcaatctgt   300
gctttctgta gacttctgga ggtgaagaca gcatcgtatg tccatgtccc tcagtgaaag   360
gattccatgt gggaatggct cctatatgag gatggagatc c                        401
```

<210> SEQ ID NO 22
<211> LENGTH: 96
<212> TYPE: DNA
<213> ORGANISM: Homo sapiens

<400> SEQUENCE: 22

```
gtatgaaggc agacacatac atgaatggaa catgatagag aacccagaaa taaaaccaca    60
cacctacagt catctgatct tcaacaaagt tgacaa                              96
```

<210> SEQ ID NO 23
<211> LENGTH: 90
<212> TYPE: DNA
<213> ORGANISM: Artificial Sequence
<220> FEATURE:
<223> OTHER INFORMATION: target nucleic acid

<400> SEQUENCE: 23

```
gagggacttc ctttgtctgg catatctgag gcgcgcgctg tcactagcgc ccaccagcgg    60
tcagactgta gaatgcagag caaaacagga                                     90
```

<210> SEQ ID NO 24
<211> LENGTH: 24
<212> TYPE: DNA
<213> ORGANISM: Artificial Sequence
<220> FEATURE:
<223> OTHER INFORMATION: nucleic acid primer

<400> SEQUENCE: 24

```
gtatgaaggc agacacatac atga                                           24
```

<210> SEQ ID NO 25
<211> LENGTH: 24
<212> TYPE: DNA
<213> ORGANISM: Artificial Sequence
<220> FEATURE:
<223> OTHER INFORMATION: nucleic acid primer

<400> SEQUENCE: 25
ttgtcaactt tgttgaagat caga                                        24

<210> SEQ ID NO 26
<211> LENGTH: 15
<212> TYPE: DNA
<213> ORGANISM: Artificial Sequence
<220> FEATURE:
<223> OTHER INFORMATION: nucleic acid probe

<400> SEQUENCE: 26
catgatagag aaccc                                                  15

<210> SEQ ID NO 27
<211> LENGTH: 20
<212> TYPE: DNA
<213> ORGANISM: Artificial Sequence
<220> FEATURE:
<223> OTHER INFORMATION: nucleic acid primer

<400> SEQUENCE: 27
gagggacttc ctttgtctgg                                             20

<210> SEQ ID NO 28
<211> LENGTH: 20
<212> TYPE: DNA
<213> ORGANISM: Artificial Sequence
<220> FEATURE:
<223> OTHER INFORMATION: nucleic acid primer

<400> SEQUENCE: 28
tcctgttttg ctctgcattc                                             20

<210> SEQ ID NO 29
<211> LENGTH: 15
<212> TYPE: DNA
<213> ORGANISM: Artificial Sequence
<220> FEATURE:
<223> OTHER INFORMATION: nucleic acid probe

<400> SEQUENCE: 29
tcactagcgc ccacc                                                  15

<210> SEQ ID NO 30
<211> LENGTH: 200
<212> TYPE: DNA
<213> ORGANISM: Artificial Sequence
<220> FEATURE:
<223> OTHER INFORMATION: nucleic acid oligonucleotide

<400> SEQUENCE: 30
gcgctgctgc cagggagagg cgtttcagca agcatgtgac catctggagt caacttcctg    60
ttttgctctg cattctacag tctgaccgct ggtgggcgct agtgacagcg cgcgcctcag   120
atatgccaga caaaggaagt ccctctgcat tctctcatta ttaccataaa aggcaatggt   180
ttgagccgct ttgcggctgc                                              200

```
<210> SEQ ID NO 31
<211> LENGTH: 20
<212> TYPE: DNA
<213> ORGANISM: Artificial Sequence
<220> FEATURE:
<223> OTHER INFORMATION: nucleic acid primer

<400> SEQUENCE: 31
tgcaaagtgg gttgtttctc                                              20

<210> SEQ ID NO 32
<211> LENGTH: 19
<212> TYPE: DNA
<213> ORGANISM: Artificial Sequence
<220> FEATURE:
<223> OTHER INFORMATION: nucleic acid primer

<400> SEQUENCE: 32
tgcaaatgaa ctcccatcc                                               19

<210> SEQ ID NO 33
<211> LENGTH: 13
<212> TYPE: DNA
<213> ORGANISM: Artificial Sequence
<220> FEATURE:
<223> OTHER INFORMATION: nucleic acid probe

<400> SEQUENCE: 33
acagggcagg caa                                                     13

<210> SEQ ID NO 34
<211> LENGTH: 16
<212> TYPE: DNA
<213> ORGANISM: Artificial Sequence
<220> FEATURE:
<223> OTHER INFORMATION: nucleic acid probe

<400> SEQUENCE: 34
cccctattta cctgcc                                                  16

<210> SEQ ID NO 35
<211> LENGTH: 22
<212> TYPE: DNA
<213> ORGANISM: Artificial Sequence
<220> FEATURE:
<223> OTHER INFORMATION: nucleic acid primer

<400> SEQUENCE: 35
gcctactcaa gcagagataa cg                                           22

<210> SEQ ID NO 36
<211> LENGTH: 20
<212> TYPE: DNA
<213> ORGANISM: Artificial Sequence
<220> FEATURE:
<223> OTHER INFORMATION: nucleic acid primer

<400> SEQUENCE: 36
gtggcttcat tttcaacagg                                              20

<210> SEQ ID NO 37
<211> LENGTH: 18
<212> TYPE: DNA
<213> ORGANISM: Artificial Sequence
<220> FEATURE:
<223> OTHER INFORMATION: nucleic acid probe
```

```
<400> SEQUENCE: 37
ctaaatgcct agtctgct                                                     18

<210> SEQ ID NO 38
<211> LENGTH: 17
<212> TYPE: DNA
<213> ORGANISM: Artificial Sequence
<220> FEATURE:
<223> OTHER INFORMATION: nucleic acid probe

<400> SEQUENCE: 38
cagactagac atttagc                                                      17

<210> SEQ ID NO 39
<211> LENGTH: 20
<212> TYPE: DNA
<213> ORGANISM: Artificial Sequence
<220> FEATURE:
<223> OTHER INFORMATION: nucleic acid primer

<400> SEQUENCE: 39
aggctttgta gccttgaagc                                                   20

<210> SEQ ID NO 40
<211> LENGTH: 20
<212> TYPE: DNA
<213> ORGANISM: Artificial Sequence
<220> FEATURE:
<223> OTHER INFORMATION: nucleic acid primer

<400> SEQUENCE: 40
gacaggcagg tgagtgacag                                                   20

<210> SEQ ID NO 41
<211> LENGTH: 16
<212> TYPE: DNA
<213> ORGANISM: Artificial Sequence
<220> FEATURE:
<223> OTHER INFORMATION: nucleic acid probe

<400> SEQUENCE: 41
ccctcaatgt cacctg                                                       16

<210> SEQ ID NO 42
<211> LENGTH: 15
<212> TYPE: DNA
<213> ORGANISM: Artificial Sequence
<220> FEATURE:
<223> OTHER INFORMATION: nucleic acid probe

<400> SEQUENCE: 42
ccctcagtgt cacct                                                        15

<210> SEQ ID NO 43
<211> LENGTH: 20
<212> TYPE: DNA
<213> ORGANISM: Artificial Sequence
<220> FEATURE:
<223> OTHER INFORMATION: nucleic acid primer

<400> SEQUENCE: 43
gggaggagac agcttcttga                                                   20

<210> SEQ ID NO 44
```

```
<211> LENGTH: 20
<212> TYPE: DNA
<213> ORGANISM: Artificial Sequence
<220> FEATURE:
<223> OTHER INFORMATION: nucleic acid primer

<400> SEQUENCE: 44
ccaaaatcca tgttgtgagc                                                  20

<210> SEQ ID NO 45
<211> LENGTH: 19
<212> TYPE: DNA
<213> ORGANISM: Artificial Sequence
<220> FEATURE:
<223> OTHER INFORMATION: nucleic acid probe

<400> SEQUENCE: 45
ttcgtgtccc tatgctagt                                                   19

<210> SEQ ID NO 46
<211> LENGTH: 16
<212> TYPE: DNA
<213> ORGANISM: Artificial Sequence
<220> FEATURE:
<223> OTHER INFORMATION: nucleic acid probe

<400> SEQUENCE: 46
tcgtgtccct gtgcta                                                      16

<210> SEQ ID NO 47
<211> LENGTH: 20
<212> TYPE: DNA
<213> ORGANISM: Artificial Sequence
<220> FEATURE:
<223> OTHER INFORMATION: nucleic acid primer

<400> SEQUENCE: 47
taccaggggt gtttccctta                                                  20

<210> SEQ ID NO 48
<211> LENGTH: 22
<212> TYPE: DNA
<213> ORGANISM: Artificial Sequence
<220> FEATURE:
<223> OTHER INFORMATION: nucleic acid primer

<400> SEQUENCE: 48
ttgttaattt ctgtctgcca ca                                               22

<210> SEQ ID NO 49
<211> LENGTH: 14
<212> TYPE: DNA
<213> ORGANISM: Artificial Sequence
<220> FEATURE:
<223> OTHER INFORMATION: nucleic acid probe

<400> SEQUENCE: 49
cataggcaag tttc                                                        14

<210> SEQ ID NO 50
<211> LENGTH: 16
<212> TYPE: DNA
<213> ORGANISM: Artificial Sequence
```

```
<220> FEATURE:
<223> OTHER INFORMATION: nucleic acid probe

<400> SEQUENCE: 50
cataggccag tttcat                                                    16
```